US010654815B2

(12) United States Patent
Yang et al.

(10) Patent No.: US 10,654,815 B2
(45) Date of Patent: May 19, 2020

(54) UREA COMPOUND AND PREPARATION METHOD AND APPLICATION THEREOF

(71) Applicant: SHENZHEN CHIPSCREEN BIOSCIENCES CO., LTD., Shenzhen, Guangdong (CN)

(72) Inventors: Qianjiao Yang, Guangdong (CN); Xianping Lu, Guangdong (CN); Zhibin Li, Guangdong (CN); Lijun Xin, Guangdong (CN); Yonglian Song, Guangdong (CN); Chao Fu, Guangdong (CN)

(73) Assignee: SHENZHEN CHIPSCREEN BIOSCIENCES CO., LTD., Shenzhen, Guangdong (CN)

( * ) Notice: Subject to any disclaimer, the term of this patent is extended or adjusted under 35 U.S.C. 154(b) by 0 days.

(21) Appl. No.: 16/474,003

(22) PCT Filed: Dec. 27, 2017

(86) PCT No.: PCT/CN2017/118844
§ 371 (c)(1),
(2) Date: Jun. 26, 2019

(87) PCT Pub. No.: WO2018/121560
PCT Pub. Date: Jul. 5, 2018

(65) Prior Publication Data
US 2019/0337906 A1   Nov. 7, 2019

(30) Foreign Application Priority Data
Dec. 29, 2016   (CN) .......................... 2016 1 1245660

(51) Int. Cl.
C07D 265/30   (2006.01)
C07C 275/24   (2006.01)
C07D 405/12   (2006.01)
C07D 413/14   (2006.01)

(52) U.S. Cl.
CPC .......... C07D 265/30 (2013.01); C07C 275/24 (2013.01); C07D 405/12 (2013.01); C07D 413/14 (2013.01)

(58) Field of Classification Search
CPC .. C07D 265/30; C07D 405/12; C07D 413/15; C07C 275/24
See application file for complete search history.

(56) References Cited

U.S. PATENT DOCUMENTS

2016/0194307 A1    7/2016  Chupak et al.
2019/0233405 A1*   8/2019  Feng .................... C07D 319/18

FOREIGN PATENT DOCUMENTS

CN   105705489 A     6/2016
WO   2015057250 A1   4/2015
WO   2015160641 A2   10/2015

OTHER PUBLICATIONS

International Search Report for PCT/CN2017/118844 dated Mar. 30, 2018, ISA/CN.
Ahmad, Md Faiz, et al., Identification of Non-nucleoside Human Ribonucleotide Reductase Modulators. Journal of Medicinal Chemistry, Oct. 21, 2015, 58(24), 9498-9508.
Couzin-Frankel J., Cancer Immunotherapy, 2013, Science, vol. 342, 1432-1433.
Sharma P., Allison J.P., The future of immune checkpoint therapy, 2015, Science, vol. 348, 56-61.
Mellman Ira, et al., Cancer immunotherapy comes of age, 2011, Nature, 480, 480-489.
Pardoll D.M., et al., The blockade of immune checkpoints in cancer immunotherapy, 2012, 12(4), 252-264.
Cheng Xiaoxiao, et al., Structure and Interactions of the Human Programmed Cell Death 1 Receptor,2013,vol. 288, 11771-11785.
Lázár-Molnár E., et al., Proc. Natl. Acad. Sci. USA., Crystal structure of the complex between programmed death-1 (PD-1) and its ligand PD-L2, 2008, vol. 105, 10483-10488.

(Continued)

Primary Examiner — Timothy R Rozof
(74) Attorney, Agent, or Firm — Yue (Robert) Xu; Apex Attorneys at Law, LLP

(57) ABSTRACT

The present invention relates to a urea compound and a preparation method and an application thereof. The structure of the present compound is represented by formula (I), the definition of each variable in the formula being as described in the description. The compound can block interaction between the PD-1/PD-L1 signalling pathways. The compound of the present invention can be used for treating or preventing diseases related to the signalling pathways, such as cancer, autoimmune disease, chronic infectious disease, and other diseases.

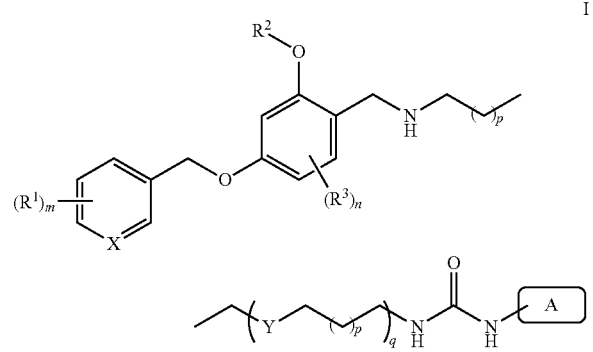

25 Claims, No Drawings

(56) References Cited

OTHER PUBLICATIONS

Ghiotto M., Gauthier L., Serriari N., PD-L1 and PD-L2 differ in their molecular mechanisms of interaction with PD-1, 2010, Int. Immunol., 22, 651-660.

Fuller M.J., Callendret B., Zhu B., Immunotherapy of chronic hepatitis C Virus infection with antibodies against programmed cell death-1 (PD-1), 2013, Proc. Natl. Acad. Sci. USA., vol. 110, 15001-15006.

Dolan D.E., Gupta S., PD-1 Pathway Inhibitors: Changing the Landscape of Cancer Immunotherapy, 2014, Cancer Control, vol. 21, 231-237.

Chen L., Flan X., J. Clin. Invest., Anti-PD-1/PD-L1 therapy of human cancer: past, present, and future, 2015, vol. 125, 3384-3391.

Postow M.A., Callahan M.K., Wolchok J.D., Immune Checkpoint Blockade in Cancer Therapy 2015, J. Clin. Oncol., 33: 1974-1982.

Li Y., Li F., et al., A Mini-Revies for Cancer Immunotherapy: Molecular Understanding of PD-1/PD-L1 Pathway & Translational Blockade of Immune Checkpoints, 2016, Int. J. Mol. Sci., 17: E1151.

\* cited by examiner

UREA COMPOUND AND PREPARATION METHOD AND APPLICATION THEREOF

This application is the national phase of International Application No. PCT/CN2017/118844, titled "UREA COMPOUND AND PREPARATION METHOD AND APPLICATION THEREOF", filed on Dec. 27, 2017, which claims the priority of Chinese Patent Application No. 201611245660.1, filed on Dec. 29, 2016, filed with China National Intellectual Property Administration, and titled with "UREA COMPOUND AND PREPARATION METHOD AND APPLICATION THEREOF", and the disclosures of which are hereby incorporated by reference.

FIELD

The present disclosure relates to the field of medical technology, to a urea compound that is able to block the interaction between the PD-1/PD-L1 signaling pathways. The present disclosure also relates to a method for preparing the compound, a pharmaceutical composition containing the compound as an active ingredient and pharmaceutical uses thereof. The compound of the present disclosure may be used as the immune checkpoint inhibitor targeting the interaction between the PD-1/PD-L1 signaling pathways, which is used for treating/preventing diseases related to the signaling pathways, such as cancer, autoimmune disease, chronic infectious disease, and other diseases.

BACKGROUND

Cancer immunotherapy is a new therapy that inhibits or kills cancer cell by activating the human immune system and enhancing the antitumor immunity of oneself. This method has made breakthroughs after more than 100 years of hard work. In 2013, *Science* ranked tumor immunotherapy as the winner of the Top 10 scientific breakthroughs of this year (Couzin-Frankel J., 2013, Science, 342: 1432-1433). Tumor immunotherapy has become one of the most promising fields of antitumor therapy. This therapy mainly includes immune checkpoint inhibitor and cell therapy. In recent years, immune checkpoint inhibitor is a popular research topic in the field, which has made a significant clinical research progress, providing a new weapon for combating cancer (Sharma P, Allison J. P., 2015, Science, 348: 56-61).

Compared with normal cells, tumor cells have many genetic and epigenetic changes. Immune system can use the surface antigens produced by tumor cells to distinguish the two, thereby triggering the antitumor immune response. In the process of T cell antitumor immunity, after the T cell is activated by the T cell receptor (TCR)-mediated antigen recognition signal, T cell effect is comprehensively regulated through costimulatory signals and coinhibitory signals. These signals are called immune checkpoint, including inhibitory receptors that inhibits the signals such as cytotoxic T-lymphocyte associated antigen 4 (CTLA4), programmed death protein 1 (PD-1), V-domain immunoglobulin suppressor of T-cell activation (VISTA), T cell immunoglobulin and mucin domain-containing-3 (TIM3), lymphocyte activation gene 3 (LAG3), etc., and activating receptors that stimulates the signals such as CD28, CD134 (OX40), glucocorticoid-induced TNFR-related protein (GITR), CD137, CD27, HVEM, etc. (reference is made to FIG. 1) (Mellman I., Coukos G., Dranoff G., 2011, Nature, 480: 480-489). Under normal physiological conditions, the immune checkpoints on one hand participate in maintaining immune tolerance of the autoantigen to avoid autoimmune disease; and on the other hand avoid tissue injury caused by excessive activation of immune response. However, the tumor cells may evade immune killing by immune checkpoints inhibiting T cell activation. Therefore, it is necessary to reactivate T cells to attack tumor cells by activating the costimulatory signals (step on "accelerator") and inhibiting the coinhibitory signals (loose "brake"), thereby realizing tumor immunotherapy. Clinical researches show that immune checkpoint blockade is one of the key strategies of T cell activation, and the successful listing of several antibody drugs and huge market potential have undoubtedly made the research of immune checkpoints the focus of major pharmaceutical companies at home and abroad (Pardoll D. M., 2012, Nat. Rev. Cancer., 12: 252-264). At present, PD-1 is one of the most popular immune checkpoints.

PD-1 is expressed in activated T cell, B cell, and bone marrow cell, and belongs to CD28 family. It is a type 1 transmembrane glycoprotein on T cell and is consisted of 288 amino acids. PD-1 has a molecular structure consisting of an immunoglobulin IgV-like (amino acid 35-145) extracellular domain, a transmembrane domain and a cytoplasmic tail region having a function of connecting signal peptide, wherein the extracellular domain binds to the ligand to play an important function (Cheng X., Veverka V, Radhakrishnan A., et al. 2013, J. Biol. Chem., 288: 11771-11785). The ligand of D-1 includes two types, programmed death protein ligand 1 (PD-L1) and programmed death protein ligand 2 (PD-L2), wherein PD-L1 is constitutively expressed on a variety of cancer cells, T cells, APC and a variety of non-hematopoietic cells; and PD-L2 is restrictively expressed only in dendritic cells and macrophages. PD-L1/2 belongs to B7 family, and is type 1 transmembrane glycoproteins. PD-L1 is consisted of 290 amino acids; and PD-L2 is consisted of 262 amino acids. The molecular structures of PD-L1/2 are all consisted of an immunoglobulin IgV-like domain (distal end of the membrane), an IgC-like domain (proximal end of the membrane), a transmembrane domain and a short and conserved cytoplasmic domain (Lázár-Molnár E., Yan Q., Cao E., et al. 2008, Proc. Natl. Acad. Sci. USA., 105: 10483-10488). Isothermal titration calorimetry (ITC) experiments show that the interaction between PD-1 and PD-L1 is derived by entropy change, and the interaction between PD-1 and PD-L2 is derived by enthalpy change. The two competitively bind with the PD-1, and the affinity between PD-L2 and PD-1 is 3-4 times that of PD-L1 and PD-1. This weak interaction may be the key to triggering the latent inhibition signal (Ghiotto M., Gauthier L., Serriari N., et al. 2010, Int. Immunol., 22: 651-660). The interaction between PD-1 and its ligand inhibits T cell activation, which is essential for maintaining normal immune tolerance in the body. In tumor cells and when the virus is infected, PD-1 on T cells is induced to high expression and the expression of PD-L1/2 is up-regulated, resulting in continuous activation of PD-1 signaling pathway and inhibition of T cell proliferation (see FIG. 2), and resulting in immune escape of tumor cells and pathogens (Fuller M. J., Callendret B., Zhu B., et al. 2013, Proc. Natl. Acad. Sci. USA., 110: 15001-15006; Dolan D. E., Gupta S., 2014, Cancer Control, 21: 231-237; Chen L., Han X., 2015, J. Clin. Invest., 125: 3384-3391; Postow M. A., Callahan M. K., Wolchok J. D., 2015, J. Clin. Oncol., 33: 1974-1982).

Currently, three antibody drugs that block this signaling pathway have been approved by the FDA, and multiple antibody drugs worldwide are in clinical research (see Table 1) (Li Y, Li F., Jiang F., et al. 2016, Int. J. Mol. Sci., 17: E1151). Several studies have confirmed that these antibody drugs are effective in a variety of tumors, such as melanoma, non-small cell lung cancer, renal cell carcinoma, ovarian cancer, bladder cancer, stomach cancer, head and neck and esophageal squamous cell carcinoma, and Hodgkin's lymphoma.

TABLE 1

| | List of approval and clinical research of target PD-1 and PD-L1 antibody drugs worldwide | | | |
|---|---|---|---|---|
| Target | Active compound | Developer | Type | Clinical status |
| PD-1 | Nivolumab | Bristol-Myers Squibb | human IgG4 | FDA approval: recurrent unresectable melanoma, metastatic non-small cell lung cancer (NSCLC) and a dvanced renal cell carcinoma |
| | Pembrolizumab | Merck | human IgG4 | FDA approval: recurrent unresectable melanoma, metastatic NSCLC that expresses PD-L1 |
| | AMP-224 | Amplimmune | PD-L2 IgG2a fusion protein | PH 1 |
| | AMP-514 | Amplimmune | PD-L2 fusion protein | PH 1-2 |
| | REGN2810 | Regeneron | human IgG4 | PH 1 |
| | PDR001 | Novartis | — | PH 1-2 |
| | BMS-936559 | Bristol-Myers Squibb | human IgG4 | PH 1-2 |
| | BGB-A317 | BeiGene | human IgG4 | PH 1 (U.S.A.) |
| | JS001-PD-1 | Shanghai Junshi | — | PH 1 (China) |
| | SHR-1210 | Shanghai Hengrui | — | PH 1 (China) |
| PD-L1 | MPDL3280A | Roche | human IgG1k | FDA approval: bladder epithelial carcinoma, metastatic NSCLC |
| | MEDI4736 | MedImunne/AstraZeneca | human IgG1k | PH 1-3 |
| | MSB0010718C | Merck Serono | human IgG1 | PH 1-3 |

In view of above, significant progresses have been made in the immune checkpoint inhibitors targeting PD-1/PD-L1 antibody drugs. However, the conventional antibody drugs are required to be administered by injection, have various ADMET problems (drug absorption, distribution, metabolism, excretion and toxicity), or have serious side effects associated with the immune system, etc., which may be due to the too long half-lives of these macromolecules (as long as 15-20 days), causing the target to be continuously inhibited. Compared with conventional antibody drugs, small molecule immune checkpoint inhibitors have obvious advantages, including oral administration is feasible, and side effects are decreased to the utmost extent by regulating the pharmaceutical properties. In addition, small molecule inhibitors will have lower cost and price advantages. To date, in addition to the oral small molecule inhibitors CA-170 (targeting PD-L1/VISTA, Phase I clinical study, U.S.A.) and AUPM-327 (targeting PD-L1/TIM3, preclinical study) reported by Aurigene and Curis, no small molecule inhibitor has been publicly reported.

The small molecular immune checkpoint inhibitors disclosed in the present disclosure may be used for treating and/or preventing melanoma, non-small cell lung cancer, renal cell carcinoma, ovarian cancer, bladder cancer, stomach cancer, head and neck and esophageal squamous cell carcinoma, and Hodgkin's lymphoma, etc., but not limited to this. At the same time, these compounds or the pharmaceutical compositions containing them as active ingredient may maximize the clinical efficacy of these diseases in a safe therapeutic window.

SUMMARY

One aspect of the present disclosure relates to urea compounds that are able to block the interaction between the PD-1/PD-L1 signaling pathways, including derivatives thereof, such as pharmaceutical acceptable salts, hydrates, stereoisomers, and prodrugs thereof.

Another aspect of the present disclosure relates to a method for preparing the compound of the present disclosure.

A further aspect of the present disclosure relates to a pharmaceutical composition using the compound of the present disclosure as the active ingredient, and clinical use of the compound or pharmaceutical composition of the present disclosure for treating/preventing diseases related to PD-1/PD-L1 signaling pathways, and use of the compound or pharmaceutical composition of the present disclosure in treating and/or preventing diseases related to PD-1/PD-L1 signaling pathways.

The present disclosure relates to a compound of Formula I, comprising a prodrug, a stereoisomer, and a pharmaceutically acceptable salt or hydrate thereof,

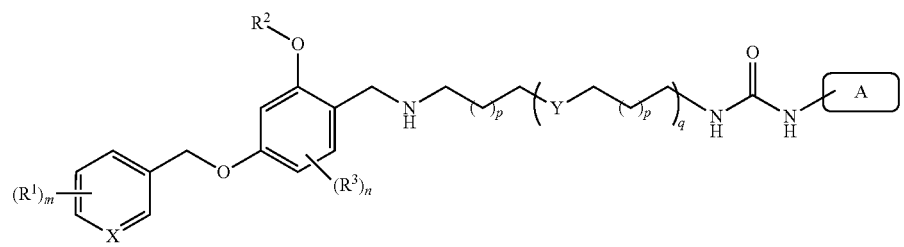

I wherein, $R^1$ is one or more substituents independently selected from the group consisting of H, $C_1$-$C_4$ alkyl, CN, halogen, $NH_2$, COOH, $C_1$-$C_4$ alkylamino, $C_1$-$C_4$ alkyloxy, $C_1$-$C_4$ haloalkyl and $Ar^1$, which substituents are the same or different;

wherein, $Ar^1$ is selected from the group consisting of

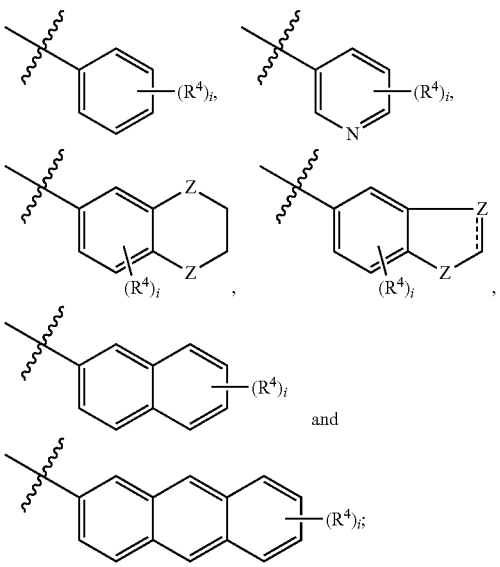

wherein, $R^4$ is one or more substituents independently selected from the group consisting of H, $C_1$-$C_4$ alkyl, CN, halogen, $NH_2$, COOH, $C_1$-$C_4$ alkylamino, $C_1$-$C_4$ alkyloxy and $C_1$-$C_4$ haloalkyl, which substituents are the same or different;

i is an integer from 1 to 5;

Z is selected from the group consisting of C, NH, O, C(O), S, S(O) and S(O)$_2$;

$R^2$ is selected from the group consisting of H, $C_1$-$C_4$ alkyl, —$CH_2$—$(CH_2)_k$—CN and —$(CH_2)_k$—$Ar^2$;

wherein, k is an integer from 0 to 6;

$Ar^2$ is selected from

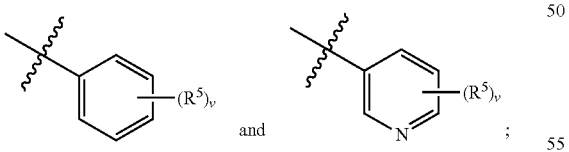

wherein, $R^5$ is one or more substituents independently selected from the group consisting of H, $C_1$-$C_4$ alkyl, CN, halogen, $NH_2$, COOH, $C_1$-$C_4$ alkylamino, $C_1$-$C_4$ alkyloxy and $C_1$-$C_4$ haloalkyl, which substituents are the same or different;

v is an integer from 1 to 5;

$R^3$ is one or more substituents independently selected from the group consisting of H, $C_1$-$C_4$ alkyl, CN, halogen, $C_1$-$C_4$ alkyloxy and $C_1$-$C_4$ haloalkyl, which substituents are the same or different;

X is selected from C and N;

Y is selected from NH, O, S, S(O) and S(O)$_2$;

A is selected from the group consisting of

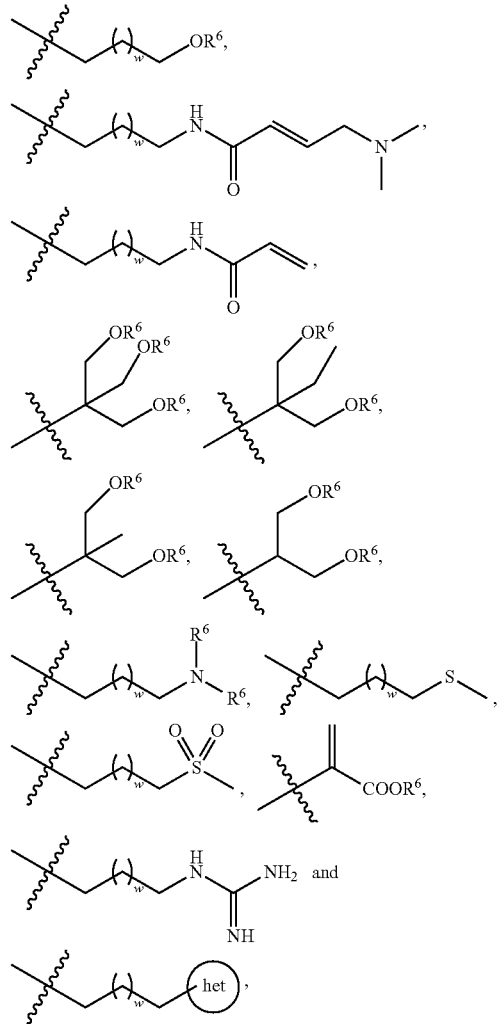

or A is a side chain of an amino acid selected from the group consisting of Gly, Ala, Ser, Lys, Arg, Thr, Asn, Gln, Phe or Glu, for example,

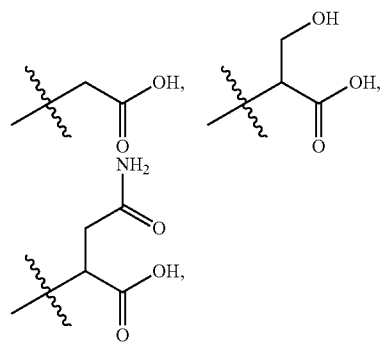

etc., or A is a side chain of an amino acid selected from the group consisting of Gly, Ala, Ser, Lys, Arg, Thr, Asn, Gln, Phe and Glu, which is substituted with $R^6$, for example,

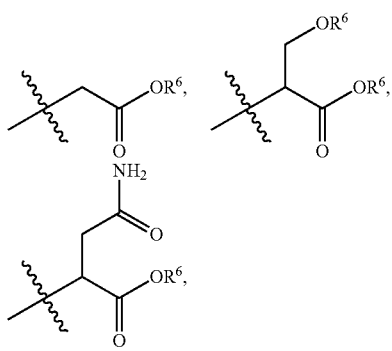

etc., but is not limited to this;

wherein,

R⁶ is one or more substituents independently selected from the group consisting of H, $C_1$-$C_4$ alkyl, $C_1$-$C_4$ alkylcarbonyl, $C_1$-$C_4$ alkenylcarbonyl and $C_1$-$C_4$ alkylamino $C_1$-$C_4$ alkyl $C_1$-$C_4$ alkenylcarbonyl, which substituents are the same or different, but is not limited to this;

het is selected from saturated or aromatic heterocycles, for example morpholine, N-methylpiperazine, tetrahydropyrrole, pyridine, thiophene, thiazole, triazole and tetrazole;

w is an integer from 0 to 2;

m is an integer from 1 to 5;

n is an integer from 1 to 3;

p is independently an integer from 0 to 2; and q is an integer from 0 to 2.

In a preferred aspect, the present disclosure relates to a compound of Formula I, comprising a prodrug, a stereoisomer, and a pharmaceutically acceptable salt or a hydrate thereof, wherein, R¹ is one or more substituents independently selected from the group consisting of H, $C_1$-$C_4$ alkyl, CN, halogen, $NH_2$, COOH, $C_1$-$C_4$ alkylamino, $C_1$-$C_4$ alkyloxy, $C_1$-$C_4$ haloalkyl and Ar¹, which substituents are the same or different;

wherein,

Ar¹ is selected from the group consisting of

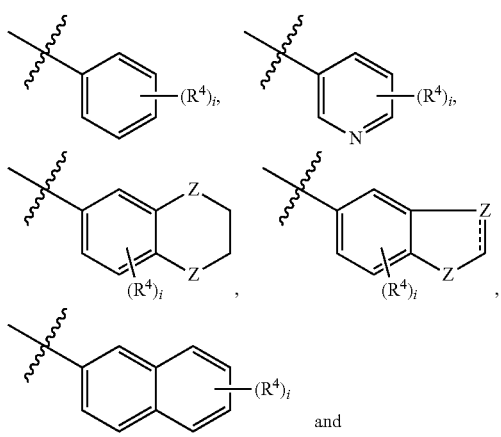

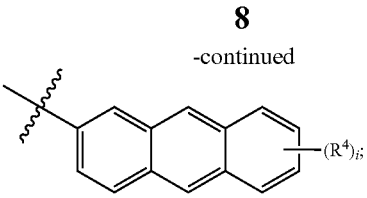

wherein,

R⁴ is one or more substituents independently selected from the group consisting of H, $C_1$-$C_4$ alkyl, CN, halogen, $NH_2$, COOH, $C_1$-$C_4$ alkylamino, $C_1$-$C_4$ alkyloxy and $C_1$-$C_4$ haloalkyl, which substituents are the same or different;

i is an integer from 1 to 5;

Z is selected from the group consisting of C, NH, O, C(O), S, S(O) and $S(O)_2$;

R² is selected from the group consisting of $CH_3$, —$CH_2$—$(CH_2)_k$—CN and —$(CH_2)_k$—Ar²;

wherein, k is an integer from 0 to 6;

Ar² is selected from

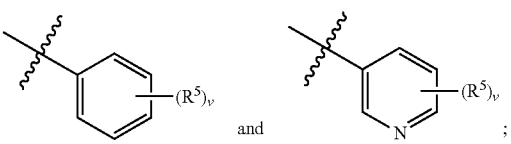

wherein,

R⁵ is one or more substituents independently selected from the group consisting of H, $CH_3$, $C_2H_5$, CN, F, Cl, $NH_2$, COOH, $CH_3NH$, $(CH_3)_2N$, $CH_3O$, $CF_3$ and $CHF_2$, which substituents are the same or different;

v is an integer from 1 to 5;

R³ is one or more substituents independently selected from the group consisting of H, $C_1$-$C_4$ alkyl, CN, halogen, $C_1$-$C_4$ alkyloxy and $C_1$-$C_4$ haloalkyl, which substituents are the same or different X is selected from C and N;

Y is selected from NH, O, S, S(O) and $S(O)_2$;

A is selected from the group consisting of

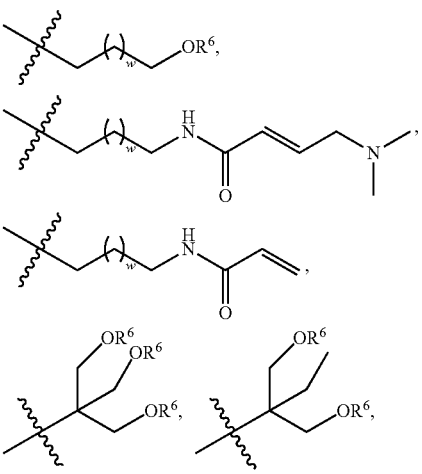

-continued

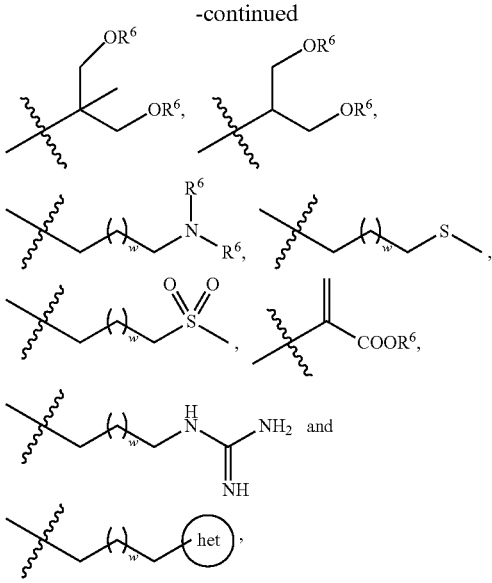

or A is a side chain of an amino acid selected from the group consisting of Gly, Ala, Ser, Lys, Arg, Thr, Asn, Gln, Phe and Glu, for example,

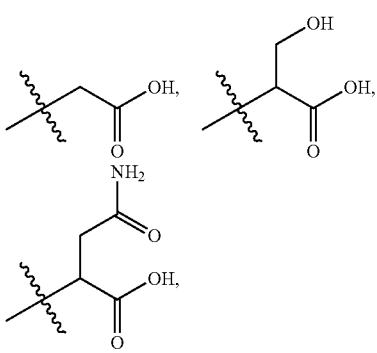

etc., or A is a side chain of an amino acid selected from the group consisting of Gly, Ala, Ser, Lys, Arg, Thr, Asn, Gln, Phe and Glu, which is substituted with $R^6$, for example,

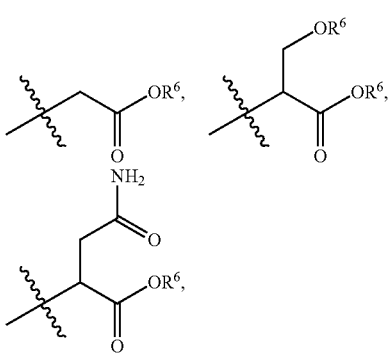

etc., but is not limited to this;
wherein,
$R^6$ is one or more substituents independently selected from the group consisting of H, $C_1$-$C_4$ alkyl, $C_1$-$C_4$ alkylcarbonyl, $C_1$-$C_4$ alkenylcarbonyl and $C_1$-$C_4$ alkylamino $C_1$-$C_4$ alkyl $C_1$-$C_4$ alkenylcarbonyl, which substituents are the same or different;

het is selected from saturated or aromatic heterocycles, for example morpholine, N-methylpiperazine, tetrahydropyrrole, pyridine, thiophene, thiazole, triazole and tetrazole, but is not limited to this;

w is an integer from 0 to 2;

m is an integer from 1 to 5;

n is an integer from 1 to 3;

p is independently an integer from 0 to 2; and q is an integer from 0 to 2.

In a more preferred aspect, the present disclosure relates to a compound of Formula I, comprising a prodrug, a stereoisomer, and a pharmaceutically acceptable salt or a hydrate thereof, wherein, $R^1$ is one or more substituents independently selected from the group consisting of H, $C_1$-$C_4$ alkyl, CN, halogen, $NH_2$, COOH, $C_1$-$C_4$ alkylamino, $C_1$-$C_4$ alkyloxy, $C_1$-$C_4$ haloalkyl and $Ar^1$, which substituents are the same or different;

wherein, $Ar^1$ is selected from the group consisting of

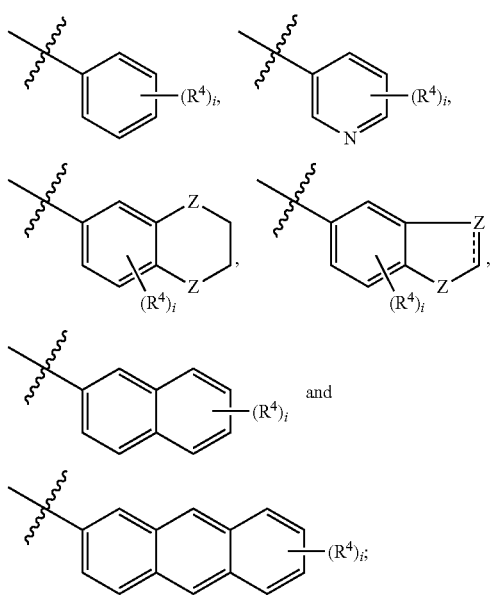

wherein, $R^4$ is one or more substituents independently selected from the group consisting of H, $C_1$-$C_4$ alkyl, CN, halogen, $NH_2$, COOH, $C_1$-$C_4$ alkylamino, $C_1$-$C_4$ alkyloxy and $C_1$-$C_4$ haloalkyl, which substituents are the same or different;

i is an integer from 1 to 5;

Z is selected from the group consisting of C, NH, O, C(O), S, S(O) and $S(O)_2$;

$R^2$ is $—(CH_2)_k—Ar^2$;
  wherein,
  k is 1;
  $Ar^2$ is selected from

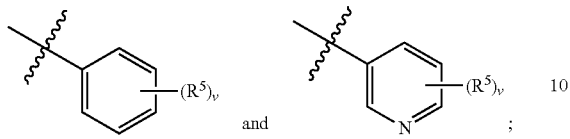

and wherein,
   $R^5$ is one or more substituents independently selected from the group consisting of H, $CH_3$, $C_2H_5$, CN, F, Cl, $NH_2$, COOH, $CH_3NH$, $(CH_3)_2N$, $CH_3O$, $CF_3$, and $CHF_2$, which substituents are the same or different;
   v is an integer from 1 to 5;
$R^3$ is one or more substituents independently selected from the group consisting of H, $CH_3$, $C_2H_5$, CN, F, Cl, $CH_3O$, $CF_3$ and $CHF_2$, which substituents are the same or different;
X is selected from C and N;
Y is selected from NH, O, S, S(O) and $S(O)_2$;
A is selected from the group consisting of

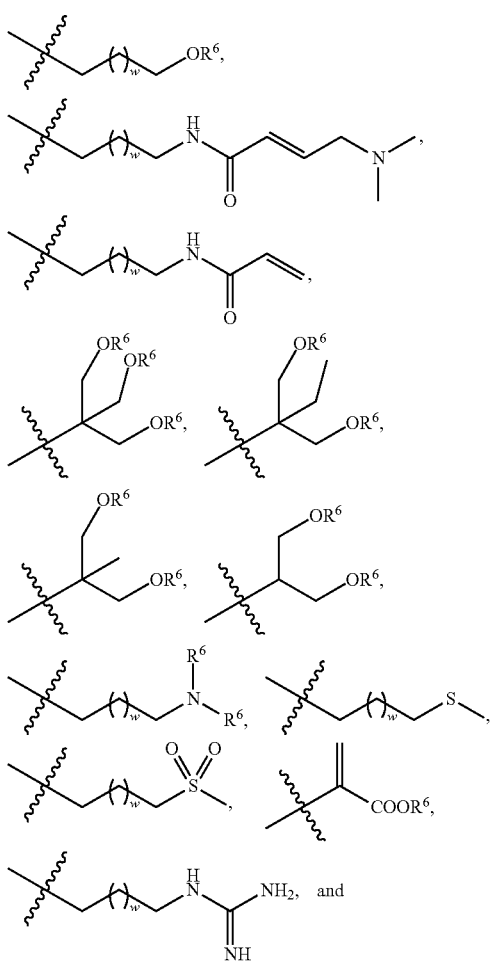

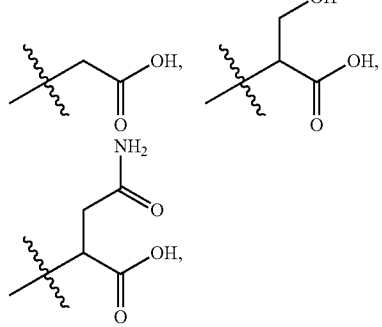

or A is a side chain of an amino acid selected from the group consisting of Gly, Ala, Ser, Lys, Arg, Thr, Asn, Gln, Phe and Glu, for example

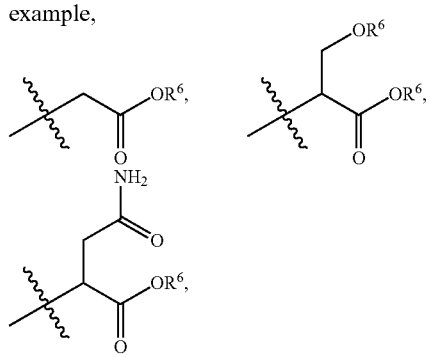

etc., or A is a side chain of an amino acid selected from the group consisting of Gly, Ala, Ser, Lys, Arg, Thr, Asn, Gln, Phe and Glu, which is substituted with $R^6$, for example, etc., but is not limited to this;
wherein,
  $R^6$ is one or more substituents independently selected from the group consisting of H, $C_1$-$C_4$ alkyl, $C_1$-$C_4$ alkylcarbonyl, $C_1$-$C_4$ alkenylcarbonyl and $C_1$-$C_4$ alkylamino $C_1$-$C_4$ alkyl $C_1$-$C_4$ alkenylcarbonyl, which substituents are the same or different;
  het is selected from saturated or aromatic heterocycles, for example morpholine, N-methylpiperazine, tetrahydropyrrole, pyridine, thiophene, thiazole, triazole and tetrazole, but is not limited to this;
  w is an integer from 0 to 2;
  m is an integer from 1 to 5;
  n is an integer from 1 to 3;
  p is independently an integer from 0 to 2; and
  q is an integer from 0 to 2.
In another more preferred aspect, the present disclosure relates to a compound of Formula I, comprising a prodrug, a stereoisomer, and a pharmaceutically acceptable salt or a hydrate thereof,
  wherein,
  $R^1$ is one or more substituents independently selected from the group consisting of H, $C_1$-$C_4$ alkyl, CN, halogen, $NH_2$, COOH, $C_1$-$C_4$ alkylamino, $C_1$-$C_4$ alkyloxy, $C_1$-$C_4$ haloalkyl and $Ar^1$, which substituents are the same or different;

wherein,
Ar¹ is selected from the group consisting of

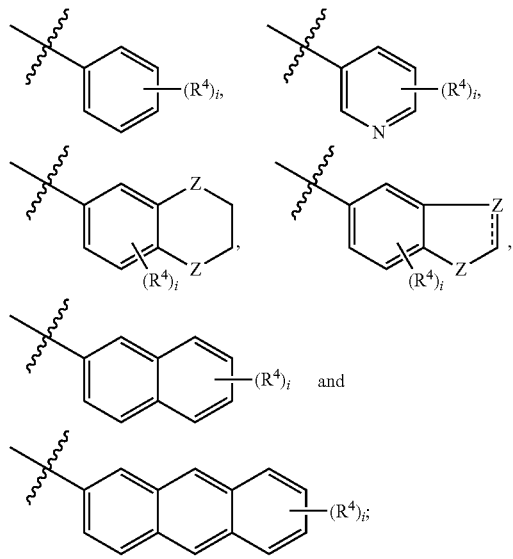

wherein,
R⁴ is one or more substituents independently selected from the group consisting of H, $C_1$-$C_4$ alkyl, CN, halogen, $NH_2$, COOH, $C_1$-$C_4$ alkylamino, $C_1$-$C_4$ alkyloxy and $C_1$-$C_4$ haloalkyl, which substituents are the same or different;
i is an integer from 1 to 5;
Z is selected from the group consisting of C, NH, O, C(O), S, S(O) and $S(O)_2$;
$R^2$ is —$(CH_2)_k$—$Ar^2$;
wherein,
k is 1;
$Ar^2$ is selected from and

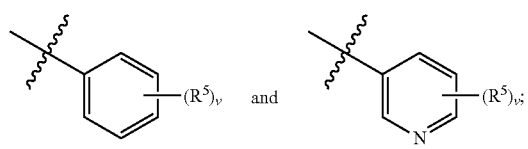

wherein,
$R^5$ is one or more substituents independently selected from the group consisting of H, $CH_3$, $C_2H_5$, CN, F, Cl, $NH_2$, COOH, $CH_3NH$, $(CH_3)_2N$, $CH_3O$, $CF_3$ and $CHF_2$, which substituents are the same or different;
v is an integer from 1 to 5;
$R^3$ is one or more substituents independently selected from the group consisting of $CH_3$, CN, F, Cl, $CH_3O$, $CF_3$ and $CHF_2$, which substituents are the same or different;
X is selected from C and N;
Y is selected from NH, O, S, S(O) and $S(O)_2$;
A is selected from the group consisting of

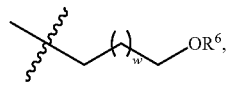

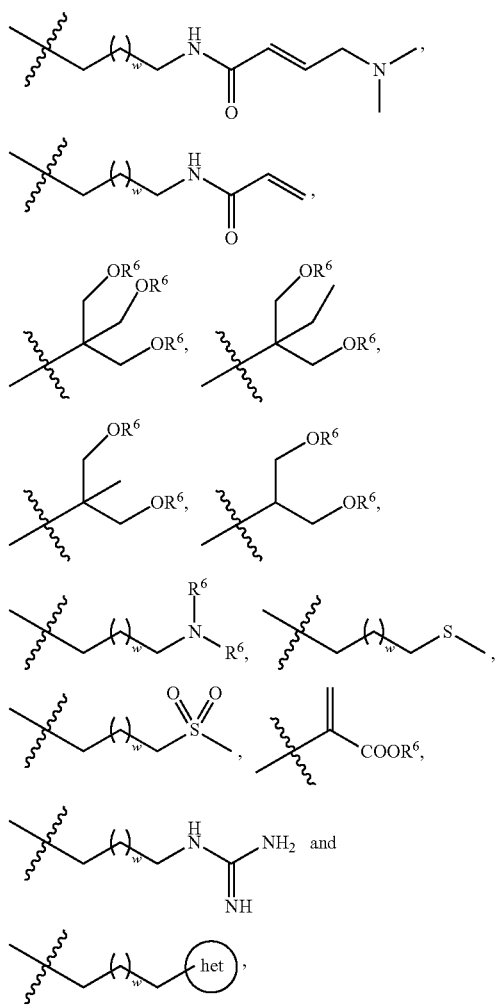

A is a side chain of an amino acid selected from the group consisting of Gly, Ala, Ser, Lys, Arg, Thr, Asn, Gln, Phe and Glu, for example,

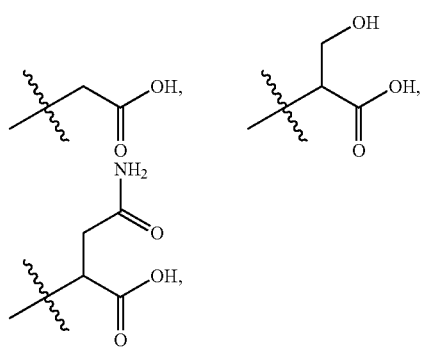

etc., or A is a side chain of an amino acid selected from the group consisting of Gly, Ala, Ser, Lys, Arg, Thr, Asn, Gln, Phe and Glu, which is substituted with $R^6$, for example,

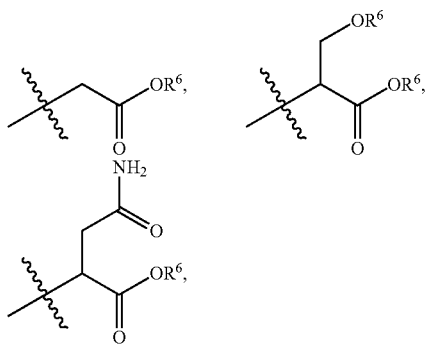

etc., but is not limited to this;
wherein,
$R^6$ is one or more substituents independently selected from the group consisting of H, $CH_3$, $C_2H_5$, t-Bu, $CH_3CO$, $CH_2=CHCO$ and $(CH_3)_2NCH_2CH=CHCO$, which substituents are the same or different;
het is selected from saturated or aromatic heterocycles, for example morpholine, N-methylpiperazine, tetrahydropyrrole, pyridine, thiophene, thiazole, triazole and tetrazole, but is not limited to this;
w is an integer from 0 to 2;
m is an integer from 1 to 5;
n is an integer from 1 to 3;
p is independently an integer from 0 to 2; and
q is an integer from 0 to 2.

In a further more preferred aspect, the present disclosure relates to a compound of Formula I, comprising a prodrug, a stereoisomer, and a pharmaceutically acceptable salt or a hydrate thereof,
wherein,
$R^1$ is one or more substituents independently selected from the group consisting of H, $CH_3$, $C_2H_5$, CN, F, Cl, $NH_2$, COOH, $CH_3NH$, $(CH_3)_2N$, $CH_3O$, $CF_3$, $CHF_2$ and $Ar^1$, which substituents are the same or different;
wherein,
$Ar^1$ is selected from the group consisting of

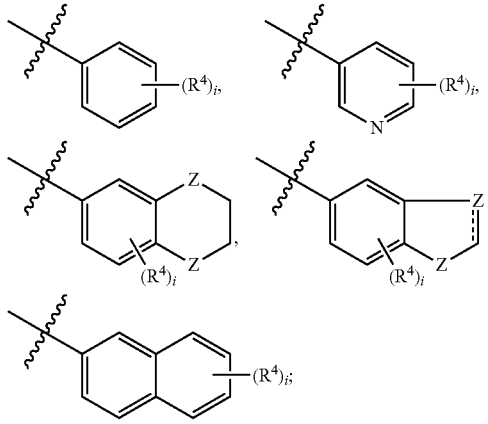

wherein,
$R^4$ is one or more substituents independently selected from the group consisting of H, $CH_3$, $C_2H_5$, CN, F, Cl, $NH_2$, COOH, $CH_3NH$, $(CH_3)_2N$, $CH_3O$, $CF_3$ and $CHF_2$, which substituents are the same or different;
i is an integer from 1 to 3;
Z is selected from the group consisting of C, NH, O, C(O), S, S(O) and $S(O)_2$;
$R^2$ is $—(CH_2)_k—Ar^2$;
wherein,
k is 1;
$Ar^2$ is selected from

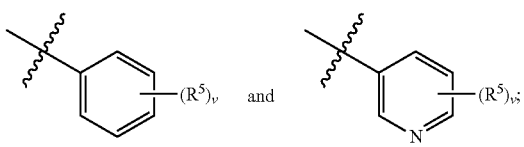

wherein,
$R^5$ is one or more substituents independently selected from the group consisting of H, $CH_3$, $C_2H_5$, CN, F, Cl, $(CH_3)_2N$, $CF_3$ and $CHF_2$, which substituents are the same or different;
v is 1;
$R^3$ is one or more substituents independently selected from the group consisting of $CH_3$, CN, F, Cl, $CH_3O$, $CF_3$ and $CHF_2$, which substituents are the same or different;
X is C;
Y is selected from NH, O, S, S(O) and $S(O)_2$;
A is selected from the group consisting of

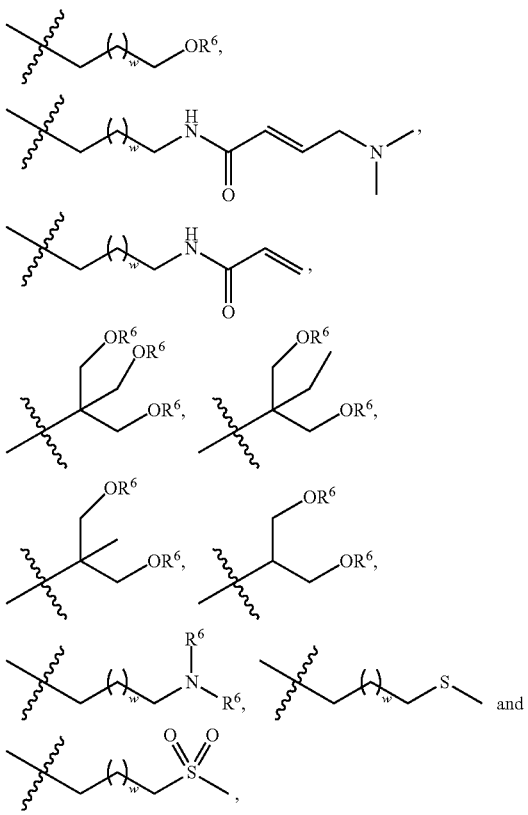

and or A is a side chain of an amino acid selected from the group consisting of Gly, Ala, Ser, Lys, Arg, Thr, Asn, Gln, Phe and Glu, for example,

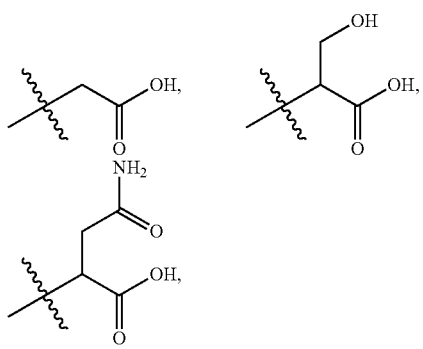

etc., or A is a side chain of an amino acid selected from the group consisting of Gly, Ala, Ser, Lys, Arg, Thr, Asn, Gln, Phe and Glu, which is substituted with $R^6$, for example,

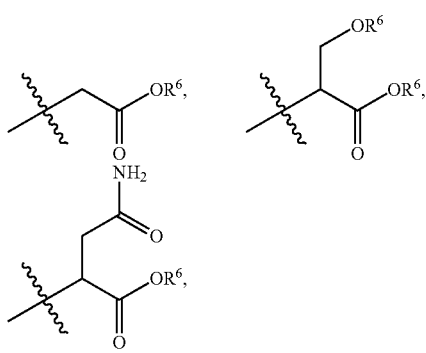

etc., but is not limited to this;

wherein, $R^6$ is one or more substituents independently selected from the group consisting of H, $CH_3$, $C_2H_5$, t-Bu, $CH_3CO$, $CH_2=CHCO$ and $(CH_3)_2NCH_2CH=CHCO$, which substituents are the same or different;

w is an integer from 0 to 2;

m is an integer from 1 to 3;

n is an integer from 1 to 2;

p is independently an integer from 0 to 2; and q is an integer from 0 to 2.

In a further more preferred aspect, the present disclosure relates to a compound of Formula I, comprising a prodrug, a stereoisomer, and a pharmaceutically acceptable salt or a hydrate thereof, wherein, $R^1$ is one or more substituents independently selected from the group consisting of $CH_3$, CN, F, Cl, $CF_3$ and $Ar^1$, which substituents are the same or different;

wherein, $Ar^1$ is selected from the group consisting of

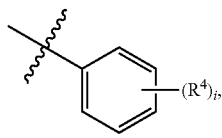 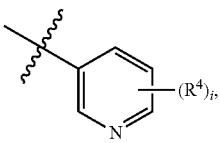

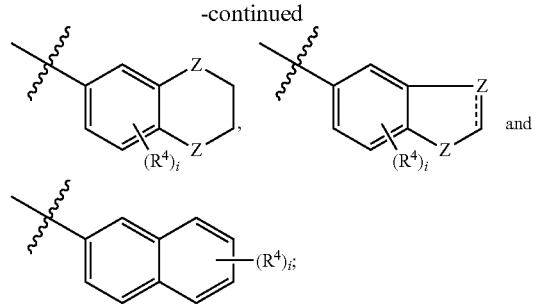

wherein, $R^4$ is one or more substituents independently selected from the group consisting of H, $CH_3$, CN, F, Cl, $(CH_3)_2N$, $CF_3$ and $CHF_2$, which substituents are the same or different;

i is an integer from 1 to 3;

Z is selected from the group consisting of C, NH, O, C(O), S, S(O) and $S(O)_2$;

$R^2$ is $-(CH_2)_k-Ar^2$;

wherein, k is 1;

$Ar^2$ is selected from

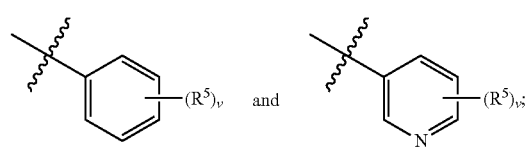

wherein, $R^5$ is one or more substituents independently selected from the group consisting of $CH_3$, CN, F, $(CH_3)_2N$, $CF_3$ and $CHF_2$, which substituents are the same or different;

v is 1;

$R^3$ is one or more substituents independently selected from the group consisting of $CH_3$, CN, F, Cl, $CH_3O$, $CF_3$ and $CHF_2$, which substituents are the same or different;

X is C;

Y is selected from NH, O, S, S(O) and $S(O)_2$;

A is selected from the group consisting of

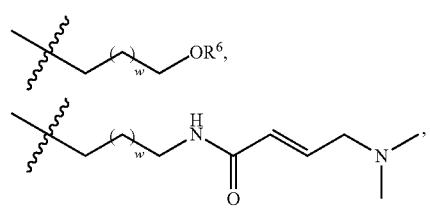

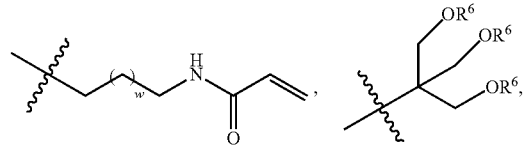

-continued or A is a side chain of an amino acid selected from the group consisting of Gly, Ala, Ser, Lys, Arg, Thr, Asn, Gln, Phe and Glu, for example, etc., or A is a side chain of an amino acid selected from the group consisting of Gly, Ala, Ser, Lys, Arg, Thr, Asn, Gln, Phe and Glu, which is substituted with $R^6$, for example, etc., but is not limited to this;
wherein,
$R^6$ is one or more substituents independently selected from the group consisting of H, $CH_3CO$, $CH_2$=CHCO and $(CH_3)_2NCH_2CH$=CHCO, which substituents are the same or different;
w is 1;
m is an integer from 1 to 3;
n is an integer from 1 to 2;
p is independently an integer from 0 to 2; and
q is an integer from 0 to 2.

In a particularly more preferred aspect, the present disclosure relates to a compound of Formula I, comprising a prodrug, a stereoisomer, and a pharmaceutically acceptable salt or a hydrate thereof,
wherein,
$R^1$ is one or more substituents independently selected from the group consisting of $CH_3$, CN, F, Cl, $CF_3$ and $Ar^1$, which substituents are the same or different;
wherein,
$Ar^1$ is selected from the group consisting of wherein,
$R^4$ is one or more substituents independently selected from the group consisting of H, $CH_3$, CN, F, Cl, $(CH_3)_2N$, $CF_3$ and $CHF_2$, which substituents are the same or different;
i is an integer from 1 to 3;
Z is selected from the group consisting of C, NH, O and C(O);
$R^2$ is —$(CH_2)_k$—$Ar^2$;
wherein,
k is 1;
$Ar^2$ is;

wherein,
$R^5$ is one or more substituents independently selected from the group consisting of $CH_3$, CN, F, $(CH_3)_2N$, $CF_3$ and $CHF_2$, which substituents are the same or different;
v is 1;
$R^3$ is one or more substituents independently selected from the group consisting of $CH_3$, F, Cl and $CH_3O$, which substituents are the same or different;
X is C;
Y is selected from NH and O;
A is selected from the group consisting of -continued

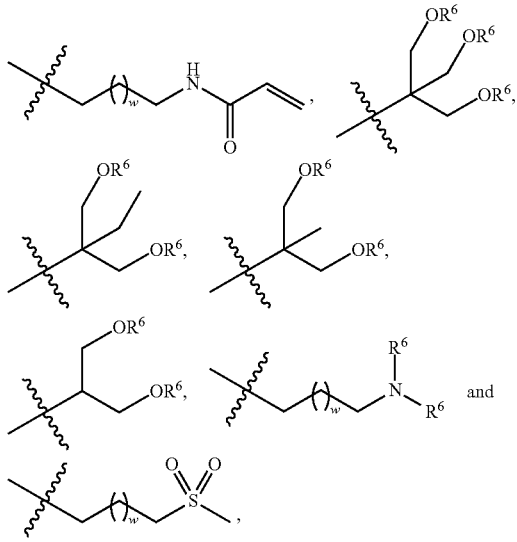

or A is a side chain of an amino acid selected from the group consisting of Gly, Ala, Ser, Lys, Arg, Thr, Asn, Gln, Phe and Glu, for example,

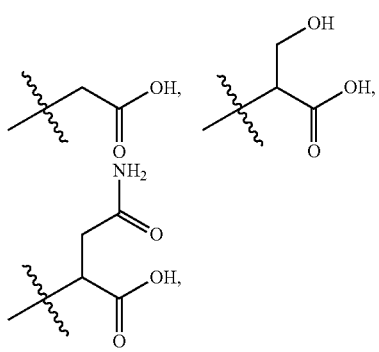

etc., or A is a side chain of an amino acid selected from the group consisting of Gly, Ala, Ser, Lys, Arg, Thr, Asn, Gln, Phe and Glu, which is substituted with $R^6$, for example,

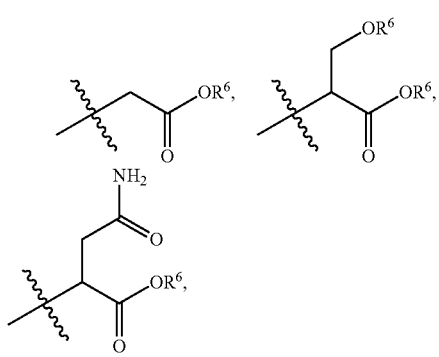

etc., but is not limited to this;
wherein,
$R^6$ is one or more substituents independently selected from the group consisting of H and $CH_3CO$, which substituents are the same or different;

w is 1;
m is 2;
n is an integer from 1 to 2;
p is 0; and
q is an integer from 0 to 1.

In an especially more preferred aspect, the present disclosure relates to a compound of Formula I, comprising a prodrug, a stereoisomer, and a pharmaceutically acceptable salt or a hydrate thereof,
wherein,
$R^1$ is two substituents independently selected from the group consisting of $CH_3$, CN, and
$Ar^1$, which substituents are the same or different;
wherein,
$Ar^1$ is

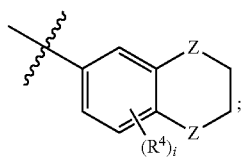

wherein,
$R^4$ is selected from the group consisting of H, $CH_3$, CN, F or Cl;
i is 1;
Z is O;
$R^2$ is $-(CH_2)_k-Ar^2$;
wherein,
k is 1;
$Ar^2$ is N

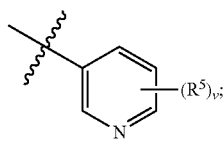

wherein,
$R^5$ is one or more substituents independently selected from the group consisting of $CH_3$, CN, F, $(CH_3)_2N$ and $CF_3$, which substituents are the same or different;
v is 1;
$R^3$ is one or more substituents independently selected from the group consisting of $CH_3$, F, Cl and $CH_3O$, which substituents are the same or different;
X is C;
Y is selected from NH and O;
A is selected from the group consisting of

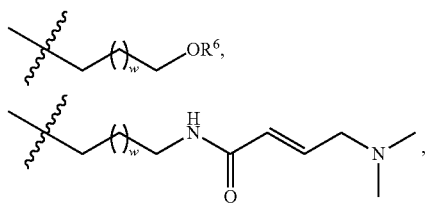

-continued

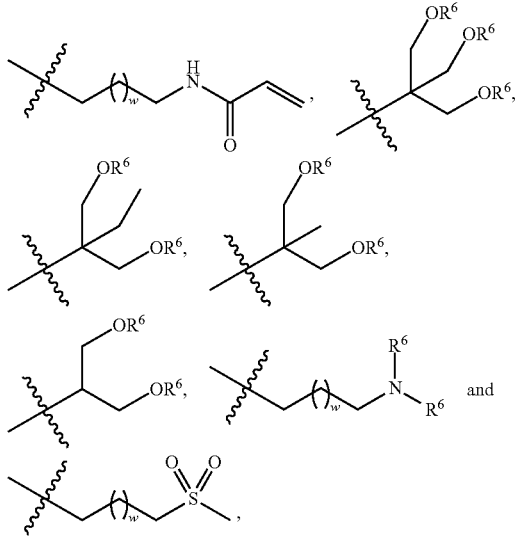

or A is a side chain of an amino acid selected from the group consisting of Gly, Ala, Ser, Lys, Arg, Thr, Asn, Gln, Phe and Glu, for example,

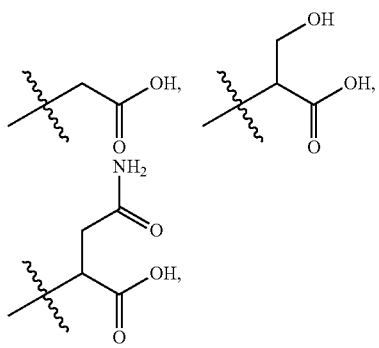

etc., or A is a side chain of an amino acid selected from the group consisting of Gly, Ala, Ser, Lys, Arg, Thr, Asn, Gln, Phe and Glu, which is substituted with $R^6$, for example,

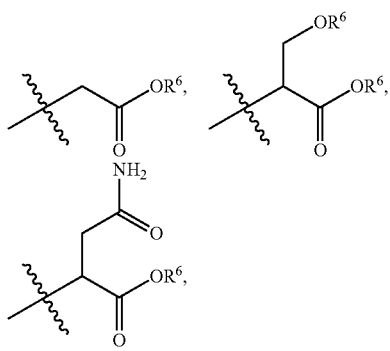

etc., but is not limited to this;
wherein,
$R^6$ is one or more substituents independently selected from the group consisting of H and $CH_3CO$, which substituents are the same or different;

w is 1;
m is 2;
n is an integer from 1 to 2;
p is 0; and
q is an integer from 0 to 1.

BRIEF DESCRIPTION OF DRAWINGS

FIG. 1 shows the mechanism of comprehensively regulating T cell response through costimulatory signals and coinhibitory signals.

FIG. 2 shows the signaling pathways of interaction of PD-1 and PD-L1.

FIG. 3 is a schematic diagram of principle of PD-1/PD-L1 binding inhibition detection (HTRF).

FIG. 4 shows the influences of compound I-5 on promoting IL-2 secretion of PBMC cells in a variety of volunteers.

DETAILED DESCRIPTION

In the present disclosure, the "halogen" is fluorine, chlorine, bromine or iodine, preferably fluorine or chlorine.

In the present disclosure, "alkyl" includes straight or branched or cyclic alkyl. The $C_1$-$C_4$ alkyl in the present disclosure is alkyl having 1 to 4 carbon atoms, preferably methyl, ethyl, propyl or isopropyl, n-butyl, isobutyl or t-butyl. The alkyl in the compound of the present disclosure may be optionally substituted or unsubstituted, and the substituent may include alkyl, halogen, alkoxy, hydrocarbyl, hydroxyl, etc. Examples of the alkyl of the present disclosure include methyl, ethyl, n-propyl, isopropyl, n-butyl, isobutyl, t-butyl, etc.

The "alkoxyl" in the present disclosure refers to a group formed by bonding the above alkyl to an oxygen atom, wherein the oxygen atom has a free bonding ability, for example, methoxyl, ethoxyl, propoxyl, butoxyl, isopropoxyl, t-butoxyl, cyclopropoxyl, etc.

The "alkylcarbonyl" in the present disclosure refers to a group formed by bonding the above alkyl to carbonyl, for example, acetyl, propionyl, isopropionyl, butyryl, cyclopropionyl, etc.

The "alkylamino" in the present disclosure refers to a group formed by bonding the alkyl to amino, such as methylamino, ethylamino, 4-dimethylamino, etc.

In the present disclosure, "medicinal" or "pharmaceutically acceptable" is understood to be suitable for human and animal within a reasonable medical context, and tolerable, without unacceptable side effects including toxicity, anaphylaxis, irritation, complications, etc.

The present disclosure relates to a pharmaceutical composition, comprising the above compound of Formula I, including the prodrug, stereoisomer and pharmaceutical acceptable salts or hydrate thereof as the active ingredient, and optional pharmaceutically acceptable carrier, adjuvant, excipient, etc. The pharmaceutically acceptable carrier, adjuvant or excipient refers to any diluent, adjuvant and carrier which can be used in the pharmaceutical field, for example, but not limited to, the materials listed in the Handbook of Pharmaceutical Excipients 8th ed, 2013.

The compound in the present disclosure may optionally be used in combination with one or more other active ingredients, and the respective amounts and ratios of which may be adjusted by one ordinary skilled in the art depending on the particular disease, the particular conditions of the patient, and the clinical requirement, etc.

The preparations of the present disclosure usually contain 0.5-70% by weight of active ingredient; preferably, contain 1-20% by weight of active ingredient.

The compound of Formula I according to the present disclosure may be administered clinically to mammals, including humans, by oral or injection means, preferably in an oral manner. The dosage is 0.0001-200 mg/kg body weight per day, the preferred dosage is 0.01-100 mg/kg body weight per day, and the optimum dosage is 0.1-50 mg/kg body weight per day. At the same time, the optimal dosage depends on the individual. Usually, the dosage may be small at the beginning, and the amount is gradually increased then.

The examples and preparations provided in the present disclosure further illustrate and exemplify the compound of the present disclosure and methods for preparing the same. It is to be understood that the following preparations and examples are not intended to limit the scope of the disclosure in any way.

The following synthetic scheme describes the method for preparing the compound of Formula I in the present disclosure. All the starting materials, reagents, catalysts, solvents and the like used in the synthesis schemes below may be prepared by methods well known to one ordinary skilled in the art of organic chemistry or may be commercially available. All of the final derivatives of the present disclosure may be prepared by methods described in the schemes or analogous methods which are well known to one ordinary skilled in the art of organic chemistry. All variables that are used in these schematics are as defined below or as defined in the claims.

Preparing Method:

The following groups are defined as above. In addition, all of the compound of formula I and the involving intermediates can be purified by conventional separation methods such as extraction, recrystallization, separation by silica gel column chromatography. The 200-300 meshes silica gel and thin layer chromatography silica gel plates used were all produced by Qingdao Haiyang Chemical Co. Ltd. The chemical reagents used were analytically pure or chemically pure commercial products of general reagents, and were used without further purification.

(a) Key Intermediate II may be prepared by a following exemplary synthetic method.

At room temperature, II-2 was obtained by reaction of a self-made or commercially available II-1 and MsCl at room temperature by base catalysis. Under reflux conditions, II-2 was reacted with the self-made II-3 by nucleophilic substitution under base catalysis to give 11-4. Subsequently, under conditions of heating, II-4 and halogenated compound II-5 were subjected to a basic catalysis to prepare the key intermediate II (see in Scheme 1). The basic catalyst used in the present synthetic route can be triethylamine (TEA), N,N'-diisopropyl ethylamine (DIPEA), potassium carbonate ($K_2CO_3$), cesium carbonate ($Cs_2CO_3$), etc.; the solvent can be dichloromethane ($CH_2Cl_2$), 1,2-dichloroethane, acetonitrile ($CH_3CN$), and N,N'-dimethyl formamide (DMF), etc.

Scheme 1 Synthetic route of key intermediate II

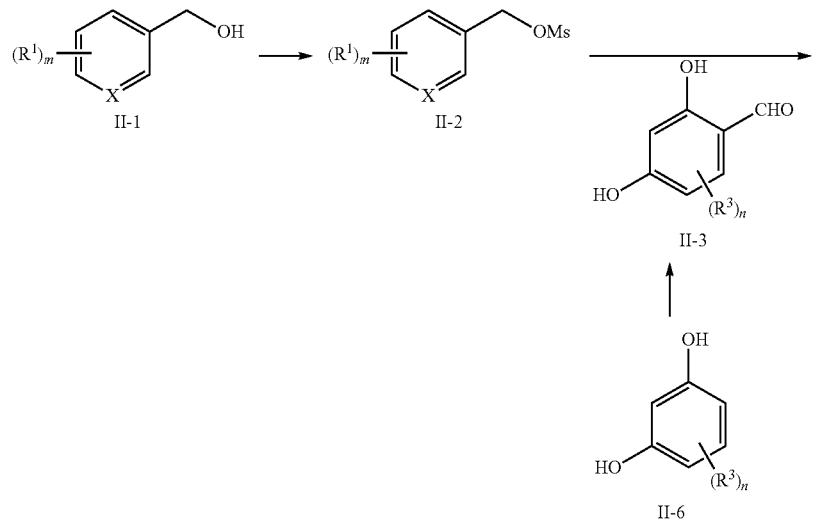

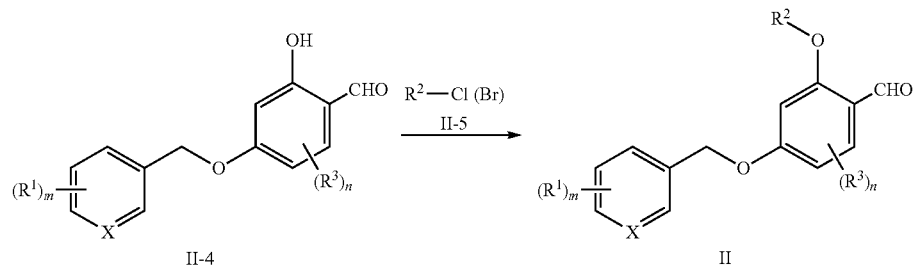

(b) Key Intermediate III can be prepared by the following exemplary synthetic method.

The preparation of the key intermediate III is carried out in a three-stage reaction: 1) under basic catalysis, III protected by a commercially available t-butyloxycarbonyl (Boc) was used as the starting material to form an active intermediate with carbonyl diimidazole (CDI). The reaction was carried out at the temperature from 0° C. to room temperature for 30-60 min. 2) At room temperature, another substrate A III-2 was added to the above reaction solution, continuously stirred for 3-5 h, and the reaction solution was concentrated to obtain a sticky liquid. 3) After dissolving the liquid with a solvent, the target intermediate was obtained by removing the Boc protecting group by acid catalysis (see Scheme 2). The basic catalyst used in the present route may be TEA, DIPEA, etc.; the acid catalyst may be concentrated hydrochloric acid (concentrated HCl), trifluoroacetic acid (TFA), and acetic acid (HOAc), etc.; and the solvent may be $CH_2Cl_2$, methanol ($CH_3OH$), and $CH_3CN$, etc.

(c) The structural formula I of the present disclosure can be prepared by the following exemplary synthetic method.

The above intermediates II and III were subjected to a reductive amination reaction at room temperature to prepare the compound of Formula I in the present disclosure (see in Scheme 3). The reductant used in the present route may be sodium borohydride ($NaBH_4$), sodium cyanoborohydride ($NaBH_3CN$), sodium acetoxyborohydride ($NaBH_3OAc$), etc.; the basic catalyst may be TEA, DIPEA, etc.; the desiccant may be anhydrous magnesium sulfate ($MgSO_4$), anhydrous sodium sulfate ($Na_2SO_4$), molecular sieves, etc.; and the solvent may be $CH_3OH$, $CH_2Cl_2$, 1,2-dichloroethane, etc.

Scheme 3 Synthetic route of compound I

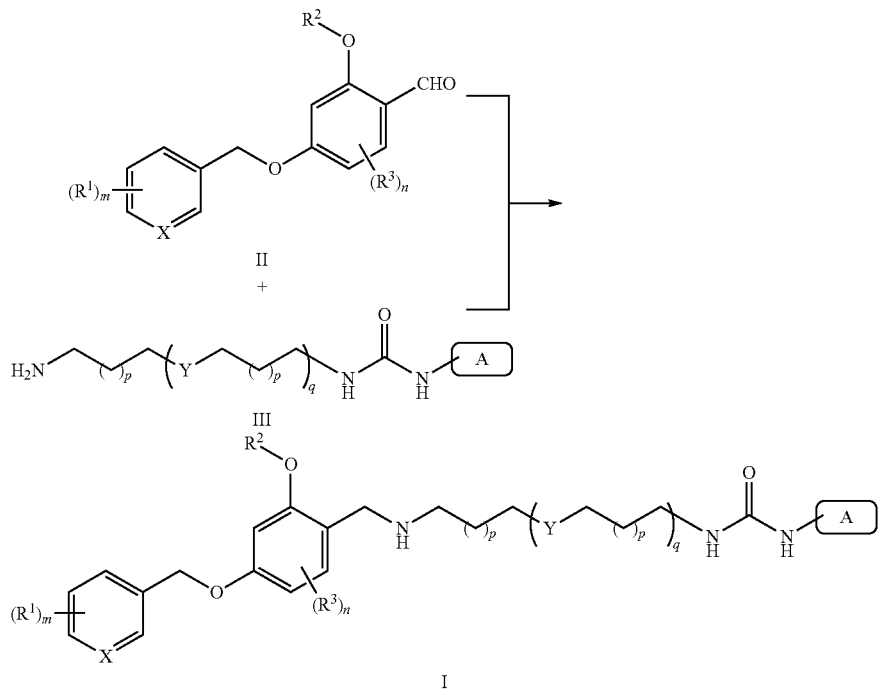

Scheme 2 Synthetic route of key intermediate III

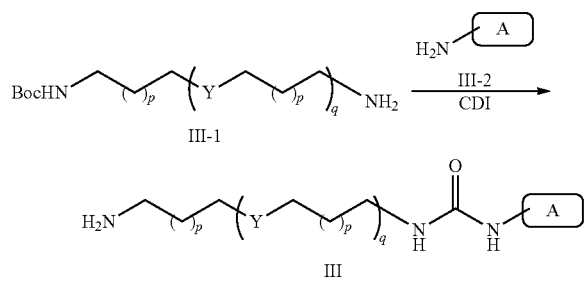

LC-MS Analysis Method:

Mass spectrum conditions: instrument waters ZQ4000; ion source $ES^+$; cone voltage 40V; capillary voltage 3.5 KV; source temperature 120° C.; desolvation gas temperature 350° C.; and cone gas flow 60 L/h.

Chromatography conditions: instrument waters 2695; detector waters 2996 (evaporative light scattering detector); chromatographic column Shimadzu Shim-pack VP-ODS 5 μm 2.0×150 mm; flow rate 0.3 mL/min; column temperature 35° C.; mobile phase $CH_3OH/H_2O/HOAc$ (70/30/0.5).

HPLC analysis method: instrument Shimadzu LC-2010A HT (UV detector); chromatographic column Thermo ODS-2HYPERSIL 5 μm 4.6×150 mm; detection wavelength 230 nM; flow rate 0.7 mL/min; column temperature 25° C.; mobile phase A $CH_3OH/H_2O/HOAc/TEA$ (65/35/0.1/0.2), mobile phase B $CH_3OH/H_2O/HOAc/TEA$ (80/20/0.1/0.2) and mobile phase C $CH_3OH/H_2O/HOAc/TEA$ (50/50/0.1/0.2).

Representative compounds I-1 to I-14 (see Table 2) were prepared according to the procedures described above.

TABLE 2

Typical compounds I-1 to I-14 in the present disclosure

| Compound (Example) | Structural Formula | % Purity (HPLC) | Retention Time min (HPLC) |
|---|---|---|---|
| I-1 (7) | | 97.8 (mobile phase A) | 35.587 |
| I-2 (8) | | 94.8 (mobile phase A) | 25.720 |
| I-3 (9) | | 91.2 (mobile phase B) | 18.720 |
| I-4 (19) | | 94.0 (mobile phase A) | 8.253 |

TABLE 2-continued
Typical compounds I-1 to I-14 in the present disclosure
| Compound (Example) | Structural Formula | % Purity (HPLC) | Retention Time min (HPLC) |
|---|---|---|---|
| I-5 (21) | 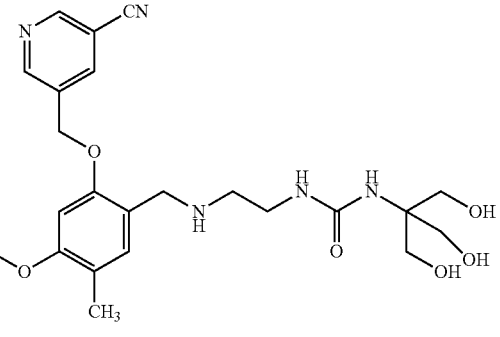 | 95.5 (mobile phase A) | 4.893 |
| I-6 (23) | 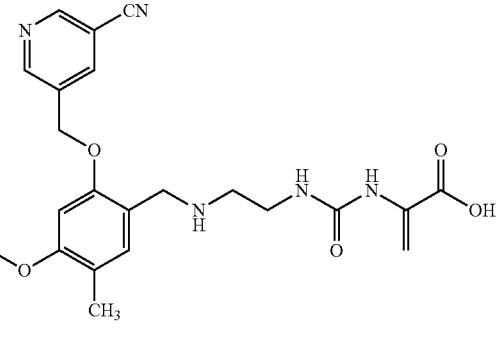 | 83.5 (mobile phase B) | 3.373 |
| I-7 (25) | 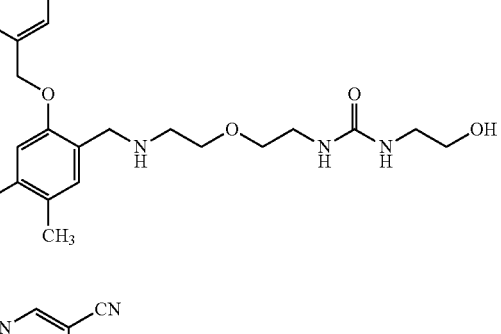 | 91.9 (mobile phase A) | 7.920 |
| I-8 (30) | 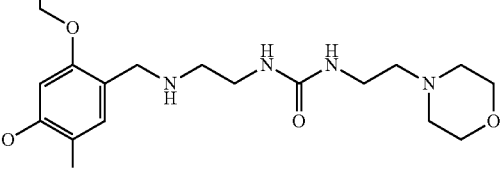 | 92.7 (mobile phase A) | 10.693 |

TABLE 2-continued

Typical compounds I-1 to I-14 in the present disclosure

| Compound (Example) | Structural Formula | % Purity (HPLC) | Retention Time min (HPLC) |
|---|---|---|---|
| I-9 (31) | | 95.3 (mobile phase A) | 7.373 |
| I-10 (32) | | 91.0 (mobile phase A) | 11.213 |
| I-11 (33) | | 81.6 (mobile phase A) | 12.533 |
| I-12 (34) | | 98.4 (mobile phase A) | 7.720 |

TABLE 2-continued

Typical compounds I-1 to I-14 in the present disclosure

| Compound (Example) | Structural Formula | % Purity (HPLC) | Retention Time min (HPLC) |
|---|---|---|---|
| I-13 (37) | | 98.5 (mobile phase C) | 49.747 |
| I-14 (42) | | 89.3 (mobile phase A) | 9.293 |

The present disclosure is further illustrated by the following specific examples, but the scope of protection of the present disclosure is not limited to these examples. The percentages stated in the present disclosure are all percentages by weight unless otherwise specified. The range of values described in the specification, such as units of measure, reaction conditions, physical state of the compound or percentage, are intended to provide an unambiguous written reference. It is still possible for one ordinary skilled in the art to use the temperature, concentration, amount, number of carbon atoms, etc. outside of this range or different from a single value in the implementation of the present disclosure, and it is still possible to obtain the desired result.

Example 1 Preparation of intermediate (2-methyl-(1,1'-diphenyl)-3-yl)methyl Methanesulfonate IIa-2

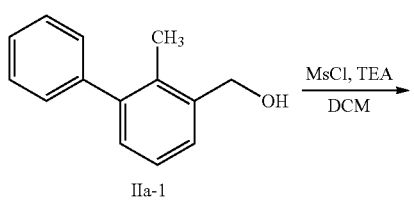

Commercially available IIa-1 (2.37 g, 12.0 mmol, 1.0 equivalent weight) and TEA (3.3 mL, 24 mmol, 2.0 equivalent weight) were dissolved in DCM (40 mL). In an ice bath, MsCl (1.4 mL, 18.0 mmol, 1.5 equivalent weight) was slowly added dropwise into the reaction mixture. After the dropping was completed, the temperature was raised to room temperature, and the reaction was continued for 6 h. The end of the reaction was detected by TLC test. The reaction mixture was diluted with DCM (40 mL), and extracted with water. The organic phase was combined and washed with water (40 mL×2), washed with saturated NaCl solution (40 mL×2), and dried with anhydrous MgSO$_4$. The organic phase was concentrated. After the crude product was separated by column chromatography, to give 3.50 g oily IIa-2, which was directly used for the next reaction (the yield was calculated based on 100%)

Example 2 Preparation of Intermediate 2-hydroxy-4-(2-methyl-(1,1'-diphenyl)-3-yl-methoxy) Benzaldehyde IIa-4

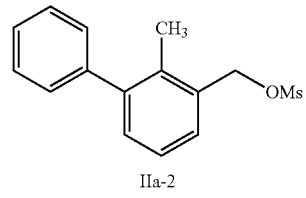 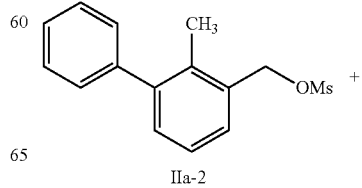

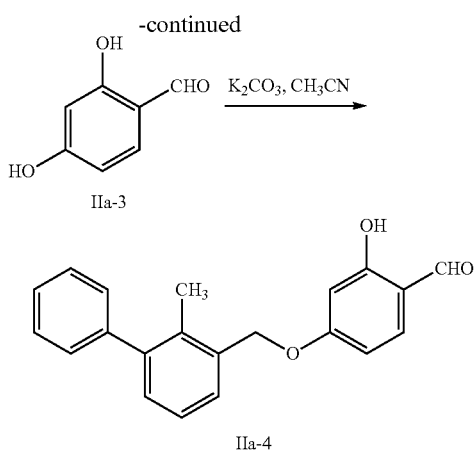

IIa-2 (3.50 g, 12.0 mmol, 1.0 equivalent weight), commercially available IIa-3 (1.65 g, 12.0 mmol, 1.0 equivalent weight) and K$_2$CO$_3$ (1.65 g, 12.0 mmol, 1.0 equivalent weight) were respectively weighted and dissolved in CH$_3$CN (60 mL). After heating and refluxing for 6 h, K$_2$CO$_3$ (0.50 g, 3.6 mmol, 0.3 equivalent weight) was supplemented, and reflux was continued for 5 h. The end of the reaction was detected by TLC test. The reaction mixture was cooled to room temperature, and diluted with ethyl acetate (EtOAc 80 mL). The organic phase was combined and washed with water (40 mL×2), washed with saturated NaCl solution (40 mL×2), and dried with anhydrous MgSO$_4$. The organic phase was concentrated. The crude product was separated by column chromatography to give the product 2.2 g IIa-4, which was directly used for the next reaction (the yield was 57.6%).

LC-MS MS-ESI (m/z) 319.3 [M+H]$^+$, 341.2 [M+Na]$^+$.

Example 3 Preparation of Intermediate 2-(3-cyanobenzyloxy)-4-(2-methyl-(1,1'-diphenyl)-3-yl-methoxyl) Benzaldehyde IIa

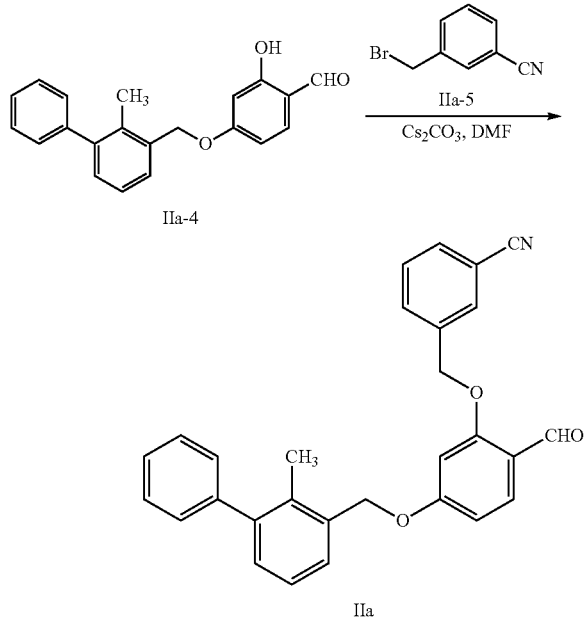

IIa-4 (1.60 g, 5.0 mmol, 1.0 equivalent weight), IIa-5 (1.20 g, 6.0 mmol, 1.2 equivalent weight) and Cs$_2$CO$_3$ (4.90 g, 15.0 mmol, 3.0 equivalent weight) were respectively weighted and dissolved in dry DMF (50 mL), and heated to 80° C. to react for 3 h. The end of the reaction was detected by TLC test. The reaction mixture was diluted with water, and extracted with DCM/CH$_3$OH (10 mL/180 mL). The organic phase was combined and washed with water (40 mL×2), washed with saturated NaCl solution (40 mL×2), and dried with anhydrous MgSO$_4$. The organic phase was concentrated. The crude product was separated by column chromatography to give 1.00 g white solid IIa was obtained (the yield was 48.9%).

$^1$H-NMR (400 MHz, DMSO-d$_6$) δ ppm 10.27 (s, 1H), 8.01 (s, 1H), 7.84 (m, 2H), 7.73 (d, 1H, J=8.6 Hz), 7.63 (m, 1H), 7.46 (m, 3H), 7.37 (m, 1H), 7.30 (m, 3H), 7.22 (m, 1H), 6.96 (s, 1H), 6.84 (m, 1H), 5.36 (s, 2H), 5.27 (s, 2H), 2.20 (s, 3H).

Example 4 Preparation of Intermediate Hydrochloride of 1-(2-aminoethyl)-3-(2-N-morpholine)ethyl) urea IIIa

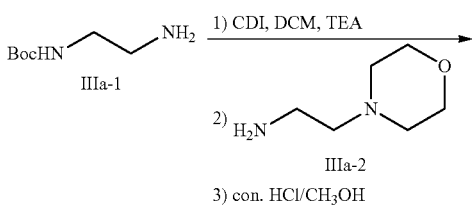

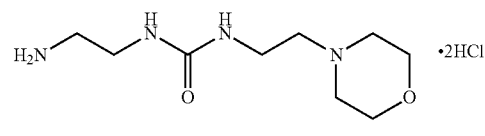

IIa-1 (0.32 g, 2.0 mmol, 1.0 equivalent weight) and TEA (0.85 mL, 6.0 mmol, 3.0 equivalent weight) were dissolved in DCM (20 mL). In an ice bath, CDI (0.34 g, 2.1 mmol, 1.1 equivalent weight) was added and stirred for 10 min, and then the mixture was heated to room temperature and stirring was continued for 30 min. Subsequently, at room temperature, the IIIa-2 (0.26 g, 2.0 mmol, 1.0 equivalent weight) was added dropwise into the above reaction solution, and stirring was continued for 3 h. The solvent was concentrated to obtain a sticky liquid. Finally, the sticky liquid was dissolved in methanol (10 mL), and concentrated hydrochloric acid (con. HCl, 2 mL) was added dropwise into the reaction mixture, which was subjected to heating and refluxing for 2 h. The solvent was concentrated to obtain a colorless and transparent sticky liquid IIIa 1.00 g. The crude product was used in the next reaction without separation (the yield was calculated as 100%)

LC-MS MS-ESI (m/z) 217.1 [M+H]+, 239.1 [M+Na]+.

Example 5 Preparation of Intermediate Hydrochloride of 1-(2-aminoethyl)-3-(2-hydroxyethyl) Urea IIIb LC-MS MS-ESI (m/z) 148.2 [M+H]+, 170.2 [M+Na]+.

Example 6 Preparation of Intermediate Hydrochloride of 1-(2-aminoethyl)-3-(2-tert-butyl-O-tert-butyl-L-serinate-2-yl)urea IIIb

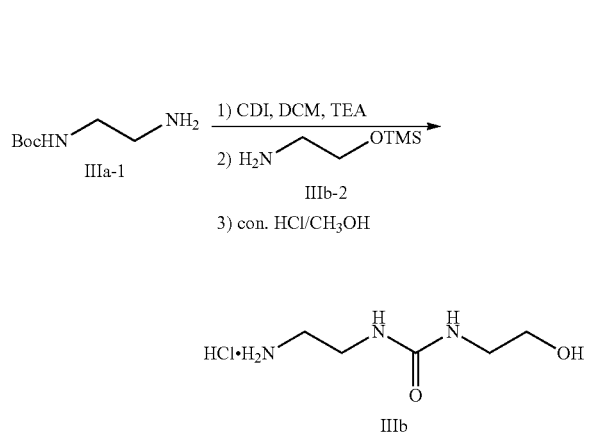

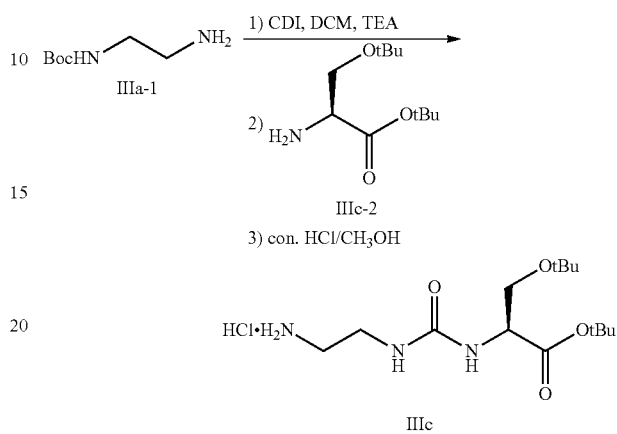

IIIa-1 (1.60 g, 10.0 mmol, 1.0 equivalent weight) and TEA (2.8 mL, 20.0 mmol, 2.0 equivalent weight) were dissolved in DCM (40 mL). In an ice bath, CDI (1.70 g, 10.1 mmol, 1.1 equivalent weight) was added and stirred for 10 min, and then the mixture was heated to room temperature and stirring was continued for 30 min. Subsequently, at room temperature, the IIIb-2 (1.33 g, 10.0 mmol, 1.0 equivalent weight) was added dropwise into the above reaction solution, and stirring was continued for 3 h. The solvent was concentrated to obtain a sticky liquid. Finally, the sticky liquid was dissolved in methanol (10 mL), and concentrated hydrochloric acid (con. HCl, 2 mL) was added dropwise into the reaction mixture, which was subjected to heating and refluxing for 2 h. The solvent was concentrated to obtain a colorless and transparent sticky liquid IIIb 4.00 g. The crude product was used in the next reaction without separation (the yield was calculated based on 100%).

IIIa-1 (0.32 g, 2.0 mmol, 1.0 equivalent weight) and TEA (0.85 mL, 6.0 mmol, 3.0 equivalent weight) were dissolved in DCM (20 mL). In an ice bath, CDI (0.34 g, 2.1 mmol, 1.1 equivalent weight) was added and stirred for 10 min, and then the mixture was heated to room temperature and stirring was continued for 30 min. Subsequently, at room temperature, the IIIc-2 (0.43 g, 2.0 mmol, 1.0 equivalent weight) was added dropwise into the above reaction solution, and stirring was continued for 3 h. The solvent was concentrated to obtain a sticky liquid. Finally, the sticky liquid was dissolved in methanol (10 mL), and concentrated hydrochloric acid (con. HCl, 2 mL) was added dropwise into the reaction mixture, and subjected to heating and refluxing for 2 h. The solvent was concentrated to obtain a colorless and transparent sticky liquid IIIc 1.00 g. The crude product was used in the next reaction without separation (the yield was calculated based on 100%).

Example 7 Preparation of Compound 1-((2-(2-(3-cyanophenyl)methoxy-4-(2-methyl-(1,1'-diphenyl)-3-yl-methoxy))benzylamino)-2-ethyl)-3-(2-(N-morpholine)ethyl)urea I-1

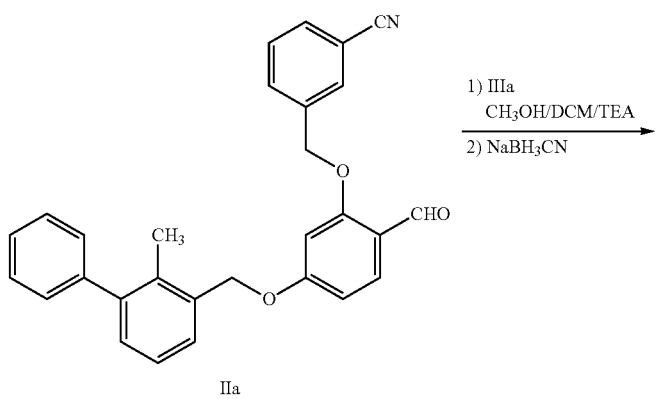

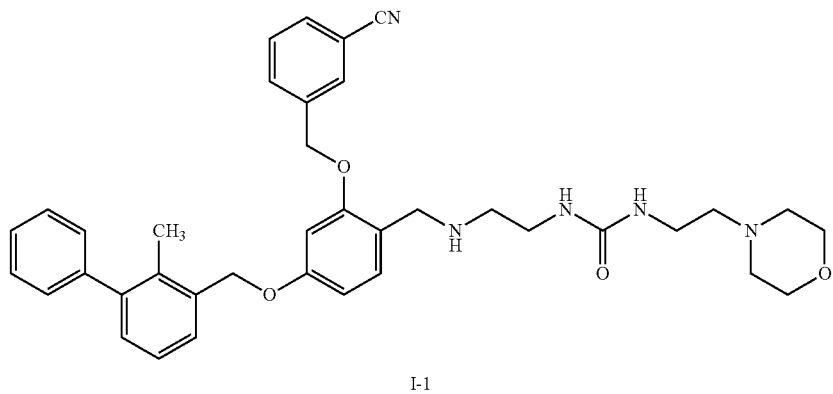

I-1

IIa (0.04 g, 0.1 mmol, 1.0 equivalent weight) and the crude product of IIIa (0.25 g, 0.5 mmol, 5.0 equivalent weight) were respectively weighted and dissolved in a mixed solution of $CH_3OH/DCM$ (15 mL/2 mL), and TEA (2 mL) was added dropwise, and then anhydrous $MgSO_4$ (1.00 g) was added. The mixture was stirred over night at room temperature, and $NaBH_3CN$ (0.06 g, 1.0 mmol, 10.0 equivalent weight) was added, and the stirring was continued for 2 h. The end of the reaction was detected by LC-MS test. The reaction mixture was diluted with DCM (20 mL), and extracted with water. The organic phase was combined and washed with water (40 mL×2), washed with saturated NaCl solution (40 mL×2), and dried with anhydrous $MgSO_4$. The organic phase was concentrated. The crude product was purified by TLC (developing solvent: DCM/CH3OH 7/1) to obtain 5.4 mg light yellow solid I-1 (the yield was 8.5%). LC-MS MS-ESI (m/z) 634.8 $[M+H]^+$, 656.8 $[M+Na]+$, Example 8 Preparation of Compound 1-((2-(2-(3-cyanophenyl)methoxy-4-(2-methyl-(1,1'-diphenyl)-3-yl-methoxy))benzylamino)-2-ethyl)-3-(2-hydroxyethyl)urea I-2

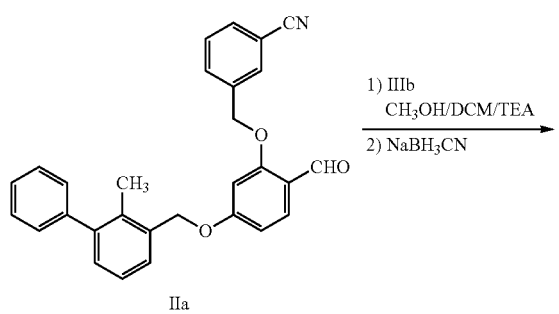

IIa

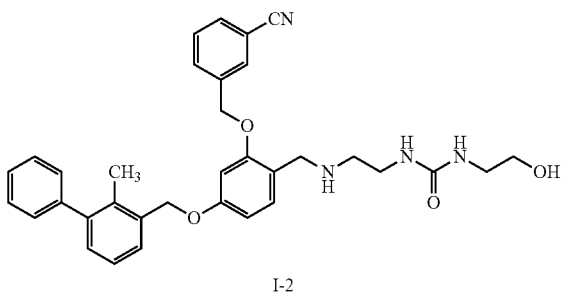

I-2

IIa (0.09 g, 0.2 mmol, 1.0 equivalent weight) and the crude product of IIIb(0.20 mg, 0.5 mmol, 2.5 equivalent weight) were respectively weighted and dissolved in a mixed solution of $CH_3OH/DCM$ (15 mL/2 mL), and TEA (2 mL) was added dropwise, and then anhydrous $MgSO_4$ (1.00 g) was added. The mixture was stirred over night at room temperature, and $NaBH_3CN$ (0.06 g, 1.0 mmol, 10.0 equivalent weight) was added, and the stirring was continued for 2 h. The end of the reaction was detected by LC-MS test. The reaction mixture was diluted with DCM (20 mL), and extracted with water. The organic phase was combined and washed with water (40 mL×2), washed with saturated NaCl solution (40 mL×2), and dried with anhydrous $MgSO_4$. The organic phase was concentrated. The crude product was purified by TLC (developing solvent: DCM/CH3OH 7/1) to obtain 6.0 mg light yellow solid I-2 (the yield was 5.3%).

LC-MS MS-ESI (m/z) 565.8 $[M+H]^+$, 587.7 $[M+Na]^+$. $^1$H-NMR (400 MHz, DMSO-$d_6$) δ ppm 8.00 (s, 1H), 7.87 (m, 1H), 7.82 (m, 1H), 7.63 (m, 1H), 7.36-7.48 (m, 5H), 7.25-7.29 (m, 3H), 7.19-7.21 (m, 1H), 6.85 (s, 1H), 6.75-6.77 (m, 1H), 6.35 (t, 1H, J=5.4 Hz), 6.24 (t, 1H, J=5.4 Hz), 5.27 (s, 2H), 5.16 (s, 2H), 4.65 (t, 1H, J=5.0 Hz), 4.12 (s, 2H), 3.36 (m, 1H), 3.25 (m, 2H), 3.04 (m, 2H), 2.95 (m, 2H), 2.18 (s, 3H).

Example 9 Preparation of Compound 1-((2-(2-(3-cyanophenyl)methoxy-4-(2-methyl-(1,1'-diphenyl)-3-yl-methoxy))benzylamino)-2-ethyl)-3-(2-tert-butyl-O-tert-butyl-L-serinate-2-yl)urea I-3

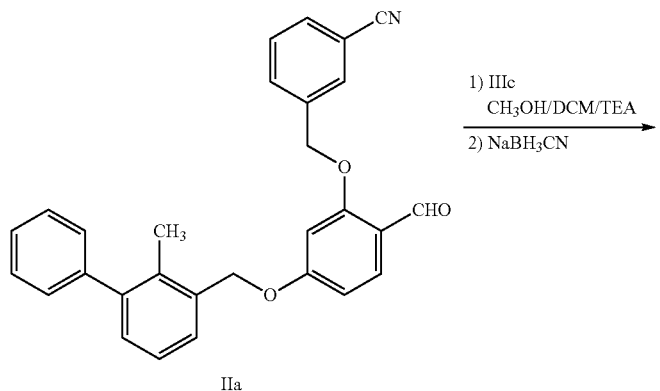

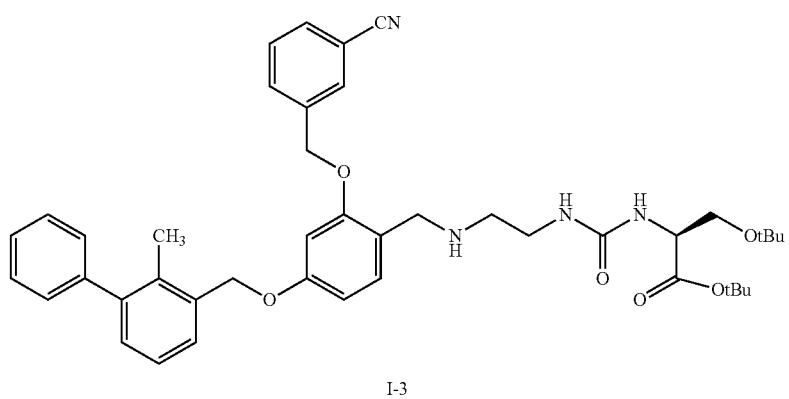

IIa (0.22 g, 0.5 mmol, 1.0 equivalent weight) and the crude product of IIIc (0.60 g, 1.0 mmol, 2.0 equivalent weight) were respectively weighted and dissolved in a mixed solution of CH$_3$OH/DCM (15 mL/2 mL), and TEA (2 mL) was added dropwise, and then anhydrous MgSO$_4$ (1.00 g) was added. The mixture was stirred over night at room temperature, and NaBH$_3$CN (0.13 g, 2.0 mmol, 4.0 equivalent weight) was added, and the stirring was continued for 2 h. The end of the reaction was detected by LC-MS test. The reaction mixture was diluted with DCM (20 mL), and extracted with water. The organic phase was combined and washed with water (40 mL×2), washed with saturated NaCl solution (40 mL×2), and dried with anhydrous MgSO$_4$. The organic phase was concentrated. The crude product was purified by TLC (developing solvent: DCM/CH$_3$OH 10/1) to obtain 15.0 mg light yellow solid I-3 (the yield was 4.1%).

LC-MS MS-ESI (m/z) 721.8 [M+H]$^+$, 743.8 [M+Na]$^+$.

Example 10 Preparation of Intermediate Methyl 2-cyano-3-chlorobenzoate IIb-1-2

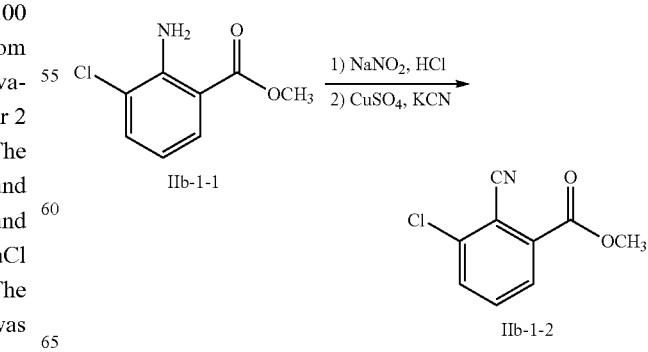

In an ice bath, con. HCl (30 mL) was added into a water (120 mL) solution of IIb-1-1 (10.00 g, 54.1 mmol, 1.0 equivalent weight). In the ice bath, water (120 mL) solution of NaNO$_2$ (8.30 g, 120.0 mmol, 2.2 equivalent weight) was added into the above solution within 15 min. After the dropping was completed, the stirring was continued for 1 h. Then the pH was neutralized to 6-7 with aq. Na$_2$CO$_3$ to obtain a diazonium salt reaction mixture, which was kept at a low temperature. In addition, at room temperature, a blue water (120 mL) solution of CuSO$_4$.5H$_2$O (15.00 g, 60.0 mmol, 1.1 equivalent weight) was prepared. Methylbenzene was added to the reaction solution, which was then cooled to 0° C. Then KCN (14.70 g, 225.0 mmol, 4.2 equivalent weight) was added, and the reaction solution turned brown. The mixture was heated to 60° C., and the prepared diazonium salt was added into the brown reaction solution within 15 min, and the mixture was heated to 70° C., and stirred for 1 h. The end of the reaction was detected by TLC test. The reaction solution was diluted with EtOAc, and suction filtration was carried out using diatomite. The organic phase was combined and washed with water (100 mL×2), washed with saturated NaCl solution (100 mL×2), and dried with anhydrous Na$_2$SO$_4$. The organic phase was concentrated. The crude product was separated and purified by column chromatography, to obtain 10.00 g solid IIb-1-2 (the yield was 95%).

$^1$H-NMR (400 MHz, CDCl$_3$) δ ppm 8.04 (d, 1H, J=7.6 Hz), 7.74 (d, 1H, J=8.0 Hz), 7.63 (d, 1H, J=8.0 Hz), 4.02 (s, 3H).

Example 11 Preparation of Intermediate 2-chloro-6-(hydroxymethyl)benzonitrile IIb-1-3

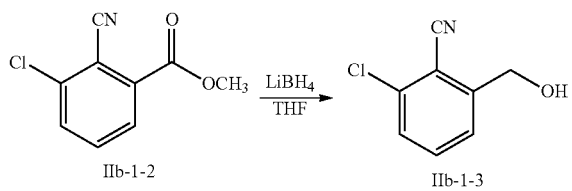 [SMILES: COC(=O)c1cccc(Cl)c1C#N ; "LiBH4" ; N#Cc1c(Cl)cccc1CO ; "THF"]

At −40° C., LiBH4 (1.10 g, 49.0 mmol, 2.0 equivalent weight) was added to IIb-1-2 (4.80 g, 24.5 mmol, 1.0 equivalent weight) in a THF (150 mL) solution in batches. Then the mixture was heated to room temperature, and stirred overnight. The end of the reaction was detected by TLC test. The reaction was quenched with saturated NH$_4$Cl, and extracted with DCM. The organic phase was combined and washed with 1.5N HCl (100 mL×2), washed with saturated NaCl solution (100 mL×2), and dried with anhydrous Na$_2$SO$_4$. The crude product was recrystallized with DCM/PE, to obtain 3.50 g solid IIb-1-3 (the yield was 85%) LC-MS MS-ESI (m/z) 168.0 [M+H]$^+$.

Example 12 Preparation of Intermediate 2-(2,3-dihydrobenzo[b][1,4-dioxin-6-yl])-6-(hydroxymethyl)benzonitrile IIb-1

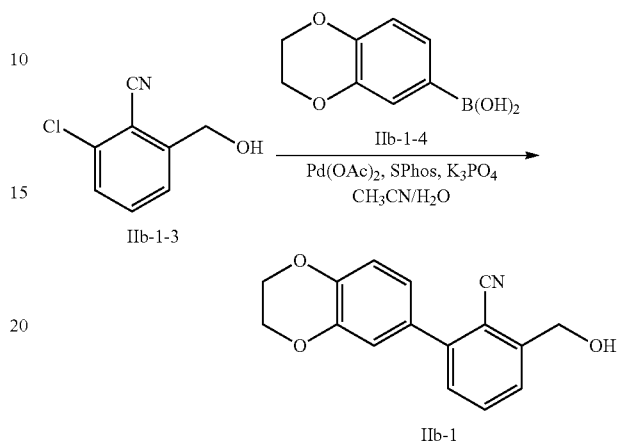

IIb-1-3 (0.50 g, 3.0 mmol, 1.0 equivalent weight), IIb-1-4 (0.65 g, 3.6 mmol, 1.2 equivalent weight), Pd(OAc)$_2$ (0.13 g, 0.60 mmol, 0.2 equivalent weight), SPhos (0.61 g, 1.5 mmol, 0.5 equivalent weight) and K$_3$PO$_4$ (1.27 g, 6.0 mmol, 2 equivalent weight) were respectively weighted and dissolved in a mixed solvent of CH$_3$CN/H$_2$O (10/1, 20 mL). The mixture was subjected to refluxing for 2 h with the protection of argon. The end of the reaction was detected by TLC test. The reaction mixture was concentrated. The crude product was separated and purified by column chromatography, to obtain 0.40 g solid IIb-1 (the yield was 50%).

$^1$H-NMR (400 MHz, CDCl$_3$) δ ppm 7.59-7.61 (m, 2H), 7.39 (d, 1H, J=7.2 Hz), 7.02-7.05 (m, 2H), 6.97 (d, 1H, J=8.0 Hz), 4.98 (d, 1H, J=5.2 Hz), 4.31 (s, 4H), 2.11 (s, 1H).

Example 13 Preparation of Intermediate 2-cyano-3-(2,3-dihydrobenzo[b][1,4-dioxin-6-yl]) Benzylmethanesulfonate IIb-2

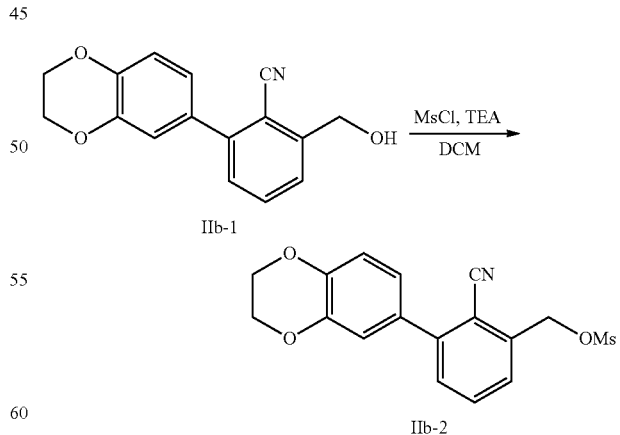

IIb-1 (0.63 g, 2.4 mmol, 1.0 equivalent weight) and TEA (0.3 mL, 2.4 mmol, 1.0 equivalent weight) were respectively weighted and dissolved in DCM (20 mL). In an ice bath, MsCl (0.18 mL, 18.0 mmol, 1 equivalent weight) was slowly added dropwise into the reaction mixture. After the dropping was completed, the temperature was raised to room temperature, and the reaction went on for 1 h. The end of the reaction was detected by TLC test. The reaction mixture was concentrated. The crude product was separated and purified by column chromatography, to obtain 0.80 g solid IIb-2 (the yield was 98%).

Example 14 Preparation of Intermediate 2,4-dihydroxy-5-methylbenzaldehyde IIb-3

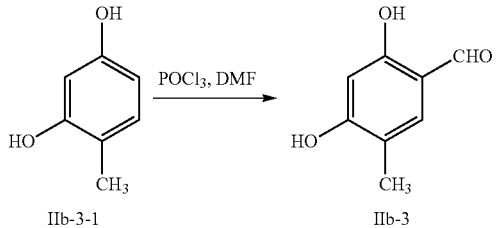

At 0° C., POCl₃ (1.8 mL) was added dropwise into DMF (50 mL). IIb-3-1 (1.00 g, 8.1 mmol, 1 equivalent weight) were weighed and dissolved in DMF (10 mL), and then the resultant was added dropwise into the above DMF solution. The mixture was slowly heated to room temperature, and stirred for 3 h. The end of the reaction was detected by TLC test. The reaction mixture was poured into water, and extracted with EtOAc. The organic phase was combined and washed with water (40 mL×2), washed with saturated NaCl solution (40 mL×2), and dried with anhydrous Na₂SO₄. The organic phase was concentrated. The crude product was separated and purified by column chromatography (eluent: PE/EtOAc 40/1-30/1), to obtain 0.41 g yellow solid IIb-3 (the yield was calculated based on 33%).

¹H-NMR (400 MHz, CDCl₃) δ ppm 11.27 (s, 1H), 9.68 (s, 1H), 6.35 (s, 1H), 5.81 (s, 1H), 2.21 (s, 3H).

Example 15 Preparation of Intermediate 2-hydroxy-4-(2-cyano-3-(2,3-dihydrobenzo[b][1,4-dioxin-6-yl])benzyloxy)-5-methylbenzaldehyde IIb-4

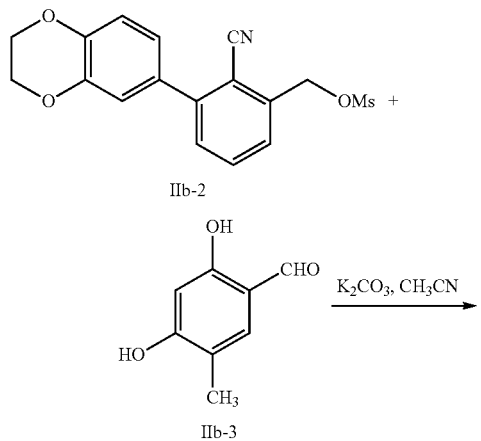

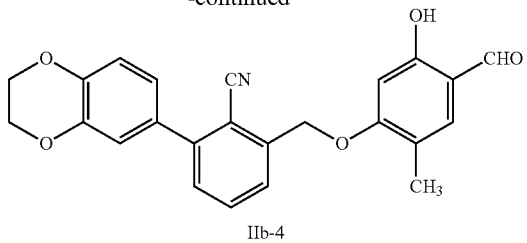

IIb-2 (0.18 g, 0.5 mmol, 1.0 equivalent weight), IIb-3 (0.07 g, 0.46 mmol, 0.9 equivalent weight) and K₂CO₃ (0.07 g, 0.5 mmol, 1 equivalent weight) were respectively weighed and dissolved in CH3CN. The mixture was subjected to refluxing and stirred overnight. The end of the reaction was detected by TLC test. The reaction mixture was concentrated. The crude product was separated and purified by column chromatography (eluent: PE/EtOAc 10/1-3/1), to obtain 0.11 g solid IIb-4 (the yield was 54%).

Example 16 Preparation of Intermediate 5-(hydroxymethyl)-3-cyanopyridine IIb-5-2

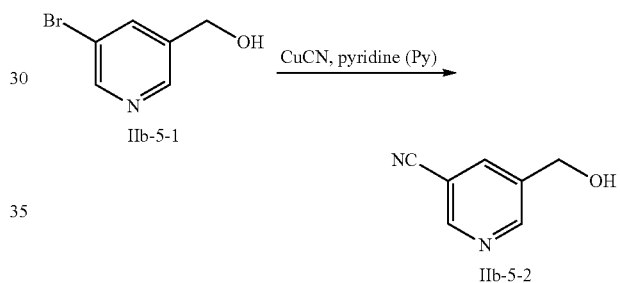

The IIb-5-1 (5.00 g, 26.5 mmol, 1.0 equivalent weight) and CuCN (6.00 g, 65.0 mmol, 2.5 equivalent weight) were respectively weighted and dissolved in Py, and the mixture was disposed in a sealed tube and heated to 165° C. After reacting for 48 h, the end of the reaction was detected by TLC test. The reaction mixture was cooled to room temperature, diluted with aq. NH₃ and aq. NH₄Cl, and extracted with CHCl₃ (150 mL×3). The organic phase was combined and washed with water (100 mL×2), washed with saturated NaCl solution (100 mL×2), and dried with anhydrous Na₂SO₄. The organic phase was concentrated. The crude product was separated and purified by column chromatography, to obtain 1.50 g solid IIb-5-2 (the yield was 42%).

¹H-NMR (400 MHz, CDCl₃) δ ppm 8.81 (s, 1H), 8.80 (s, 1H), 8.03 (s, 1H), 4.83 (s, 2H).

Example 17 Preparation of Intermediate 5-(chloromethyl)-3-cyanopyridine IIb-5

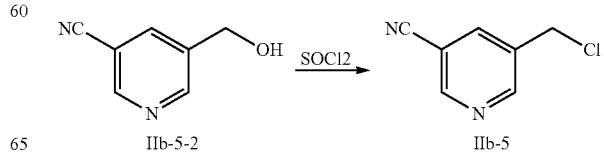

IIb-5-2 (1.50 g, 11.3 mmol, 1.0 equivalent weight) was dissolved in DCM (50 mL), and 4N of dioxane hydrochloride (10 mL) was added. After concentrating the mixture, SOCl$_2$ (10 mL) was added, heated to 60° C. and stirred for 3 h. The end of the reaction was detected by TLC test. The temperature was cooled to room temperature. The reaction solution was concentrated. The crude product was separated and purified by column chromatography, to obtain 0.55 g solid IIb-5 (the yield was 32%).

$^1$H-NMR (400 MHz, CDCl$_3$) δ ppm 8.85 (s, 1H), 8.83 (s, 1H), 8.04 (s, 1H), 4.63 (s, 2H).

Example 18 Preparation of intermediate (2-(5-cyanopyridin-3-yl)methoxy-4-(2-cyano-3-(2,3-dihydrobenzo[b][1,4-dioxin-6-yl])benzyloxy)-5-methyl)benzaldehyde IIb

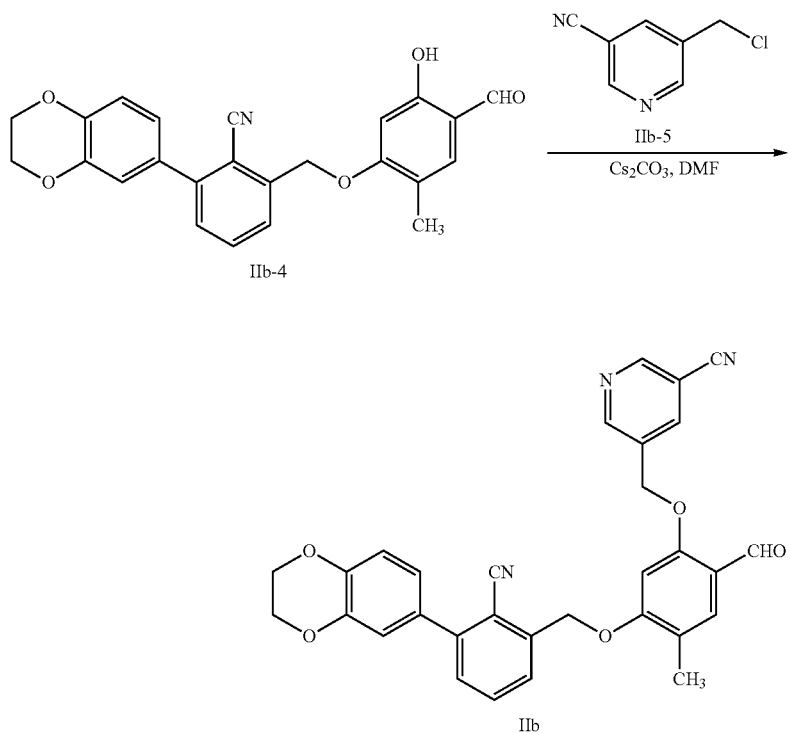 [SMILES: Cc1cc(C=O)c(O)cc1OCc1cccc(-c2ccc3c(c2)OCCO3)c1C#N ; N#Cc1cncc(CCl)c1 ; Cc1cc(C=O)c(OCc2cncc(C#N)c2)cc1OCc1cccc(-c2ccc3c(c2)OCCO3)c1C#N]

IIb-4 (1.00 g, 2.5 mmol, 1.0 equivalent weight), IIb-5 (0.76 g, 5.0 mmol, 2 equivalent weight) and Cs$_2$CO3 (1.22 g, 3.75 mmol, 1.5 equivalent weight) were respectively weighted and dissolved in dry DCM (20 mL), and the mixture was heated to 75° C. and reacted for 2 h. The end of the reaction was detected by TLC test. The temperature was cooled to room temperature. The reaction solution was concentrated. The crude product was separated and purified by column chromatography (eluent: PE/EtOAc 2/1), to obtain 1.00 g solid IIb (the yield was 78%).

LC-MS MS-ESI (m/z) 518.2 [M+H]$^+$, $^1$H-NMR (400 MHz, DMSO-d6) δ ppm 10.27 (s, 1H), 9.02 (s, 2H), 8.53 (s, 1H), 7.71-7.80 (m, 2H), 7.56-7.61 (m, 2H), 7.01-7.11 (m, 4H), 5.47 (s, 2H), 5.45 (s, 2H), 4.31 (s, 4H), 2.12 (s, 3H).

Example 19 Preparation of Compound 1-((2-(2-(5-cyanopyridin-3-yl)methoxy-4-(2-cyano-3-(2,3-dihydrobenzo[b])[1,4-dioxin-6-yl])benzyloxy)-5-methyl)benzylamino)-2-ethyl)-3-(2-hydroxyethyl)urea I-4

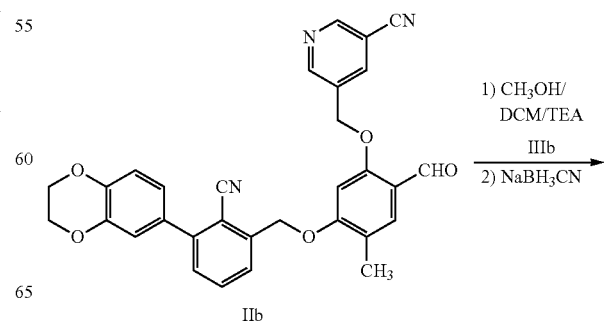

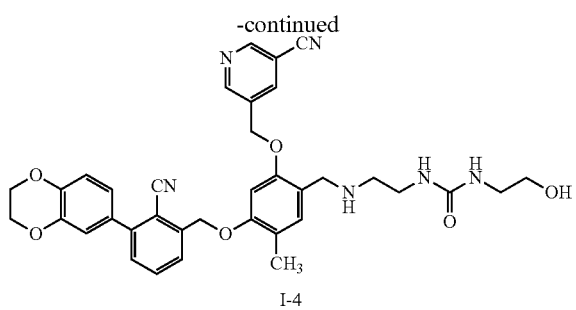

I-4

IIb (0.06 g, 0.12 mmol, 1.0 equivalent weight) and the crude product of IIIb (0.20 g, 0.5 mmol, 4.2 equivalent weight) were respectively weighted and dissolved in a mixed solvent of CH$_3$OH/DCM (15 mL/2 mL), and TEA (2 mL) was added dropwise, and then anhydrous MgSO$_4$ (1.00 g) was added. The mixture was stirred over night at room temperature, and NaBH$_3$CN (0.06 g, 1.0 mmol, 8.3 equivalent weight) was added, and the stirring was continued for 2 h. The end of the reaction was detected by LC-MS test. The reaction mixture was diluted with DCM (20 mL), and extracted with water. The organic phase was combined and washed with water (40 mL×2), washed with saturated NaCl solution (40 mL×2), and dried with anhydrous MgSO$_4$. The organic phase was concentrated. The crude product was purified by preparative TLC (developing solvent: DCM/CH$_3$OH 7/1), to obtain 15.0 mg white solid I-4 (the yield was 19.2%).

LC-MS MS-ESI (m/z) 649.4 [M+H]$^+$, 671.4 [M+Na]$^+$.
$^1$H-NMR (400 MHz, DMSO-d6) δ ppm 9.00-9.03 (m, 2H), 8.49 (s, 1H), 7.75 (m, 1H), 7.67 (m, 1H), 7.57 (m, 1H), 7.26 (s, 1H), 7.10 (s, 1H), 7.02-7.06 (m, 2H), 6.98 (s, 1H), 6.37 (t, 1H, J=5.6 Hz), 6.24 (t, 1H, J=5.6 Hz), 5.35 (s, 4H), 4.65 (m, 1H), 4.31 (s, 4H), 4.10 (s, 2H), 3.26 (m, 2H), 3.00-3.09 (m, 4H), 2.93 (s, 2H), 2.13 (s, 3H).

Example 20 Preparation of Intermediate Hydrochloride of 1-(2-aminoethyl)-3-(1,3-dihydroxy-2-(hydroxymethyl)propan-2-yl)urea IIId

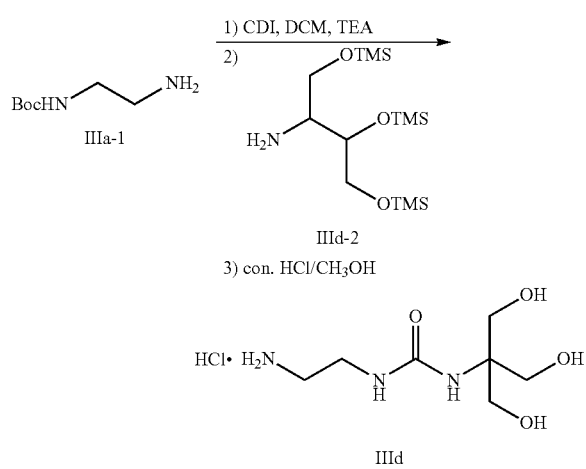

IIIa-1 (0.32 g, 2.0 mmol, 1.0 equivalent weight) and TEA (0.6 mL, 4.0 mmol, 2.0 equivalent weight) were weighed and dissolved in DCM (20 mL). In an ice bath, CDI (0.34 g, 2.1 mmol, 1.1 equivalent weight) was added and stirred for 10 min, and then the mixture was heated to room temperature and stirring was continued for 30 min. Then, at room temperature, the IIIc-2 (0.67 g, 2.0 mmol, 1.0 equivalent weight) was added dropwise into the above reaction solution, and stirring was continued for 3 h. The solvent was concentrated to obtain a sticky liquid. Finally, the sticky liquid was dissolved in methanol (10 mL), and concentrated hydrochloric acid (con. HCl, 2 mL) was added dropwise into the reaction mixture, which was then subjected to heating and refluxing for 2 h. The solvent was concentrated to obtain a colorless and transparent sticky liquid IIId 1.20 g. The crude product was directly used for the next reaction without separation (the yield was calculated based on 100%).

LC-MS MS-ESI (m/z) 208.5 [M+H]$^+$, 230.4 [M+Na]$^+$.

Example 21 Preparation of Compound 1-((2-(2-(5-cyanopyridin-3-yl)methoxy-4-(2-cyano-3-(2,3-dihydrobenzo[b])[1,4-dioxin-6-yl])benzyloxy)-5-methyl)benzylamino)-2-ethyl)-3-(1,3-dihydroxy-2-(hydroxymethyl)propan-2-yl)urea I-5

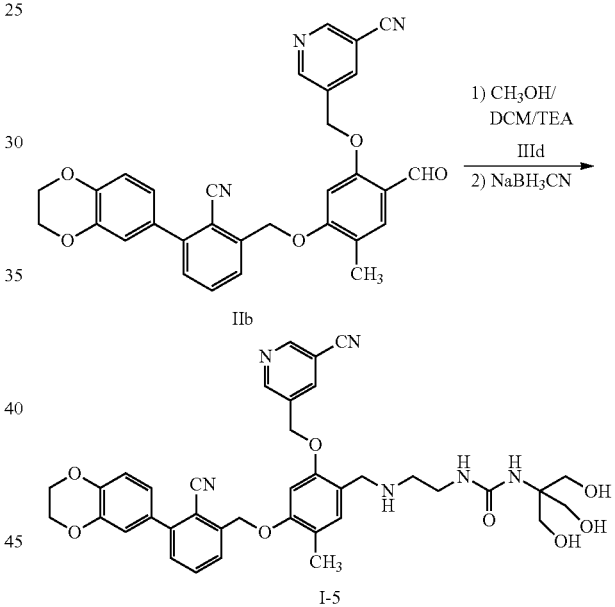

I-5

IIb (0.06 g, 0.12 mmol, 1.0 equivalent weight) and the crude product of IIId (0.30 g, 0.5 mmol, 4.2 equivalent weight) were respectively weighted and dissolved in a mixed solvent of CH$_3$OH/DCM (15 mL/2 mL), and TEA (2 mL) was added dropwise, and then anhydrous MgSO$_4$ (1.00 g) was added. The mixture was stirred over night at room temperature, and NaBH3CN (0.06 g, 1.0 mmol, 8.3 equivalent weight) was added, and the stirring was continued for 2 h. The end of the reaction was detected by LC-MS test. The reaction mixture was diluted with DCM (20 mL), and extracted with water. The organic phase was combined and washed with water (40 mL×2), washed with saturated NaCl solution (40 mL×2), and dried with anhydrous MgSO$_4$. The organic phase was concentrated. The crude product was purified by TLC (developing solvent: DCM/CH$_3$OH 5/1), to obtain 3.1 mg sticky solid I-5 (the yield was 3.6%).

LC-MS MS-ESI (m/z) 709.6 [M+H]+, 731.5 [M+Na]+.

Example 22 Preparation of Intermediate Hydrochloride of 1-(2-aminoethyl)-3-(2-acryl-2-yl)urea IIIe

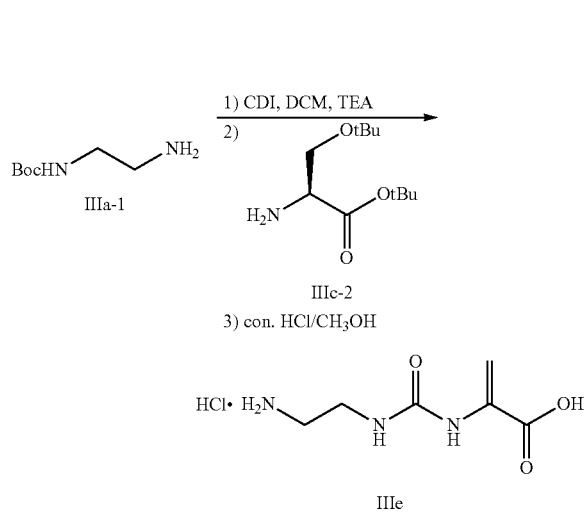

IIIa-1 (0.32 g, 2.0 mmol, 1.0 equivalent weight) and TEA (0.85 mL, 6.0 mmol, 3.0 equivalent weight) were dissolved in DCM (20 mL). In an ice bath, CDI (0.34 g, 2.1 mmol, 1.1 equivalent weight) was added and stirred for 10 min, and then the mixture was heated to room temperature and stirring was continued for 30 min. Then, at room temperature, the IIIc-2 (0.43 g, 2.0 mmol, 1.0 equivalent weight) was added dropwise into the above reaction solution, and stirring was continued for 3 h. The solvent was concentrated to obtain a sticky liquid. Finally, the sticky liquid was dissolved in methanol (10 mL), and concentrated HCl (2 mL) was added dropwise into the reaction mixture, which was then subjected to heating and refluxing for 2 h. The solvent was concentrated to obtain 1.00 g colorless sticky liquid IIIe. The crude product was directly used for the next reaction without separation (the yield was calculated based on 100%).

LC-MS MS-ESI (m/z) 175.05 [M+H]+.

Example 23 Preparation of Compound 1-((2-(2-(5-cyanopyridin-3-yl)methoxy-4-(2-cyano-3-(2,3-dihydrobenzo[b])[1,4-dioxin-6-yl])benzyloxy)-5-methyl)benzylamino)-2-ethyl)-3-(2-acryl-2-yl)urea I-6

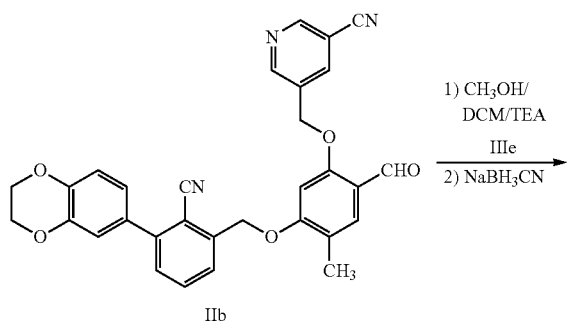

IIb (0.06 g, 0.12 mmol, 1.0 equivalent weight) and the crude product of IIIe (0.25 g, 0.5 mmol, 4.2 equivalent weight) were respectively weighted and dissolved in a mixed solvent of CH3OH/DCM (15 mL/2 mL), and TEA (2 mL) was added dropwise, and then anhydrous MgSO4 (1.00 g) was added. The mixture was stirred over night at room temperature, and NaBH3CN (0.06 g, 1.0 mmol, 8.3 equivalent weight) was added, and the stirring was continued for 2 h. The end of the reaction was detected by LC-MS test. The reaction mixture was diluted with DCM (20 mL), and extracted with water. The organic phase was combined and washed with water (40 mL×2), washed with saturated NaCl solution (40 mL×2), and dried with anhydrous MgSO4. The organic phase was concentrated. The crude product was purified by preparative TLC (developing solvent: DCM/CH3OH 7/1), to obtain 10.0 mg sticky solid I-6 (the yield was 12.4%).

LC-MS MS-ESI (m/z) 675.5 [M+H]+, 697.4 [M+Na]+.

Example 24 Preparation of Intermediate Hydrochloride of 1-(2-(2-aminoethoxy)ethyl)-3-(2-hydroxyethyl)urea IIIf

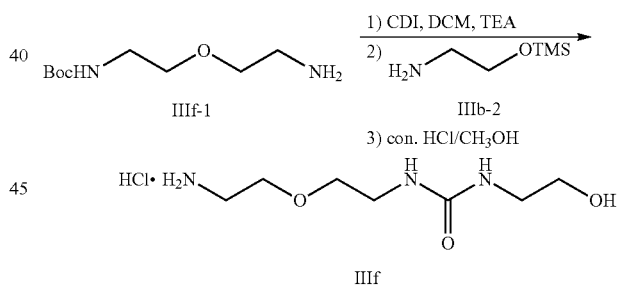

IIIf-1 (0.20 g, 1.0 mmol, 1.0 equivalent weight) and TEA (0.4 mL, 3.0 mmol, 3.0 equivalent weight) were dissolved in DCM (40 mL). In an ice bath, CDI (0.17 g, 1.1 mmol, 1.1 equivalent weight) was added and stirred for 10 min, and then the mixture was heated to room temperature and stirring was continued for 30 min. Then, at room temperature, IIIb-2 (0.13 g, 1.0 mmol, 1.0 equivalent weight) was added dropwise into the above reaction solution, and stirring was continued for 3 h. The solvent was concentrated to obtain a sticky liquid. Finally, the sticky liquid was dissolved in methanol (10 mL), and concentrated hydrochloric acid (con. HCl, 2 mL) was added dropwise into the reaction mixture, which was then subjected to heating and refluxing for 2 h. The solvent was concentrated to obtain 0.50 g colorless and transparent sticky liquid IIIf. The crude product was directly used for the next reaction without separation (the yield was calculated based on 100%).

LC-MS MS-ESI (m/z) 192.3 [M+H]+, 214.2 [M+Na]+.

Example 25 Preparation of Compound 1-((2-(2-(5-cyanopyridin-3-yl) methoxy-4-(2-cyano-3-(2,3-dihydrobenzo[b]) [1,4-dioxin-6-yl])benzyloxy)-5-methyl)benzylamino)-2-(2-aminoethoxy)ethyl)-3-(2-hydroxyethyl)urea I-7

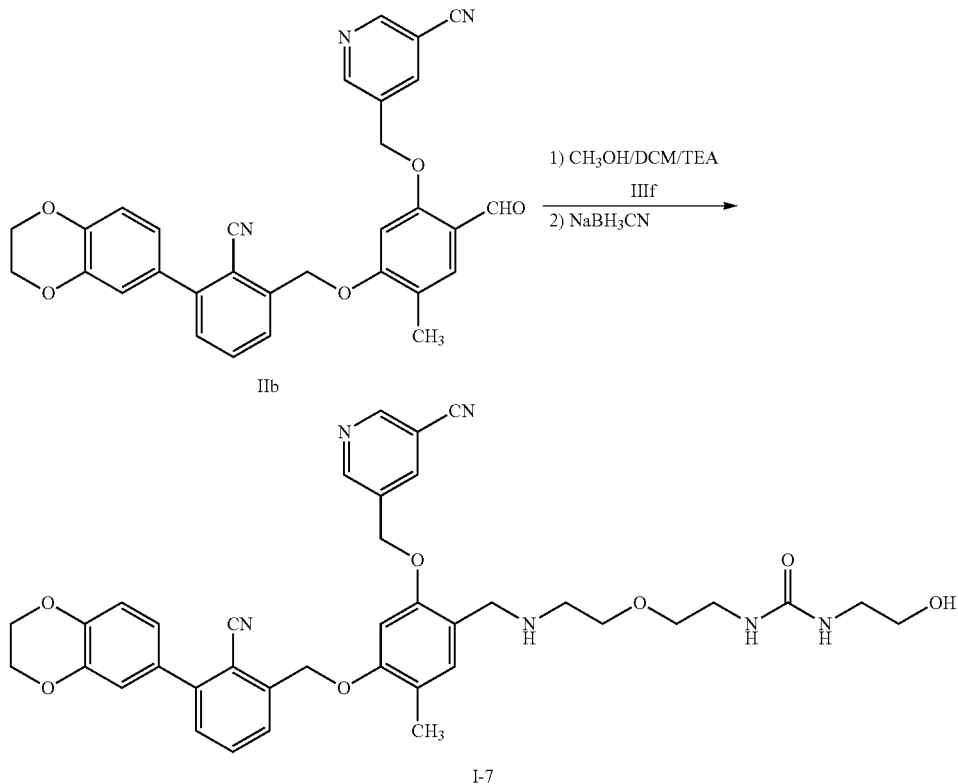

IIb (0.06 g, 0.12 mmol, 1.0 equivalent weight) and the crude product of IIIf (0.25 g, 0.5 mmol, 4.2 equivalent weight) were respectively weighted and dissolved in a mixed solvent of CH3OH/DCM (15 mL/2 mL), and TEA (2 mL) was added dropwise, and then anhydrous MgSO4 (1.00 g) was added. The mixture was stirred over night at room temperature, and NaBH3CN (0.06 g, 1.0 mmol, 8.3 equivalent weight) was added, and the stirring was continued for 2 h. The end of the reaction was detected by LC-MS test. The reaction mixture was diluted with DCM (20 mL), and extracted with water. The organic phase was combined and washed with water (40 mL×2), washed with saturated NaCl solution (40 mL×2), and dried with anhydrous MgSO4. The organic phase was concentrated. The crude product was purified by preparative TLC (developing solvent: DCM/CH3OH 7/1), to obtain 8.0 mg light yellow solid I-7 (the yield was 9.6%).

LC-MS MS-ESI (m/z) 693.8 [M+H]+, 715.7 [M+Na]+, 1H-NMR (400 MHz, DMSO-d6) δ ppm 9.03 (m, 2H), 8.49 (s, 1H), 7.75 (m, 1H), 7.68 (m, 1H), 7.57 (m, 1H), 7.28 (s, 1H), 7.10 (s, 1H), 7.00-7.05 (m, 2H), 6.99 (s, 1H), 6.0 (m, 2H), 5.35 (m, 4H), 4.63 (t, 1H, J=5.2 Hz), 4.31 (s, 4H), 4.11 (s, 2H), 3.63 (t, 2H, J=5.0 Hz), 3.36 (m, 2H), 3.15 (m, 2H), 3.03-3.10 (m, 4H), 3.00 (m, 2H), 2.13 (s, 3H).

Example 26 Preparation of Intermediate Hydrochloride of 1-(2-(2-aminoethoxy)ethyl)-3-(2-(methylsulfonyl)ethyl)urea IIIg

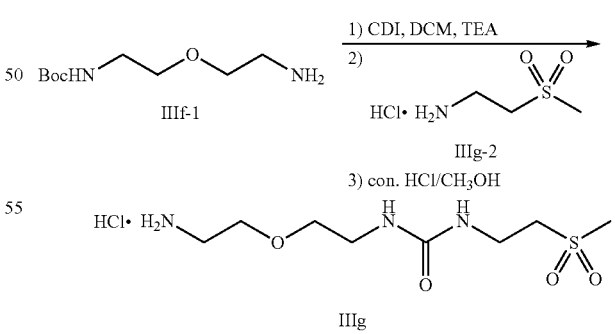

IIIf-1 (0.20 g, 1.0 mmol, 1.0 equivalent weight) and TEA (0.4 mL, 3.0 mmol, 3.0 equivalent weight) were dissolved in DCM (40 mL). In an ice bath, CDI (0.17 g, 1.1 mmol, 1.1 equivalent weight) was added and stirred for 10 min, and then the mixture was heated to room temperature and stirring was continued for 30 min. Subsequently, at room temperature, IIIg-2 (0.16 g, 1.0 mmol, 1.0 equivalent weight) was added dropwise into the above reaction solution, and stirring was continued for 3 h. The solvent was concentrated to obtain a sticky liquid. Finally, the sticky liquid was dissolved in methanol (10 mL), and concentrated hydrochloric acid (con. HCl, 2 mL) was added dropwise into the reaction mixture, which was then subjected to heating and refluxing for 2 h. The solvent was concentrated to obtain 0.50 g colorless and transparent sticky liquid IIIg. The crude product was directly used for the next reaction without separation (the yield was calculated based on 100%).

LC-MS MS-ESI (m/z) 254.4 [M+H]$^+$, 276.3 [M+Na]$^+$.

Example 27 Preparation of Intermediate Hydrochloride of 1-(2-(2-aminoethoxy)ethyl)-3-(2-(N,N'-dimethylamino)ethyl)urea IIIh

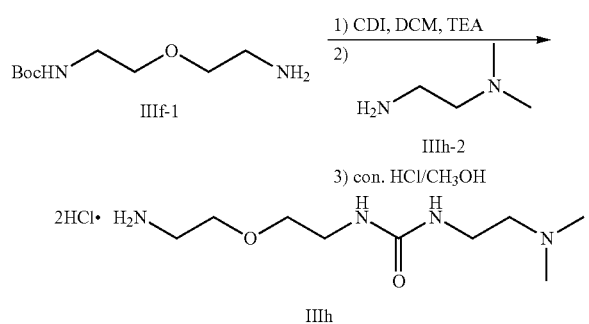

IIIf-1 (0.20 g, 1.0 mmol, 1.0 equivalent weight) and TEA (0.4 mL, 3.0 mmol, 3.0 equivalent weight) were dissolved in DCM (40 mL). In an ice bath, CDI (0.17 g, 1.1 mmol, 1.1 equivalent weight) was added and stirred for 10 min, and then the mixture was heated to room temperature and stirring was continued for 30 min. Subsequently, at room temperature, IIIh-2 (0.09 g, 1.0 mmol, 1.0 equivalent weight) was added dropwise into the above reaction solution, and stirring was continued for 3 h. The solvent was concentrated to obtain a sticky liquid. Finally, the sticky liquid was dissolved in methanol (10 mL), and concentrated hydrochloric acid (con. HCl, 2 mL) was added dropwise into the reaction mixture, which was then subjected to heating and refluxing for 2 h. The solvent was concentrated to obtain 0.50 g colorless and transparent sticky liquid IIIh. The crude product was directly used for the next reaction without separation (the yield was calculated based on 100%).

LC-MS MS-ESI (m/z) 219.1 [M+H]$^+$, 241.1 [M+Na]$^+$.

Example 28 Preparation of Intermediate Hydrochloride of 1-(2-aminoethyl)-3-(2-(N,N'-dimethylamino)ethyl)urea IIIi

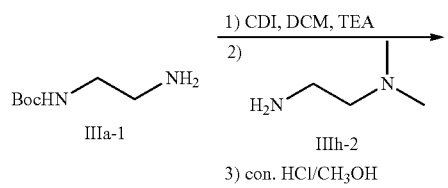

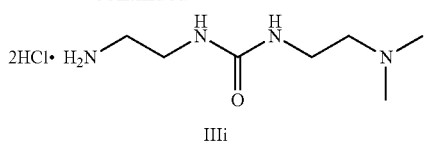

IIIa-1 (0.32 g, 2.0 mmol, 1.0 equivalent weight) and TEA (0.85 mL, 6.0 mmol, 3.0 equivalent weight) were dissolved in DCM (20 mL). In an ice bath, CDI (0.34 g, 2.1 mmol, 1.1 equivalent weight) was added and stirred for 10 min, and then the mixture was heated to room temperature and stirring was continued for 30 min. Subsequently, at room temperature, IIIh-2 (0.17 g, 2.0 mmol, 1.0 equivalent weight) was added dropwise into the above reaction solution, and stirring was continued for 3 h. The solvent was concentrated to obtain a sticky liquid. Finally, the sticky liquid was dissolved in methanol (10 mL), and concentrated hydrochloric acid (con. HCl, 2 mL) was added dropwise into the reaction mixture, which was then subjected to heating and refluxing for 2 h. The solvent was concentrated to obtain 1.00 g colorless and transparent sticky liquid IIIi. The crude product was directly used for the next reaction without separation (the yield was calculated based on 100%).

LC-MS MS-ESI (m/z) 175.05 [M+H]$^+$, 197.02 [M+Na]$^+$.

Example 29 Preparation of Intermediate Hydrochloride of 1-(2-aminoethyl)-3-(2-(methylsulfonyl)ethyl)urea IIIj

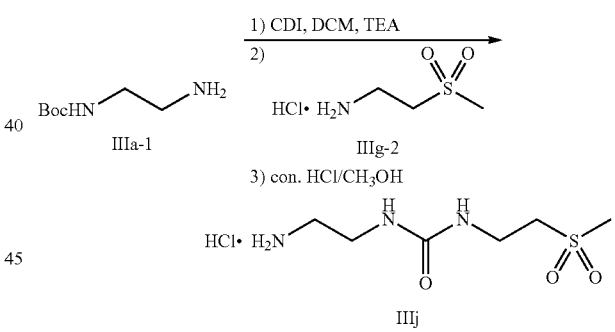

IIIa-1 (0.32 g, 2.0 mmol, 1.0 equivalent weight) and TEA (0.85 mL, 6.0 mmol, 3.0 equivalent weight) were dissolved in DCM (20 mL). In an ice bath, CDI (0.34 g, 2.1 mmol, 1.1 equivalent weight) was added and stirred for 10 min, and then the mixture was heated to room temperature and stirring was continued for 30 min. Subsequently, at room temperature, IIIg-2 (0.32 g, 2.0 mmol, 1.0 equivalent weight) was added dropwise into the above reaction solution, and stirring was continued for 3 h. The solvent was concentrated to obtain a sticky liquid. Finally, the sticky liquid was dissolved in methanol (10 mL), and concentrated hydrochloric acid (con. HCl, 2 mL) was added dropwise into the reaction mixture, which was then subjected to heating and refluxing for 2 h. The solvent was concentrated to obtain 1.00 g colorless and transparent sticky liquid IIIj. The crude product was directly used for the next reaction without separation (the yield was calculated based on 100%).

LC-MS MS-ESI (m/z) 209.98 [M+H]+, 232.01 [M+Na]+.

Example 30 Preparation of Compound 1-((2-(2-(5-cyanopyridin-3-yl)methoxy-4-(2-cyano-3-(2,3-dihydrobenzo[b])[1,4-dioxin-6-yl])benzyloxy)-5-methyl)benzylamino)-2-ethyl)-3-(2-(N-morpholine)ethyl)urea I-8

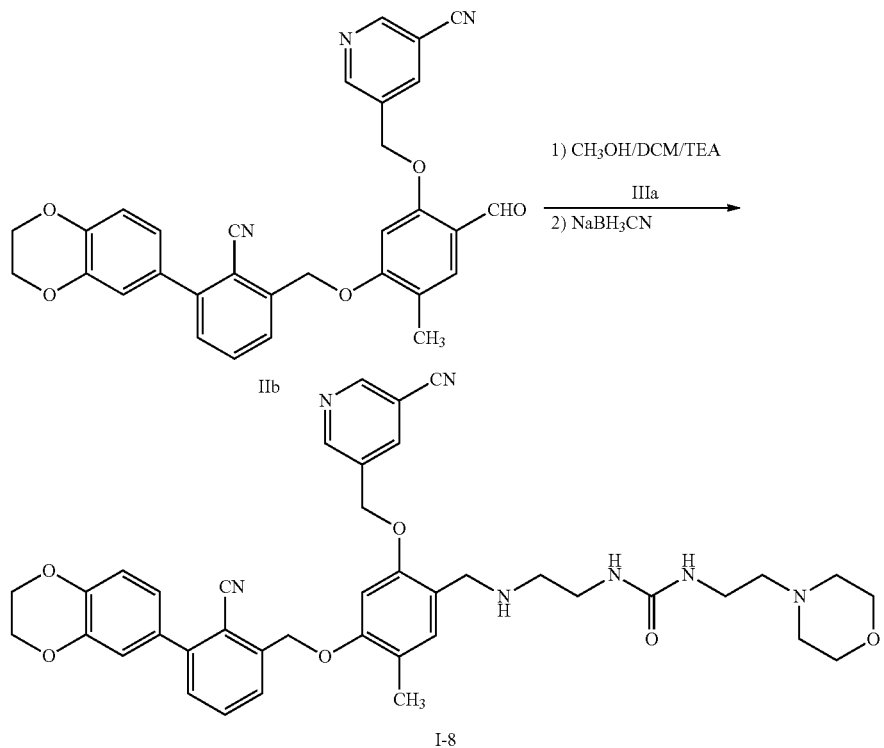

IIb (0.06 g, 0.12 mmol, 1.0 equivalent weight) and the crude product of IIIg (0.25 g, 0.5 mmol, 4.2 equivalent weight) were respectively weighted and dissolved in a mixed solvent of CH₃OH/DCM (15 mL/2 mL), and TEA (2 mL) was added dropwise, and then anhydrous MgSO₄ (1.00 g) was added. The mixture was stirred over night at room temperature, and NaBH₃CN (0.06 g, 1.0 mmol, 8.3 equivalent weight) was added, and the stirring was continued for 2 h. The end of the reaction was detected by LC-MS test. The reaction mixture was diluted with DCM (20 mL), and extracted with water. The organic phase was combined and washed with water (40 mL×2), washed with saturated NaCl solution (40 mL×2), and dried with anhydrous MgSO₄. The organic phase was concentrated. The crude product was purified by TLC (developing solvent: DCM/CH₃OH 7/1), to obtain 10.0 mg light yellow solid I-8 (the yield was 11.6%).

LC-MS MS-ESI (m/z) 718.5 [M+H]+, 740.4 [M+Na]+.

Example 31 Preparation of Compound 1-((2-(2-(5-cyanopyridin-3-yl)methoxy-4-(2-cyano-3-(2,3-dihydrobenzo[b])[1,4-dioxin-6-yl])benzyloxy)-5-methyl)benzylamino)-2-(2-aminoethoxy)ethyl)-3-(2-(methylsulfonyl)ethyl)urea I-9

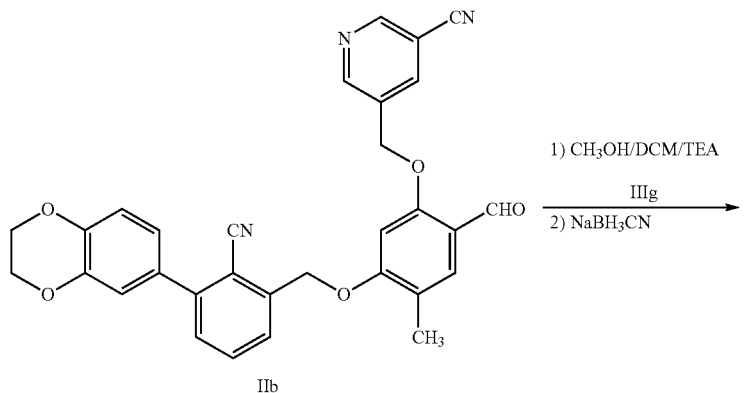

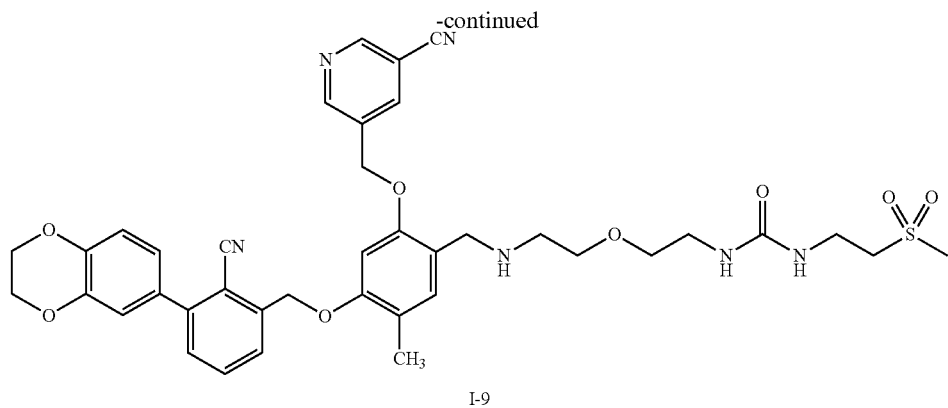

I-9

IIb (0.06 g, 0.12 mmol, 1.0 equivalent weight) and the crude product of IIIg (0.25 g, 0.5 mmol, 4.2 equivalent weight) were respectively weighted and dissolved in a mixed solvent of $CH_3OH/DCM$ (15 mL/2 mL), and TEA (2 mL) was added dropwise, and then anhydrous $MgSO_4$ (1.00 g) was added. The mixture was stirred over night at room temperature, and $NaBH_3CN$ (0.06 g, 1.0 mmol, 8.3 equivalent weight) was added, and the stirring was continued for 2 h. The end of the reaction was detected by LC-MS test. The reaction mixture was diluted with DCM (20 mL), and extracted with water. The organic phase was combined and washed with water (40 mL×2), washed with saturated NaCl solution (40 mL×2), and dried with anhydrous $MgSO_4$. The organic phase was concentrated. The crude product was purified by preparative TLC (developing solvent: $DCM/CH_3OH$ 10/1), to obtain 12.0 mg light yellow solid I-9 (the yield was 13.3%).

LC-MS MS-ESI (m/z) 755.5 [M+H]$^+$, 777.5 [M+Na]$^+$.
$^1$H-NMR (400 MHz, DMSO-d$_6$) δ ppm 9.03 (s, 1H), 9.01 (s, 1H), 8.52 (s, 1H), 7.75 (m, 1H), 7.69 (m, 1H), 7.57 (m, 1H), 7.33 (s, 1H), 7.00-7.10 (m, 4H), 6.54 (t, 1H, J=5.6 Hz), 6.34 (t, 1H, J=5.6 Hz), 5.36 (s, 4H), 4.31 (s, 4H), 4.11 (s, 2H), 3.64 (t, 2H, J=5.0 Hz), 3.32-3.40 (m, 4H), 3.03-3.19 (m, 6H), 2.97 (s, 3H), 2.13 (s, 3H).

Example 32 Preparation of Compound 1-((2-(2-(5-cyanopyridin-3-yl)methoxy-4-(2-cyano-3-(2,3-dihydrobenzo[b])[1,4-dioxin-6-yl])benzyloxy)-5-methyl)benzylamino)-2-(2-aminoethoxy)ethyl)-3-(2-(N,N'-dimethylamino)ethyl)urea I-10

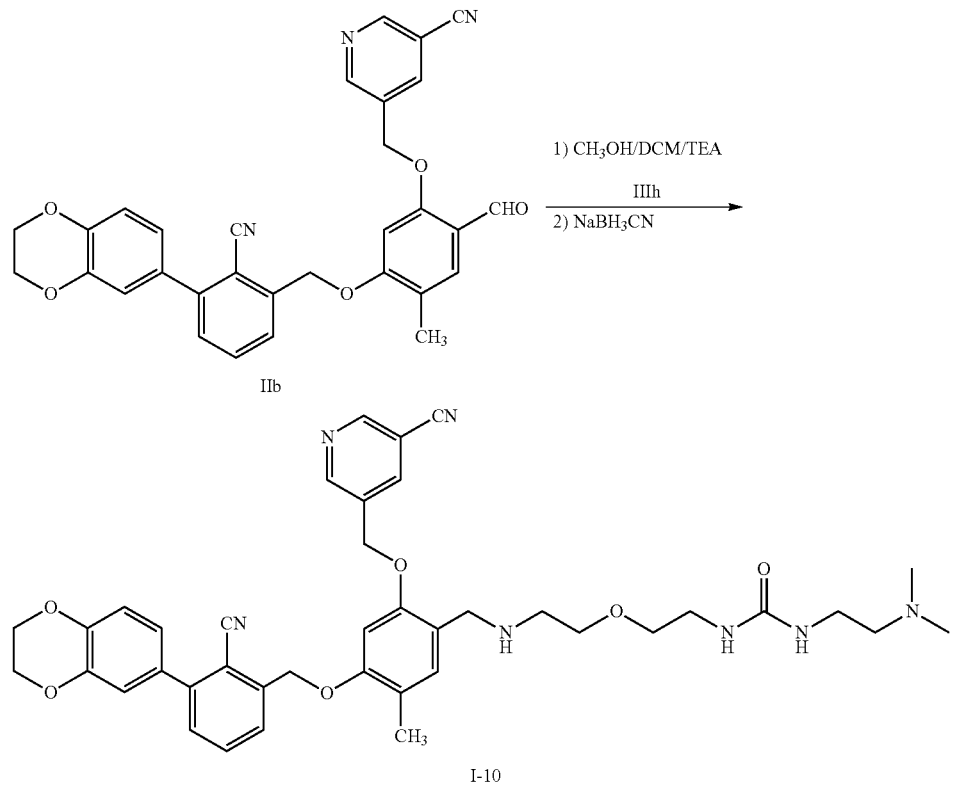

IIb (0.06 g, 0.12 mmol, 1.0 equivalent weight) and the crude product of IIIh (0.25 g, 0.5 mmol, 4.2 equivalent weight) were respectively weighted and dissolved in a mixed solvent of CH$_3$OH/DCM (15 mL/2 mL), and TEA (2 mL) was added dropwise, and then anhydrous MgSO$_4$ (1.00 g) was added. The mixture was stirred over night at room temperature, and NaBH$_3$CN (0.06 g, 1.0 mmol, 8.3 equivalent weight) was added, and the stirring was continued for 2 h. The end of the reaction was detected by LC-MS test. The reaction mixture was diluted with DCM (20 mL), and extracted with water. The organic phase was combined and washed with water (40 mL×2), washed with saturated NaCl solution (40 mL×2), and dried with anhydrous MgSO$_4$. The organic phase was concentrated. The crude product was purified by preparative TLC (developing solvent: DCM/CH$_3$OH 5/1), to obtain 6.0 mg light yellow solid I-10 (the yield was 6.9%).

LC-MS MS-ESI (m/z) 720.5 [M+H]$^+$, 742.4 [M+Na]$^+$.
$^1$H-NMR (400 MHz, DMSO-d6) δ ppm 9.02 (s, 2H), 8.50 (s, 1H), 7.69-7.75 (m, 2H), 7.58 (s, 1H), 7.28 (s, 1H), 6.98-7.20 (m, 4H), 6.37 (S, 1H), 6.11 (s, 1H), 5.34 (s, 4H), 4.31 (s, 4H), 4.02 (s, 2H), 3.60 (s, 2H), 3.32-3.40 (m, 4H), 3.03-3.19 (m, 6H), 2.33 (s, 6H), 2.13 (s, 3H).

Example 33 Preparation of Compound 1-((2-(2-(5-cyanopyridin-3-yl)methoxy-4-(2-cyano-3-(2,3-dihydrobenzo[b][1,4-dioxin-6-yl])benzyloxy)-5-methyl)benzylamino)-2-ethyl))-3-(2-(N,N'-dimethylamino)ethyl)urea I-11

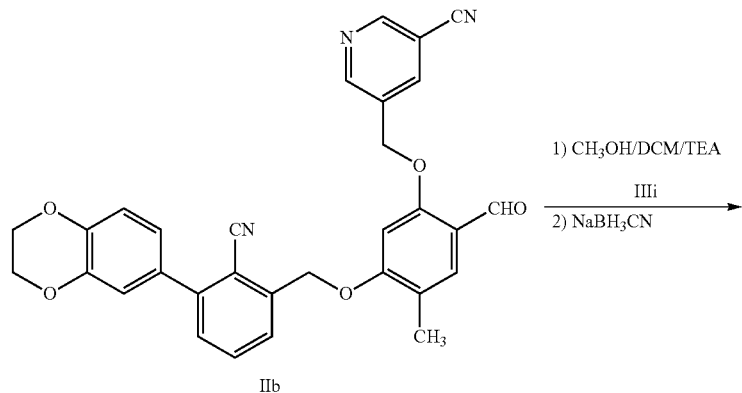

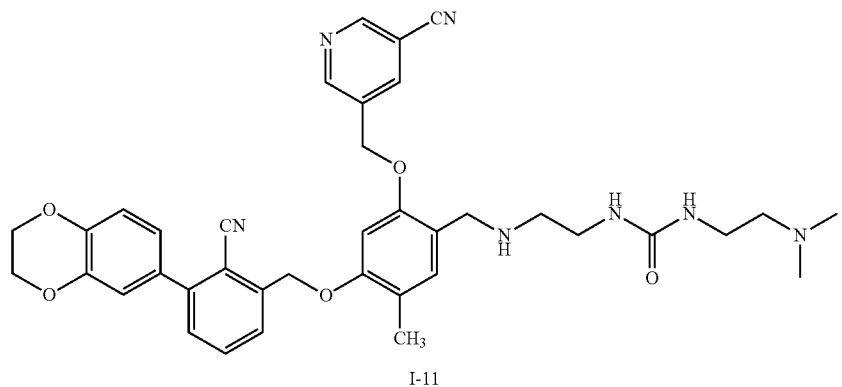

I-11

IIb (0.06 g, 0.12 mmol, 1.0 equivalent weight) and the crude product of IIIi (0.25 g, 0.5 mmol, 4.2 equivalent weight) were respectively weighted and dissolved in a mixed solvent of CH₃OH/DCM (15 mL/2 mL), and TEA (2 mL) was added dropwise, and then anhydrous MgSO₄ (1.00 g) was added. The mixture was stirred over night at room temperature, and NaBH₃CN (0.06 g, 1.0 mmol, 8.3 equivalent weight) was added, and the stirring was continued for 2 h. The end of the reaction was detected by LC-MS test. The reaction mixture was diluted with DCM (20 mL), and extracted with water. The organic phase was combined and washed with water (40 mL×2), washed with saturated NaCl solution (40 mL×2), and dried with anhydrous MgSO₄. The organic phase was concentrated. The crude product was purified by preparative TLC (developing solvent: DCM/CH₃OH 5/1), to obtain 5.5 mg light yellow solid I-11 (the yield was 6.7%).

LC-MS MS-ESI (m/z) 676.6 [M+H]⁺, 698.6 [M+Na]⁺.
¹H-NMR (400 MHz, DMSO-d6) δ ppm 9.04 (s, 2H), 8.52 (s, 1H), 7.75 (s, 1H), 7.68 (s, 1H), 7.57 (s, 1H), 7.33 (s, 1H), 7.19 (s, 1H), 7.02-7.10 (m, 2H), 6.99 (s, 1H), 6.64 (t, 1H, J=6.0 Hz), 6.57 (t, 1H, J=6.0 Hz), 5.36 (s, 4H), 4.31 (s, 4H), 4.10 (s, 2H), 3.05-3.07 (m, 6H), 2.93 (s, 2H), 2.74 (s, 6H), 2.12 (s, 3H).

Example 34 Preparation of Compound 1-((2-(2-(5-cyanopyridin-3-yl)methoxy-4-(2-cyano-3-(2,3-dihydrobenzo[b])[1,4-dioxin-6-yl])benzyloxy)-5-methyl)benzylamino)-2-ethyl))-3-(2-(methanesulfonyl)ethyl) urea I-12

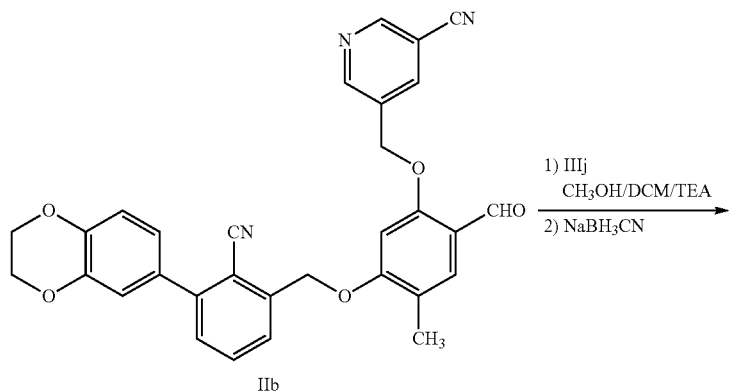

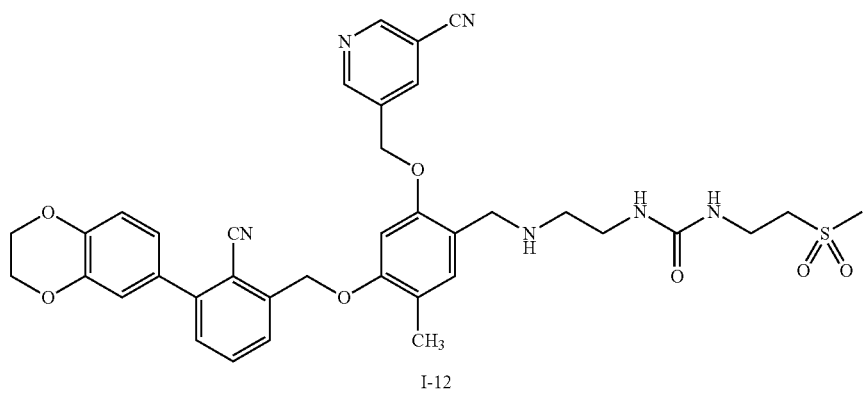

IIb (0.06 g, 0.12 mmol, 1.0 equivalent weight) and the crude product of IIIj (0.25 g, 0.5 mmol, 4.2 equivalent weight) were respectively weighted and dissolved in a mixed solvent of CH₃OH/DCM (15 mL/2 mL), and TEA (2 mL) was added dropwise, and then anhydrous MgSO₄ (1.00 g) was added. The mixture was stirred over night at room temperature, and NaBH₃CN (0.06 g, 1.0 mmol, 8.3 equivalent weight) was added, and the stirring was continued for 2 h. The end of the reaction was detected by LC-MS test. The reaction mixture was diluted with DCM (20 mL), and extracted with water. The organic phase was combined and washed with water (40 mL×2), washed with saturated NaCl solution (40 mL×2), and dried with anhydrous MgSO₄. The organic phase was concentrated. The crude product was purified by preparative TLC (developing solvent: DCM/CH₃OH 7/1), to obtain 7.0 mg light yellow solid I-12 (the yield was 8.2%).

LC-MS MS-ESI (m/z) 711.5 [M+H]⁺, 733.5 [M+Na]⁺.
¹H-NMR (400 MHz, DMSO-d6) δ ppm 9.00 (m, 2H), 8.46 (s, 1H), 7.75 (m, 1H), 7.68 (m, 1H), 7.57 (m, 1H), 7.21 (s, 1H), 7.10 (m, 1H), 7.00-7.06 (m, 2H), 6.95 (s, 1H), 6.40 (t, 1H, J=5.6 Hz), 6.34 (t, 1H, J=5.6 Hz), 5.32 (s, 4H), 4.31 (s, 4H), 3.91 (s, 2H), 3.37-3.42 (m, 2H), 3.18-3.21 (m, 4H), 2.97 (s, 3H), 2.76 (m, 2H), 2.12 (s, 3H).

Example 35 Preparation of Intermediate 1-(2-N-(benzyloxycarbonyl)aminoethyl)-3-(O-benzyl-L-serinate-2-yl)urea IIIk-3

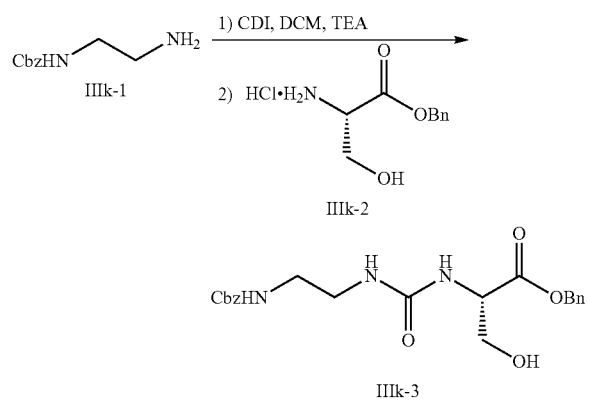

IIIk-1 (0.97 g, 5.0 mmol, 1.0 equivalent weight) and TEA (2.8 mL, 20.0 mmol, 4.0 equivalent weight) were dissolved in DCM (20 mL). In an ice bath, CDI (0.86 g, 5.3 mmol, 1.1 equivalent weight) was added and stirred for 10 min, and then the mixture was heated to room temperature and stirring was continued for 30 min. Subsequently, at room temperature, IIIk-2 (1.16 g, 5.0 mmol, 1.0 equivalent weight) was added dropwise into the above reaction solution, and the mixture was stirred overnight until the end of the reaction. The resultant was extracted with DCM/CH3OH 10/1 (80 mL). The organic phase was combined and washed with water (50 mL×2), washed with saturated NaCl solution (50 mL×2), and dried with anhydrous MgSO₄. The organic phase was concentrated. The crude product was separated and purified with column chromatography (eluent: EtOAc), to obtain 0.40 g white solid IIk-3 (the yield was 19.2%).

Example 36 Preparation of Intermediate 1-(2-N-(benzyloxycarbonyl)aminoethyl)-3-(O-benzyl-L-serinate-2-yl)urea IIIk

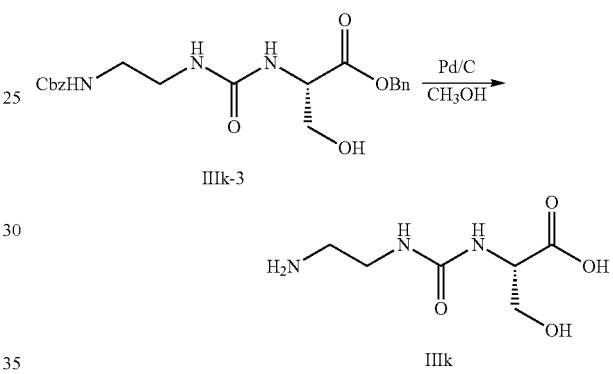

IIIk-3 (0.40 g, 1.0 mmol) was dissolved in CH₃OH (15 mL), and Pd/C (5%, 0.10 g) was added. The mixture was stirred overnight under conditions of hydrogen. After the completion of the reaction, the resultants were subjected to suction filtration, and the filtrate was spin dried, to obtain 0.18 g white solid. The crude product was directly used in the next reaction without separation (the yield was 94.7%).

Example 37 Preparation of Compound 1-((2-(2-(5-cyanopyridin-3-yl)methoxy-4-(2-cyano-3-(2,3-dihydrobenzo[b])[1,4-dioxin-6-yl])benzyloxy)-5-methyl)benzylamino)-2-ethyl))-3-(L-serine-2-yl)urea I-13

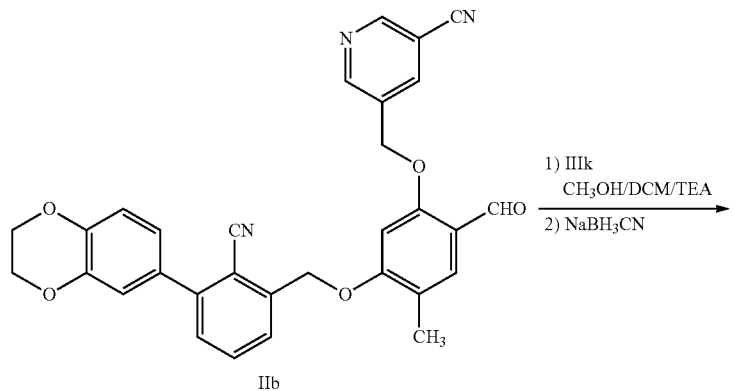

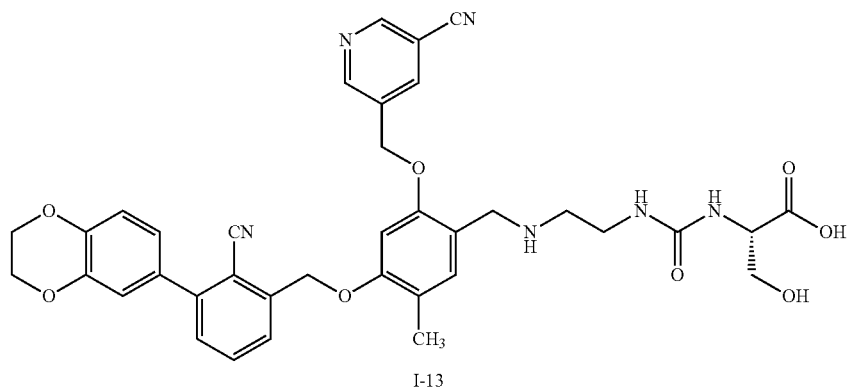

I-13

IIb (0.11 g, 0.2 mmol, 1.0 equivalent weight) and the crude product of IIIk (0.10 g, 0.5 mmol, 2.5 equivalent weight) were respectively weighted and dissolved CH3OH, and TEA (2 mL) was added dropwise, and then anhydrous MgSO$_4$ (1.00 g) was added. The mixture was stirred over night at room temperature, and NaBH$_3$CN (0.06 g, 1.0 mmol, 5.0 equivalent weight) was added, and the stirring was continued for 2 h. The end of the reaction was detected by LC-MS test. The reaction was quenched with water. The mixture was extracted with DCM/CH3OH 5/1 (60 mL). The organic phase was combined and washed with water (40 mL×2), washed with saturated NaCl solution (40 mL×2), and dried with anhydrous MgSO$_4$. The organic phase was concentrated. The crude product was purified by preparative TLC (developing solvent: DCM/CH$_3$OH 5/1), to obtain 8.0 mg white solid I-13 (the yield was 5.8%).

LC-MS MS-ESI (m/z) 693.7 [M+H]$^+$, 715.7 [M+Na]$^+$.

Example 38 Preparation of Intermediate 1-(2-N-(tert-butoxycarbonyl)aminoethyl)-3-(2-N-(9-fluorenylmethoxycarbonyl)aminoethyl)urea IIII-3

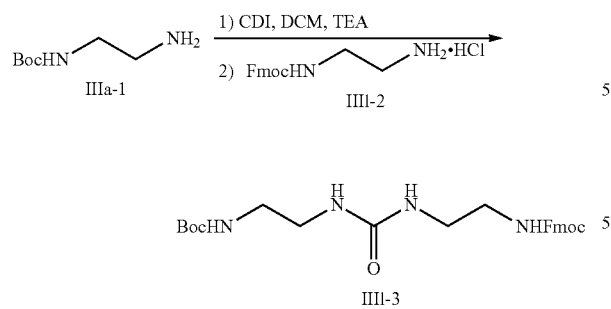

IIIa-1 (0.32 g, 2.0 mmol, 1.0 equivalent weight) and TEA (0.85 mL, 6.0 mmol, 3.0 equivalent weight) were dissolved in DCM (20 mL). In an ice bath, CDI (0.34 g, 2.1 mmol, 1.1 equivalent weight) was added and stirred for 10 min, and then the mixture was heated to room temperature and stirring was continued for 30 min. Subsequently, at room temperature, IIII-2 (0.32 g, 2.0 mmol, 1.0 equivalent weight) was added dropwise into the above reaction solution, and the mixture was stirred overnight until the end of the reaction. The resultant was extracted with DCM/CH$_3$OH 10/1 (50 mL). The organic phases were combined and washed with water (40 mL×2), washed with saturated NaCl solution (40 mL×2), and dried with anhydrous MgSO$_4$. The organic phase was concentrated. The crude product was separated by column chromatography (eluent: PE/EtOAc, 1/1-EtOAc), to obtain 0.50 g white solid IIII-33 (the yield was 21.2%).

Example 39 Preparation of Intermediate Hydrochloride of 1-(2-aminoethyl)-3-(2-N-(9-fluorenylmethoxycarbonyl)aminoethyl)urea IIII

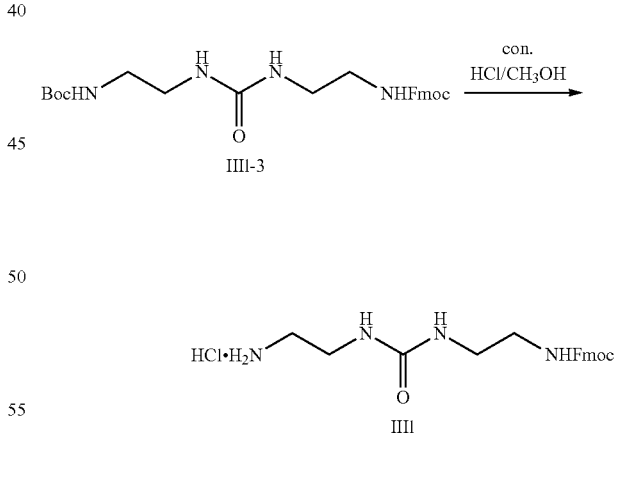

IIII-3 (0.50 g, 1.0 mmol) was dissolved in CH$_3$OH (10 mL), and con.HCl(2 mL) was added dropwise, and the mixture was reacted at room temperature for 3 h. After the completion of the reaction, the solvent was concentrated, to obtain 0.45 g white solid IIII, which was directly used for the next reaction without purification (the yield was calculated based on 100%).

Example 40 Preparation of Intermediate 1-((2-(2-(5-Cyanopyridin-3-yl)methoxy-4-(2-cyano-3-(2,3-dihydrobenzo[b])[1,4-dioxin-6-yl])benzyloxy)-5-methyl)-N-(tert-butoxycarbonyl)benzylamino)-2-ethyl)-3-(2-N-(9-fluorenylmethoxycarbonyl)aminoethyl)urea I-14-1

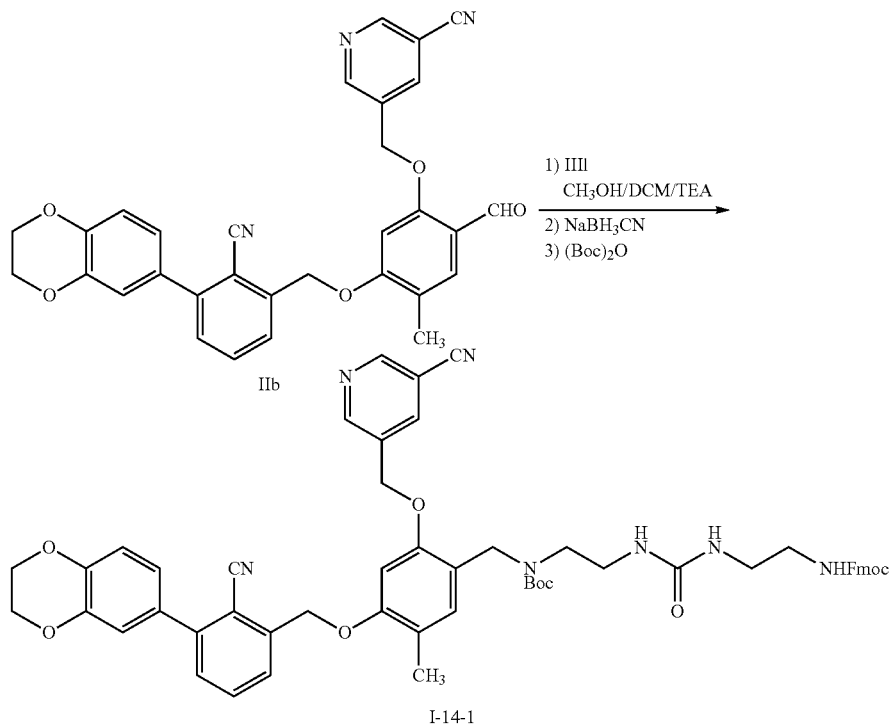

IIb (0.30 g, 0.58 mmol, 1.0 equivalent weight) and the crude product of IIIl (0.45 g, 1.0 mmol, 1.7 equivalent weight) were respectively weighted and dissolved in a mixed solvent of $CH_3OH$/DCM (15 mL/2 mL), and TEA (2 mL) was added dropwise, and then anhydrous $MgSO_4$ (1.00 g) was added. The mixture was stirred over night at room temperature, and $NaBH_3CN$ (0.19 g, 3.0 mmol, 3.0 equivalent weight) was added, and stirring was continued for 3 h. The end of the reaction was detected by LC-MS test. Then $(Boc)_2O$ (0.43 g, 2.0 mmol, 2.0 equivalent weight) was directly added, and stirring at room temperature was continued overnight. After the completion of the reaction, the mixture was extracted with $DCM/CH_3OH$ 10/1 (80 mL). The organic phase was combined and washed with water (40 mL×2), washed with saturated NaCl solution (40 mL×2), and dried with anhydrous $MgSO_4$. The organic phase was concentrated. The crude product was separated by column chromatography (eluent: EtOAc), to obtain 0.20 g white solid I-14-1 (the yield was 35.6%).

LC-MS MS-ESI (m/z) 970.7 [M+H]$^+$, 992.6 [M+Na]$^+$.

Example 41 Preparation of Intermediate 1-((2-(2-(5-cyanopyridin-3-yl)methoxy-4-(2-cyano-3-(2,3-dihydrobenzo[b])[1,4-dioxin-6-yl])benzyloxy)-5-methyl)-N-(tert-butoxycarbonyl)benzylamino)-2-ethyl)-3-(2-aminoethyl)urea I-14-2

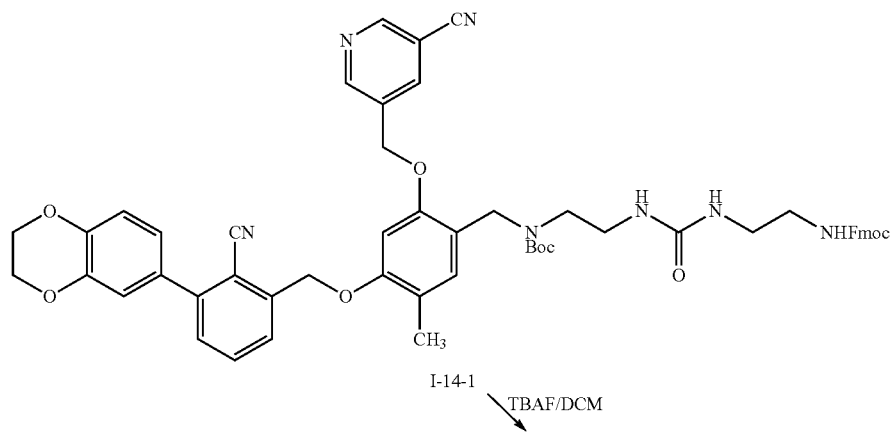

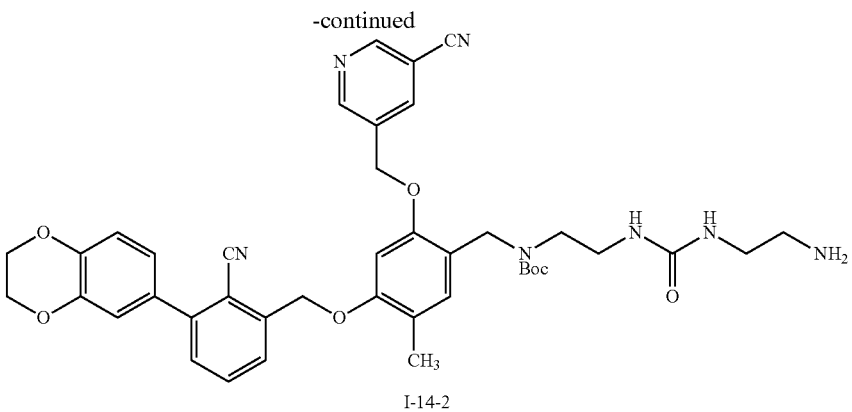

At room temperature, I-14-1 (0.20 g, 0.2 mmol) was dissolved in DCM (10 mL), tetrabutylammonium bromide (TBAF, 1 M in THF, 2 mL) was added in, and stirred for 3 h until the completion of the reaction. The reaction mixture was diluted with DCM/CH$_3$OH 10/1 (60 mL), washed with water (40 mL×2), washed with saturated NaCl solution (40 mL×2), and dried with anhydrous MgSO$_4$. The organic phase was concentrated, to obtain 0.15 g sticky solid I-14-2, which was directly used for the next reaction without purification (the yield was calculated based on 100%).

Example 42 Preparation of Compound 1-((2-(2-(5-cyanopyridin-3-yl)methoxy-4-(2-cyano-3-(2,3-dihydrobenzo[b])[1,4-dioxin-6-yl])benzyloxy)-5-methyl)-benzylamino)-2-ethyl)-3-(2-acrylamidoethyl)urea I-14

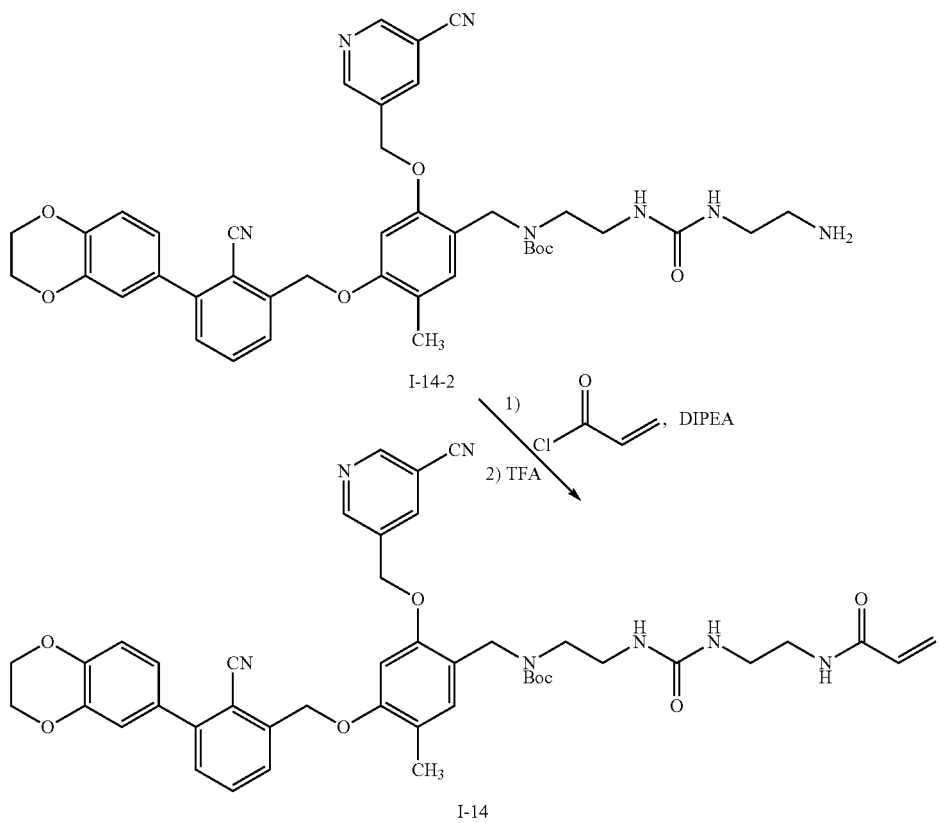

I-14-2 (0.15 g, 0.2 mmol, 1.0 equivalent weight) was dissolved in DCM (10 mL), and DIPEA (0.2 mL, 2.0 mmol, 10.0 equivalent weight) was added. In an ice bath, acryloyl chloride (32 µL, 0.4 mmol, 2.0 equivalent weight) was added dropwise, and then the mixture was heated to room temperature, and stirred overnight. After the completion of the reaction, it was quenched with water. The mixture was extracted with DCM/CH$_3$OH 5/1 (60 mL). The organic phase was combined and washed with water (40 mL×2), washed with saturated NaCl solution (40 mL×2), and dried with anhydrous MgSO$_4$. The organic phase was concentrated, to obtain a sticky solid. Then the sticky solid was dissolved in DCM (3 mL), and TFA (2 mL) was added dropwise, and the mixture was stirred at room temperature for 2 h. After the completion of the reaction, the resultant was diluted with water, and extracted with DCM. The organic phase was combined and washed with water (40 mL×2), washed with saturated NaCl solution (40 mL×2), and dried with anhydrous MgSO$_4$. The organic phase was concentrated, and the crude product was purified by preparative TLC (developing solvent: DCM/CH$_3$OH 7/1), to obtain 7.5 mg white solid I-14 (the yield was 5.3%).

LC-MS MS-ESI (m/z) 702.6 [M+H]$^+$, 724.5 [M+Na]$^+$.
$^1$H-NMR (400 MHz, DMSO-d$_6$) δ ppm 8.98-8.99 (m, 2H), 8.43 (s, 1H), 8.18 (s, 1H), 7.75 (m, 1H), 7.67 (m, 1H), 7.56 (m, 1H), 7.17 (s, 1H), 7.10 (s, 1H), 7.02-7.09 (m, 3H), 6.92 (s, 1H), 6.17 (m, 2H), 6.07 (m, 1H), 5.60 (m, 1H), 5.32 (s, 4H), 4.31 (s, 4H), 3.78 (m, 2H), 3.44 (m, 2H), 3.04-3.13 (m, 4H), 2.65 (m, 2H), 2.11 (s, 3H).

In-Vitro Biological Evaluation

The present test method was used for the in-vitro activity evaluation of the compounds of the present disclosure, including an in-vitro protein level binding inhibiting activity evaluation method and a cell level biological function activity evaluation method.

The purpose of present test is to comprehensively evaluate the effects of different compounds on PD-1/PD-L1 binding inhibitory activity and the biological activity of the cell model, including the growth activity of specific model cells and the biological activity of primary T cells.

Example A Screening Method of In-Vitro PD-1/PD-L1 Binding Inhibition

Main Principle of the Experiment (HTRF)

Homogeneous Time-Resolved Fluorescence (HTRF): The PD-1 protein carried an His tag and the Fc fusion protein of its ligand PD-L1 carried an hFc tag. An anti-hFc antibody labeled with a chelating marker of Eu element and an anti-His antibody labeled with XL66 were respectively combined with two corresponding tags. After laser excitation (320 nm), energy was transferred from the donor Eu to the acceptor XL665, so that the XL665 emitted light (665 nm). When a small molecule compound inhibitor was added, the binding of PD-1 to PD-L1 was blocked, so that Eu and XL665 were far apart, energy cannot be transferred, and XL665 did not emit light. The basic detection principle was as follows (see FIG. 3):

Materials and Equipment of the Experiment

The His-tagged human recombinant PD-1 protein (Cat#: 80448-R08H-100) and human recombinant PD-L1-Fc fusion protein (Cat#: 90251-CO2H-100) were purchased from Sino Biological Inc., and the anti-hFc-Eu$^{3+}$ and anti-His-XL665 antibody were purchased from Cisbio. Other related reagents such as dilution buffer, detection buffer were all purchased from Cisbio. The fluorescence detection instrument Tecan (Spark 10M) was purchased from Tecan, Switzerland.

Main Process of the Experiment

The experimental process was carried out in accordance with the procedure required by the instruction manual for the test reagent (Invitrogen). The process was as follows:

(1) Preparation of the experiment: The test compound was diluted to a different concentration gradient with a dilution buffer (the maximum final concentration was 10 µM in 20 µL final reaction system), the His-PD-1 protein was diluted to 800 nM (the final concentration was 100 nM in 20 µL final reaction system), and the PD-L1-Fc fusion protein was diluted to 16 nM (the final concentration was 2 nM). The anti-His-XL665 antibody and the anti-hFc-Eu$^{3+}$ antibody were diluted 20-fold and 100-fold, respectively, with the test diluent according to the reagent requirements.

(2) 5 µL of the test compound, 2.5 µL of PD-L1 protein and 2.5 µL of PD-1 protein solution were evenly mixed, and then reacted at room temperature for 15 min. Subsequently, 5 µL of anti-His-XL665 antibody and 5 µL of anti-hFc-Eu$^{3+}$ antibody were added to the system, and the incubation was continued for 3 hours followed by detection.

(3) At the same time of detection of the reaction, control groups were set, including a 0-inhibited positive control to which no test compound was added, and a negative control to which no PD-1 protein was added. All tests were run in duplicate.

(4) The fluorescence signal of each well was detected by a fluorescence detector Tecan (Spark 10M) with an excitation wavelength of 320 nm and detected emission wavelengths of 620 nm and 665 nm, respectively. The intensity of PD-1/PD-L1 binding to each other referred to the fluorescence signal ratio Em665/Em620.

(5) Formula for calculating the binding inhibition rate of test compounds: inhibition rate (%)=[1−(ratio of fluorescence signals of detection holes−negative control)/(ratio of fluorescence signals of 0-inhibited positive control−negative control)]×100%. After calculating the binding inhibition rate of the test compounds with different concentration gradients, the 50% inhibitory concentration (IC$_{50}$) was further calculated. The data was shown in Table 3 below.

TABLE 3

IC$_{50}$ data of representative compounds of the present disclosure on inhibiting PD-1/PD-L1 binding in-vitro

| Compound | IC$_{50}$ (nM) | Compound | IC$_{50}$ (nM) | Compound | IC$_{50}$ (nM) |
|---|---|---|---|---|---|
| I-1 | 1,710 | I-2 | 580.5 | I-3 | 3,120 |
| I-4 | 37.48 | I-5 | 36.43 | I-6 | 70.20 |
| I-7 | 43.69 | I-8 | 60.97 | I-9 | 28.07 |
| I-10 | 73.31 | I-11 | 76.13 | I-12 | 49.15 |
| I-13 | 15.78 | I-14 | 197.1 | — | — |

It can be seen from the above results that the compounds of the present disclosure has good in-vitro PD-1/PD-L1 binding inhibition activity.

Example B Detection of Cytotoxic Activity of the Compounds

In order to rule out the biological function changes of T cell caused by cytotoxic effects of the compounds themselves, MTS assay was used as a routine cytotoxicity detection method. The basic principle was that the dehydrogenase in the living cell mitochondria was capable of metabolizing and reducing the new type yellow formazan compound MTS to formazan. The amount of formazan product measured at 490 nm absorbance (OD) was directly proportional to the number of viable cells in the culture, and thus whether the test compound itself had the ability of inhibiting cell growth or killing cells can be judged basing on the OD value.

In this experiment, the T cell leukemia cell line (Jurkat cell) was evaluated for its cell growth activity according to the MTS assay.

Main Process of the Experiment

The MTS was carried out in a 96-well plate according to a routine experimental procedure.

Cell lines were inoculated into a 96-well plate at an appropriate concentration (approximately 20,000 cells/well), test compounds (final concentration 2 μM) were added, and at the same time solvent control (DMSO) and negative control wells were set, and the well was set in triplicate. The cells were further cultured for 72 h followed by detection.

After the culture, 20 μL of the a pre-prepared mixture of MTS and PMS (mixed in a ratio of 20:1) was added directly to the culture well, and incubated in a 37° C. incubator for 2 h, and then detection was conducted using a microplate reader (490 nm).

The background value of the negative control was subtracted, and the relative cell activity (%) of the test compound on cell growth=(OD value of the test well/OD value of the solvent control well)×100%. The data was shown in Table 4 below.

TABLE 4

Results of cell activity of representative compounds of the present disclosure in T cell lines

| Compound | Cell activity (%) | Compound | Cell activity (%) | Compound | Cell activity (%) |
| --- | --- | --- | --- | --- | --- |
| I-1 | 102.2 | I-2 | 100.4 | I-3 | 99.7 |
| I-4 | 93.2 | I-5 | 94.6 | I-6 | 92.1 |
| I-7 | 94.5 | I-8 | 95.1 | I-9 | 99.6 |
| I-10 | 97.1 | I-11 | 95.6 | I-12 | 91.6 |
| I-13 | 91.1 | I-14 | 101.6 | — | — |

It can be seen from the above results that activities of the T cell activity remained good using the compounds of the present disclosure.

Example C Detection of Biological Activity of PD-1 Signal Inhibition at the Cellular Level As an immune checkpoint molecule, PD-1 mainly expressed on the surface of activated T cells, while its ligand PD-L1 expressed widely. In addition to antigen-presenting cells such as dendritic cells, macrophages, and B cells, for many tumor cells, the anti-tumor immune effect can also be inhibited by up-regulating the expression of PD-L1. In the normal immune response, in addition to activating T cells by immune costimulatory molecules, the antigen-presenting cells also expressed PD-L1 antigen molecules, which were bond to PD-1 molecules on the surface of activated T cells, thereby inhibiting T cell activation and down-regulating the cytokines secreted by T cells, such as IL-2, ultimately avoiding damage to surrounding normal tissues caused by the excessive proliferation and activation of T cells.

Main Principle of the Experiment

To test the effect of PD-1/PD-L1 interaction on T cell activity in immune response, stimulation of superantigen *Staphylococcus aureus* enterotoxin type B (SEB) to human peripheral mononuclear cells (PBMC) were taken as an example. The T cell-specific cytokine IL-2 secreted by activation of T cells in the supernatant was detected, and blocking or inhibiting PD-1/PD-L1 interaction enhanced T cell activity and IL-2 secretion. In the experiment, the in-vitro SEB-stimulated T cell activation system was used to incubate with the test compound for a specified period of time, and then the effect of the compound on the IL-2 content in the supernatant was determined by enzyme-linked immunosorbant assay (ELISA).

Materials and Equipment of the Experiment

*Staphylococcus aureus* enterotoxin type B (SEB: SL008-1MG) was purchased from the Academy of Military Medical Sciences. The reagent for separating the peripheral blood PBMC of volunteers, Ficoll-Paque™ (Cat#: 17-5442-02), was purchased from GE Healthcare Inc. Anti-human PD-1 antibody (Cat#: 0330300) was purchased from Nearshore Protein Technology Co., Ltd. An ELISA kit (64IL2PEB) for detecting human IL-2 based on HTRF technology was purchased from Cisbio Inc.

Main Process of the Experiment

The experiment was carried out in a 96-well plate according to a routine cell culture experiment procedure.

Peripheral blood PBMC cells of volunteers were separated by density gradient centrifugation method and inoculated into a 96-well culture plate at an appropriate concentration (about 200,000 cells/well). SEB (200 ng/mL) was added, and the test compounds (final concentration 2 μM) was added at the same time. Solvent control (DMSO) and anti-human PD-1 antibody (5 μg/mL) positive control wells were also set. After culturing for 96 h, the supernatant was collected, and the IL-2 contents were detected according to the specifications of the kit.

The anti-human PD-1 antibody was used as a positive control. The PD-1/PD-L1 binding inhibition rate (%) of the test compound=(IL-2 content of compound treating well−solvent control group)/(antibody treating well group−solvent control group)×100% was calculated.

According to the above experimental method, the compound of the present disclosure was subjected to cytological evaluation (the test compound concentration was 2 μM), and the data summary was shown in Table 5 below.

TABLE 5

Data of representative compounds of the present disclosure on promoting human T cytokine IL-2 secretion (compared to PD-1 antibody)

| Compound | Activity of promoting IL-2 (%) |
| --- | --- |
| I-5 | 53 |
| I-6 | 56.3 |
| I-7 | 58.1 |
| I-11 | 51.7 |

It can be seen from the above results that the compounds of the present disclosure have a significant activity of promoting human T cell IL-2 secret (>50%).

In addition, FIG. 4 shows the results of compound I-5 of the present invention on promoting IL-2 secretion of PBMC cells in a variety of volunteers

The invention claimed is:

1. A compound of Formula I,

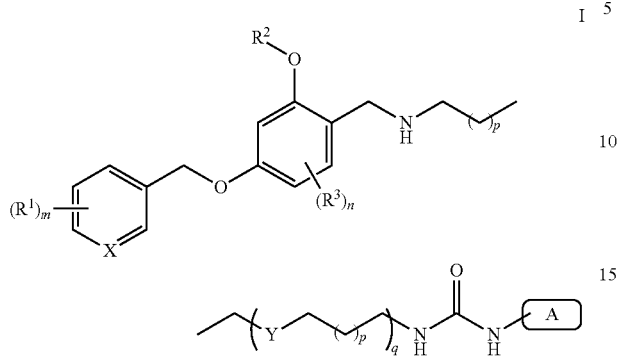

or a prodrug, a stereoisomer, and a pharmaceutically acceptable salt or a hydrate thereof; wherein, $R^1$ is one or more substituents independently selected from the group consisting of H, $C_1$-$C_4$ alkyl, CN, halogen, $NH_2$, COOH, $C_1$-$C_4$ alkylamino, $C_1$-$C_4$ alkyloxy, $C_1$-$C_4$ haloalkyl and $Ar^1$, which substituents are the same or different;

wherein, $Ar^1$ is selected from the group consisting of

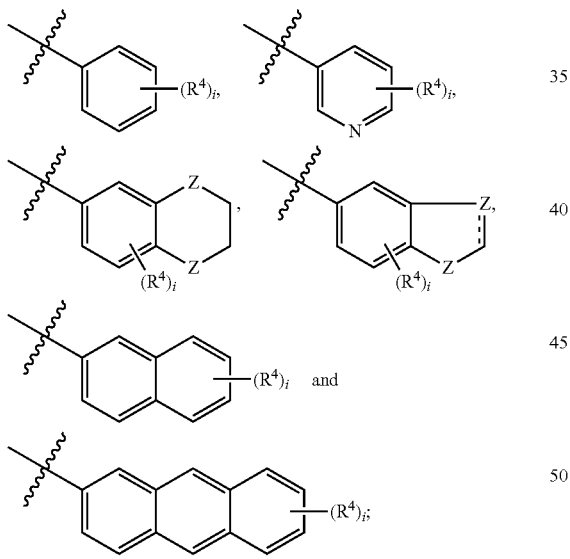

wherein, $R^4$ is one or more substituents independently selected from the group consisting of H, $C_1$-$C_4$ alkyl, CN, halogen, $NH_2$, COOH, $C_1$-$C_4$ alkylamino, $C_1$-$C_4$ alkyloxy and $C_1$-$C_4$ haloalkyl, which substituents are the same or different;

i is an integer from 1 to 5;

Z is selected from the group consisting of C, NH, O, C(O), S, S(O) and $S(O)_2$;

$R^2$ is selected from the group consisting of H, $C_1$-$C_4$ alkyl, —$CH_2$—$(CH_2)_k$—CN and —$(CH_2)_k$—$Ar^2$;

wherein, k is an integer from 0 to 6;

$Ar^2$ is selected from

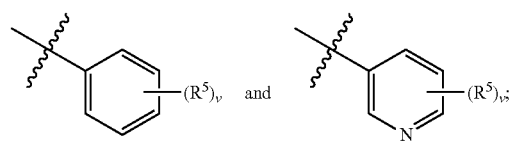

wherein, $R^5$ is one or more substituents independently selected from the group consisting of H, $C_1$-$C_4$ alkyl, CN, halogen, $NH_2$, COOH, $C_1$-$C_4$ alkylamino, $C_1$-$C_4$ alkyloxy and $C_1$-$C_4$ haloalkyl, which substituents are the same or different;

v is an integer from 1 to 5;

$R^3$ is one or more substituents independently selected from the group consisting of H, $C_1$-$C_4$ alkyl, CN, halogen, $C_1$-$C_4$ alkyloxy and $C_1$-$C_4$ haloalkyl, which substituents are the same or different;

X is selected from C and N;

Y is selected from NH, O, S, S(O) and $S(O)_2$;

A is selected from the group consisting of

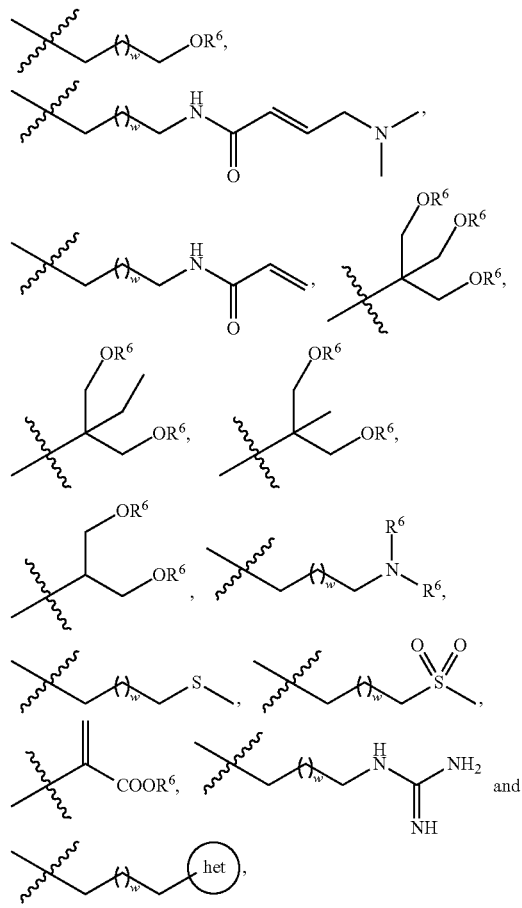

or A is a side chain of an amino acid selected from the group consisting of Gly, Ala, Ser, Lys, Arg, Thr, Asn, Gln, Phe or Glu

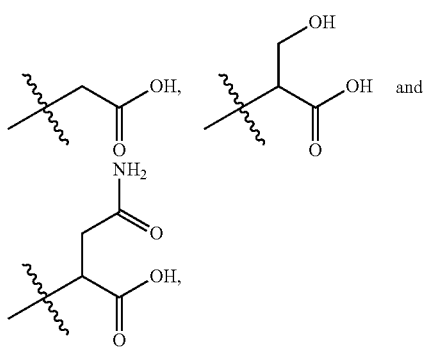

or A is a side chain of an amino acid selected from the group consisting of Gly, Ala, Ser, Lys, Arg, Thr, Asn, Gln, Phe and Glu, which is substituted with $R^6$

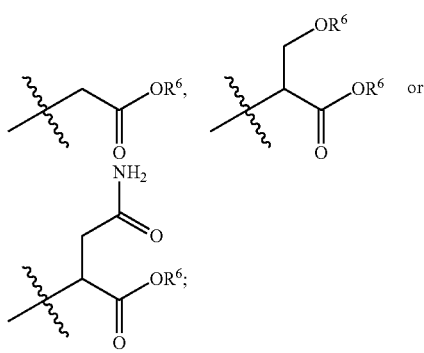

wherein,
- $R^6$ is one or more substituents independently selected from the group consisting of H, $C_1$-$C_4$ alkyl, $C_1$-$C_4$ alkylcarbonyl, alkenylcarbonyl and $C_1$-$C_4$ alkylamino $C_1$-$C_4$ alkyl $C_1$-$C_4$ alkenylcarbonyl, which substituents are the same or different;
- het is selected from saturated or aromatic heterocycles, morpholine, N-methylpiperazine, tetrahydropyrrole, pyridine, thiophene, thiazole, triazole and tetrazole;
- w is an integer from 0 to 2;
- m is an integer from 1 to 5;
- n is an integer from 1 to 3;
- p is independently an integer from 0 to 2; and
- q is an integer from 0 to 2.

2. The compound of Formula I according to claim 1, wherein,
- $R^1$ is one or more substituents independently selected from the group consisting of H, $C_1$-$C_4$ alkyl, CN, halogen, $NH_2$, COOH, $C_1$-$C_4$ alkylamino, $C_1$-$C_4$ alkyloxy, $C_1$-$C_4$ haloalkyl and $Ar^1$, which substituents are the same or different; wherein,
- $Ar^1$ is selected from the group consisting of

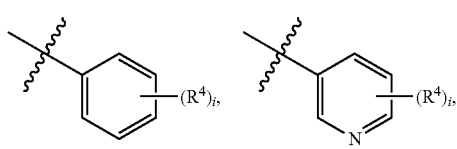

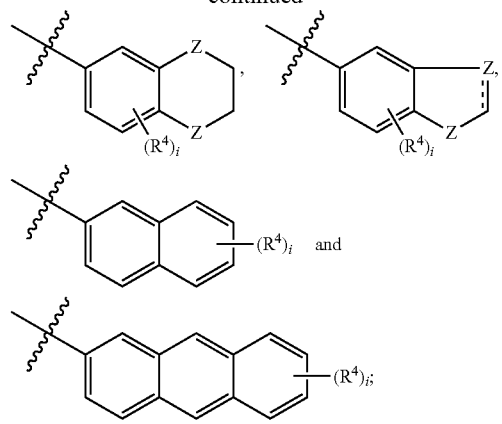

wherein,
- $R^4$ is one or more substituents independently selected from the group consisting of H, $C_1$-$C_4$ alkyl, CN, halogen, $NH_2$, COOH, $C_1$-$C_4$ alkylamino, $C_1$-$C_4$ alkyloxy and $C_1$-$C_4$ haloalkyl, which substituents are the same or different;
- i is an integer from 1 to 5;
- Z is selected from the group consisting of C, NH, O, C(O), S, S(O) and $S(O)_2$;
- $R^2$ is selected from the group consisting of $CH_3$, —$CH_2$—$(CH_2)_k$—CN and —$(CH_2)_k$—$Ar^2$;

wherein,
- k is an integer from 0 to 6;
- $Ar^e$ is selected from

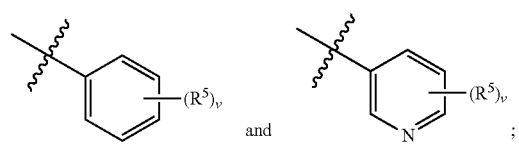

wherein,
- $R^5$ is one or more substituents independently selected from the group consisting of H, $CH_3$, $C_2H_5$, CN, F, Cl, $NH_2$, COOH, $CH_3NH$, $(CH_3)_2N$, $CH_3O$, $CF_3$ and $CHF_2$, which substituents are the same or different;
- v is an integer from 1 to 5;
- $R^3$ is one or more substituents independently selected from the group consisting of H, $C_1$-$C_4$ alkyl, CN, halogen, $C_1$-$C_4$ alkyloxy and $C_1$-$C_4$ haloalkyl, which substituents are the same or different
- X is selected from C and N;
- Y is selected from NH, O, S, S(O) and $S(O)_2$;
- A is selected from the group consisting of

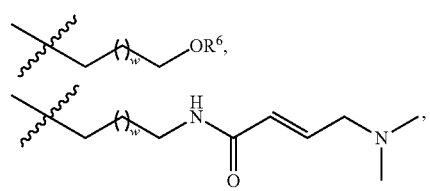

-continued

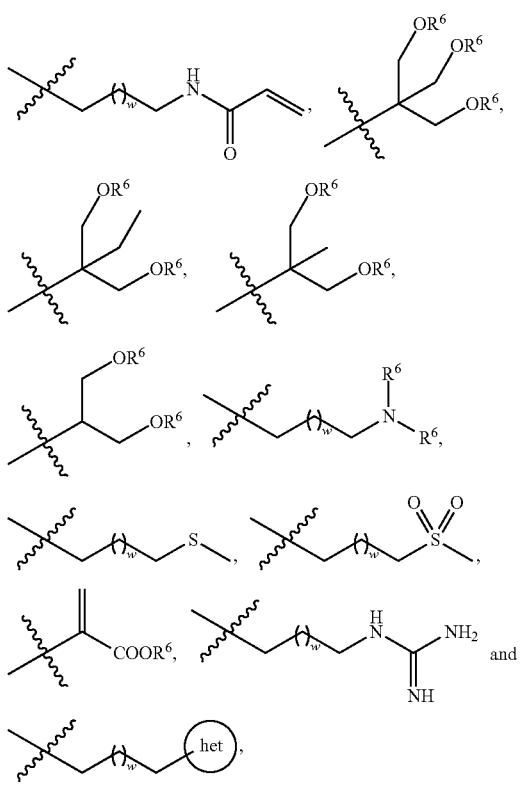

or A is a side chain of an amino acid selected from the group consisting of Gly, Ala, Ser, Lys, Arg, Thr, Asn, Gln, Phe and Glu

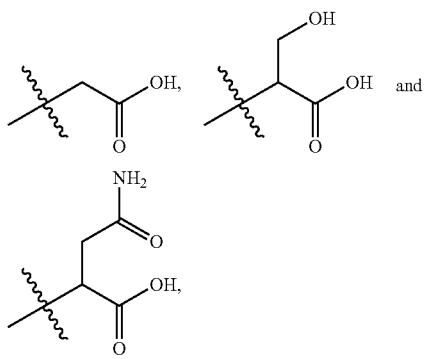

or A is a side chain of an amino acid selected from the group consisting of Gly, Ala, Ser, Lys, Arg, Thr, Asn, Gln, Phe and Glu, which is substituted with $R^6$

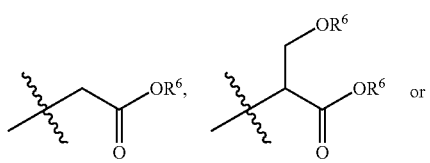

-continued

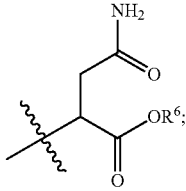

wherein,
$R^6$ is one or more substituents independently selected from the group consisting of H, $C_1$-$C_4$ alkyl, $C_1$-$C_4$ alkylcarbonyl, $C_1$-$C_4$ alkenylcarbonyl and $C_1$-$C_4$ alkylamino $C_1$-$C_4$ alkyl $C_1$-$C_4$ alkenylcarbonyl, which substituents are the same or different;

het is selected from saturated or aromatic heterocycles morpholine, N-methylpiperazine, tetrahydropyrrole, pyridine, thiophene, thiazole, triazole and tetrazole;

w is an integer from 0 to 2;
m is an integer from 1 to 5;
n is an integer from 1 to 3;
p is independently an integer from 0 to 2; and
q is an integer from 0 to 2.

3. The compound of Formula I according to claim 1, wherein,
$R^1$ is one or more substituents independently selected from the group consisting of H, $C_1$-$C_4$ alkyl, CN, halogen, $NH_2$, COOH, alkylamino, alkyloxy, haloalkyl and $Ar^1$, which substituents are the same or different;

wherein,
$Ar^1$ is selected from the group consisting of

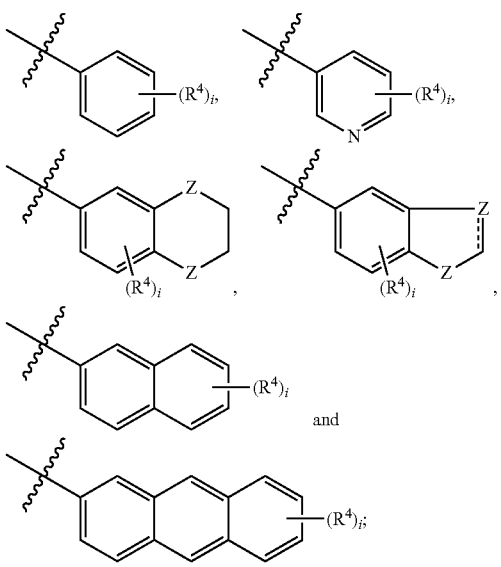

wherein,
$R^4$ is one or more substituents independently selected from the group consisting of H, $C_1$-$C_4$ alkyl, CN, halogen, $NH_2$, COOH, $C_1$-$C_4$ alkylamino, $C_1$-$C_4$ alkyloxy and $C_1$-$C_4$ haloalkyl, which substituents are the same or different;

i is an integer from 1 to 5;
Z is selected from the group consisting of C, NH, O, C(O), S, S(O) and $S(O)_2$;

$R^2$ is —$(CH_2)_k$—$Ar^2$;
  wherein,
  k is 1;
  $Ar^2$ is selected from

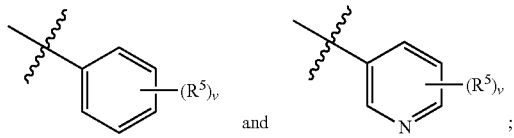

wherein,
  $R^5$ is one or more substituents independently selected from the group consisting of H, $CH_3$, $C_2H_5$, CN, F, Cl, $NH_2$, COOH, $CH_3NH$, $(CH_3)_2N$, $CH_3O$, $CF_3$ and $CHF_2$, which substituents are the same or different;
  v is an integer from 1 to 5;
$R^3$ is one or more substituents independently selected from the group consisting of H, $CH_3$, $C_2H_5$, CN, F, Cl, $CH_3O$, $CF_3$ and $CHF_2$, which substituents are the same or different;
X is selected from C and N;
Y is selected from NH, O, S, S(O) and $S(O)_2$;
A is selected from the group consisting of

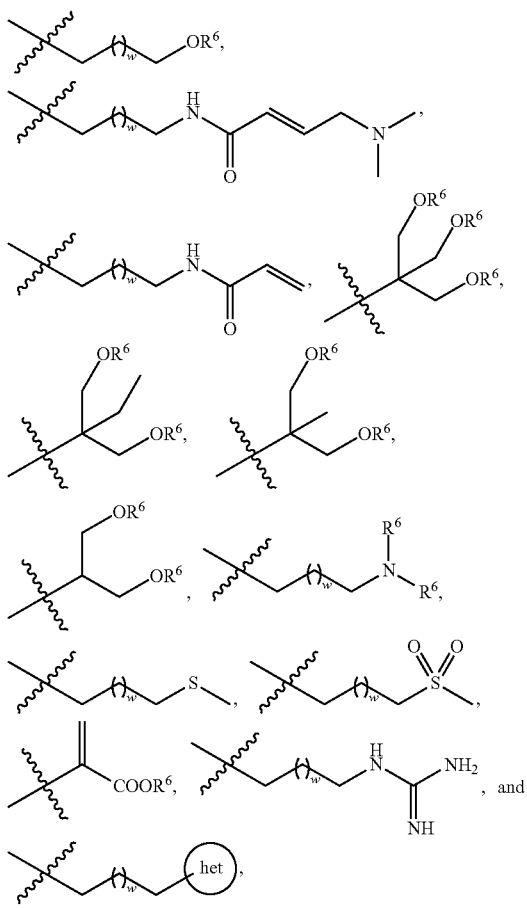

or A is a side chain of an amino acid selected from the group consisting of Gly, Ala, Ser, Lys, Arg, Thr, Asn, Gln, Phe and Glu

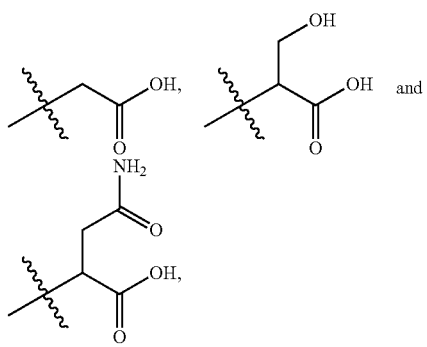

or A is a side chain of an amino acid selected from the group consisting of Gly, Ala, Ser, Lys, Arg, Thr, Asn, Gln, Phe and Glu, which is substituted with $R^6$

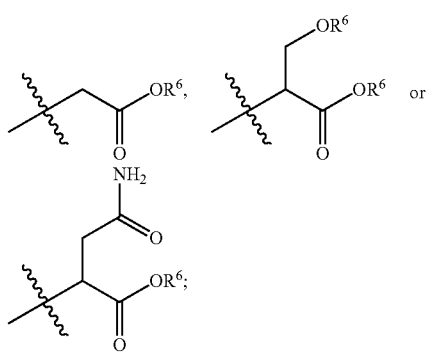

wherein,
  $R^6$ is one or more substituents independently selected from the group consisting of H, $C_1$-$C_4$ alkyl, $C_1$-$C_4$ alkylcarbonyl, $C_1$-$C_4$ alkenylcarbonyl and $C_1$-$C_4$ alkylamino $C_1$-$C_4$ alkyl $C_1$-$C_4$ alkenylcarbonyl, which substituents are the same or different;
  het is selected from saturated or aromatic heterocycles morpholine, N-methylpiperazine, tetrahydropyrrole, pyridine, thiophene, thiazole, triazole and tetrazole;
  w is an integer from 0 to 2;
  m is an integer from 1 to 5;
  n is an integer from 1 to 3;
  p is independently an integer from 0 to 2; and
  q is an integer from 0 to 2.
4. The compound of Formula I according to claim 1, wherein,
  $R^1$ is one or more substituents independently selected from the group consisting of H, $C_1$-$C_4$ alkyl, CN, halogen, $NH_2$, COOH, $C_1$-$C_4$ alkylamino, $C_1$-$C_4$ alkyloxy, $C_1$-$C_4$ haloalkyl and $Ar^1$, which substituents are the same or different;
  wherein,
  $Ar^1$ is selected from the group consisting of

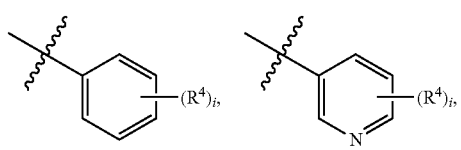

-continued

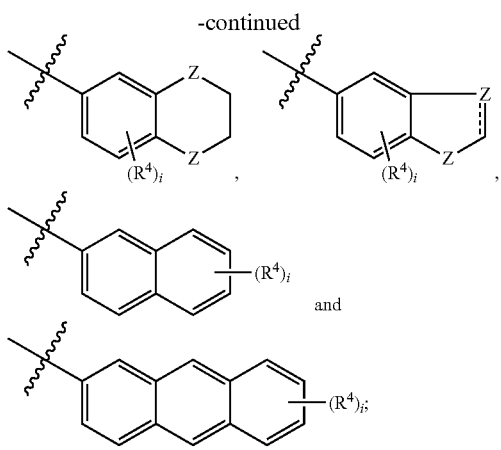

wherein,
R⁴ is one or more substituents independently selected from the group consisting of H, C₁-C₄ alkyl, CN, halogen, NH₂, COOH, C₁-C₄ alkylamino, C₁-C₄ alkyloxy and C₁-C₄ haloalkyl, which substituents are the same or different;
i is an integer from 1 to 5;
Z is selected from the group consisting of C, NH, O, C(O), S, S(O) and S(O)₂;
R² is —(CH₂)$_k$—Ar²;
wherein,
k is 1;
Ar² is selected from

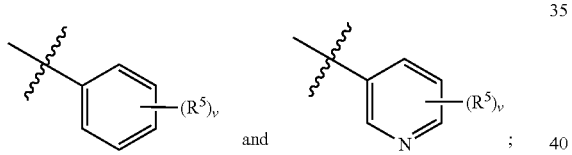

wherein,
R⁵ is one or more substituents independently selected from the group consisting of H, CH₃, C₂H₅, CN, F, Cl, NH₂, COOH, CH₃NH, (CH₃)₂N, CH₃O, CF₃ and CHF₂, which substituents are the same or different;
v is an integer from 1 to 5;
R³ is one or more substituents independently selected from the group consisting of CH₃, CN, F, Cl, CH₃O, CF₃ and CHF₂, which substituents are the same or different;
X is selected from C and N;
Y is selected from NH, O, S, S(O) and S(O)₂;
A is selected from the group consisting of

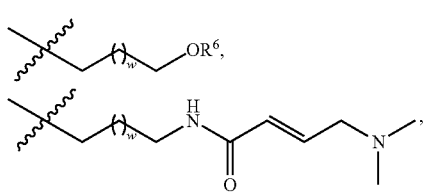

-continued

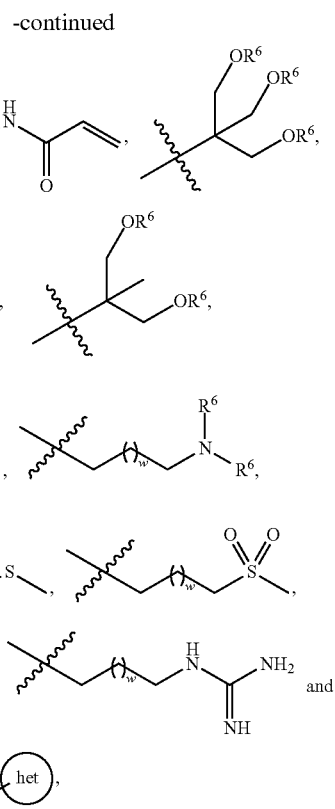

or A is a side chain of an amino acid selected from the group consisting of Gly, Ala, Ser, Lys, Arg, Thr, Asn, Gln, Phe and Glu

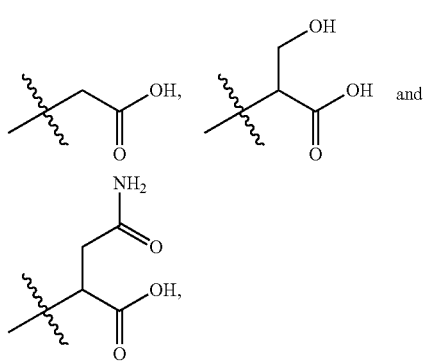

or A is a side chain of an amino acid selected from the group consisting of Gly, Ala, Ser, Lys, Arg, Thr, Asn, Gln, Phe and Glu, which is substituted with R⁶

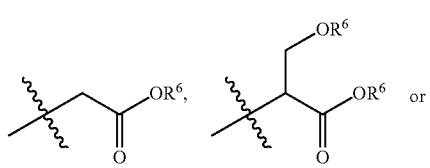

-continued

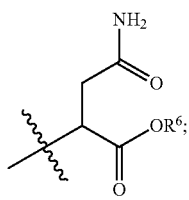

wherein,

R⁶ is one or more substituents independently selected from the group consisting of H, $CH_3$, $C_2H_5$, t-Bu, $CH_3CO$, $CH_2$=CHCO and $(CH_3)_2NCH_2CH$=CHCO, which substituents are the same or different;

het is selected from saturated or aromatic heterocycles morpholine, N-methylpiperazine, tetrahydropyrrole, pyridine, thiophene, thiazole, triazole and tetrazole;

w is an integer from 0 to 2;

m is an integer from 1 to 5;

n is an integer from 1 to 3;

p is independently an integer from 0 to 2; and q is an integer from 0 to 2.

5. The compound of Formula I according to claim 1, wherein,

R¹ is one or more substituents independently selected from the group consisting of H, $CH_3$, $C_2H_5$, CN, F, Cl, $NH_2$, COOH, $CH_3NH$, $(CH_3)_2N$, $CH_3O$, $CF_3$, $CHF_2$ and Ar¹, which substituents are the same or different;

wherein,

Ar¹ is selected from the group consisting of

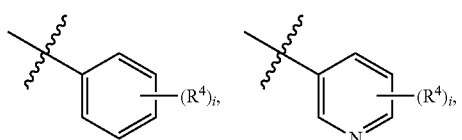

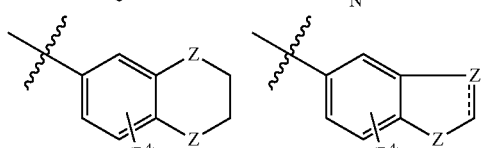

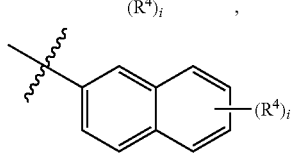

wherein,

R⁴ is one or more substituents independently selected from the group consisting of H, $CH_3$, $C_2H_5$, CN, F, Cl, $NH_2$, COOH, $CH_3NH$, $(CH_3)_2N$, $CH_3O$, $CF_3$ and $CHF_2$, which substituents are the same or different;

i is an integer from 1 to 3;

Z is selected from the group consisting of C, NH, O, C(O), S, S(O) and $S(O)_2$;

R² is $-(CH_2)_k-Ar^2$;

wherein, k is 1;

Ar² is selected from

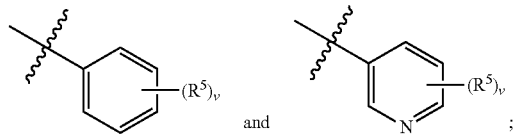

wherein,

R⁵ is one or more substituents independently selected from the group consisting of H, $CH_3$, $C_2H_5$, CN, F, Cl, $(CH_3)_2N$, $CF_3$ and $CHF_2$, which substituents are the same or different;

v is 1;

R³ is one or more substituents independently selected from the group consisting of $CH_3$, CN, F, Cl, $CH_3O$, $CF_3$ and $CHF_2$, which substituents are the same or different;

X is C;

Y is selected from NH, O, S, S(O) and $S(O)_2$;

A is selected from the group consisting of

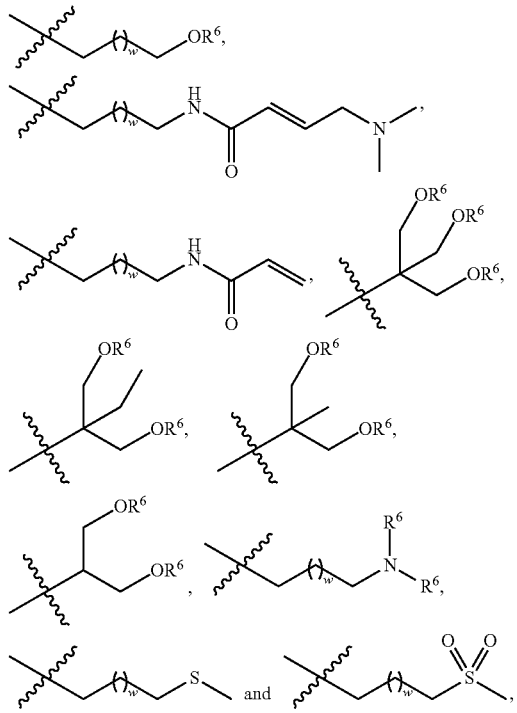

or A is a side chain of an amino acid selected from the group consisting of Gly, Ala, Ser, Lys, Arg, Thr, Asn, Gln, Phe and Glu

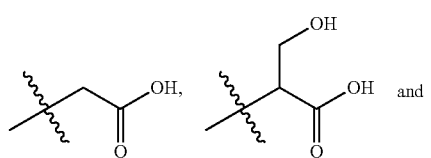

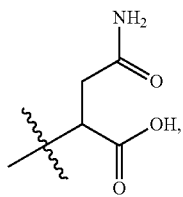

or A is a side chain of an amino acid selected from the group consisting of Gly, Ala, Ser, Lys, Arg, Thr, Asn, Gln, Phe and Glu, which is substituted with $R^6$

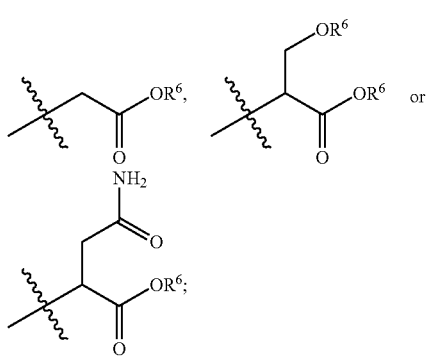

wherein,
R$^6$ is one or more substituents independently selected from the group consisting of H, CH$_3$, C$_2$H$_5$, t-Bu, CH$_3$CO, CH$_2$=CHCO and (CH$_3$)$_2$NCH$_2$CH=CHCO, which substituents are the same or different;
w is an integer from 0 to 2;
m is an integer from 1 to 3;
n is an integer from 1 to 2;
p is independently an integer from 0 to 2; and
q is an integer from 0 to 2.

6. The compound of Formula I according to claim 1, wherein,
R$^1$ is one or more substituents independently selected from the group consisting of CH$_3$, CN, F, Cl, CF$_3$ and Ar$^1$, which substituents are the same or different;
wherein,
Ar$^1$ is selected from the group consisting of

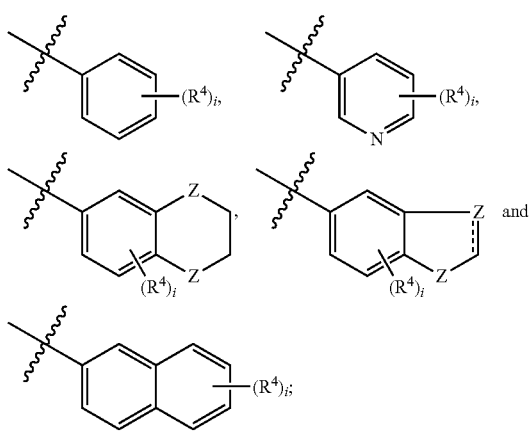

wherein,
R$^4$ is one or more substituents independently selected from the group consisting of H, CH$_3$, CN, F, Cl, (CH$_3$)$_2$N, CF$_3$ and CHF$_2$, which substituents are the same or different;
i is an integer from 1 to 3;
Z is selected from the group consisting of C, NH, O, C(O), S, S(O) and S(O)$_2$;
R$^2$ is —(CH$_2$)$_k$—Ar$^2$;
wherein,
k is 1;
Ar$^2$ is selected from

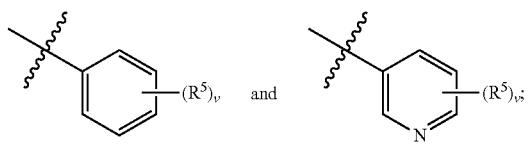

wherein,
R$^5$ is one or more substituents independently selected from the group consisting of CH$_3$, CN, F, (CH$_3$)$_2$N, CF$_3$ and CHF$_2$, which substituents are the same or different;
v is 1;
R$^3$ is one or more substituents independently selected from the group consisting of CH$_3$, CN, F, Cl, CH$_3$O, CF$_3$ and CHF$_2$, which substituents are the same or different;
X is C;
Y is selected from NH, O, S, S(O) and S(O)$_2$;
A is selected from the group consisting of

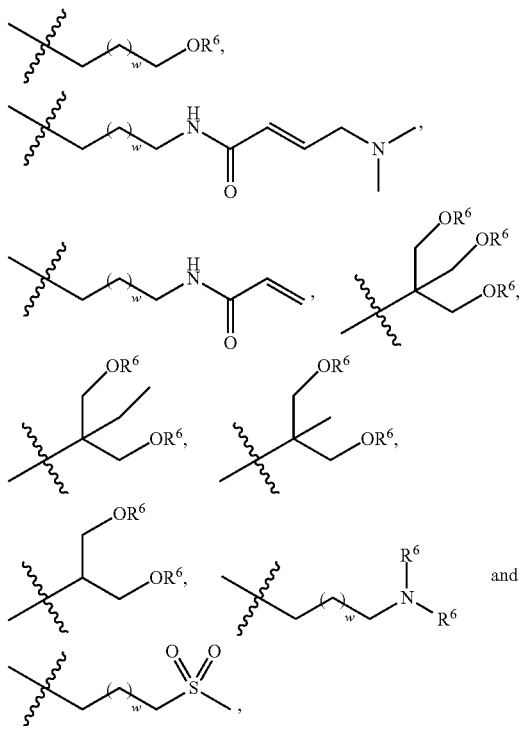

or A is a side chain of an amino acid selected from the group consisting of Gly, Ala, Ser, Lys, Arg, Thr, Asn, Gln, Phe and Glu

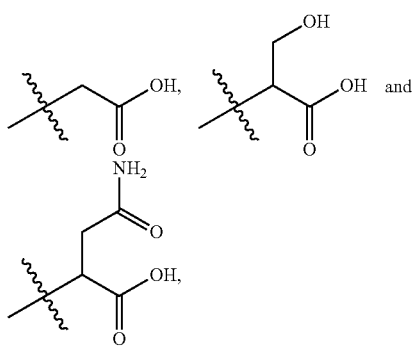

or A is a side chain of an amino acid selected from the group consisting of Gly, Ala, Ser, Lys, Arg, Thr, Asn, Gln, Phe and Glu, which is substituted with $R^6$

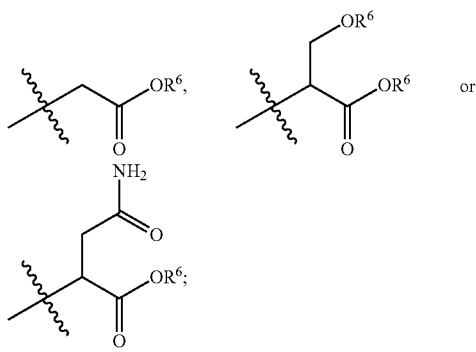

wherein,
$R^6$ is one or more substituents independently selected from the group consisting of H, $CH_3CO$, $CH_2$=CHCO and $(CH_3)_2NCH_2CH$=CHCO, which substituents are the same or different;
w is 1;
m is an integer from 1 to 3;
n is an integer from 1 to 2;
p is independently an integer from 0 to 2; and
q is an integer from 0 to 2.

7. The compound of Formula I according to claim 1, wherein,
$R^1$ is one or more substituents independently selected from the group consisting of $CH_3$, CN, F, Cl, $CF_3$ and $Ar^1$, which substituents are the same or different;
wherein,
$Ar^1$ is selected from the group consisting of

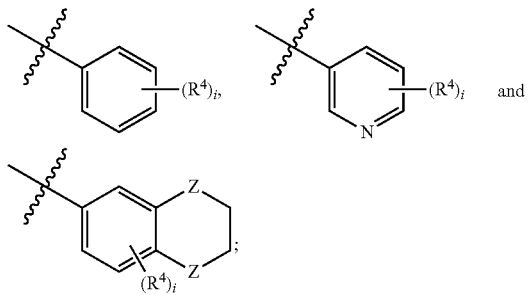

wherein,
$R^4$ is one or more substituents independently selected from the group consisting of H, $CH_3$, CN, F, Cl, $(CH_3)_2N$, $CF_3$ and $CHF_2$, which substituents are the same or different;
i is an integer from 1 to 3;
Z is selected from the group consisting of C, NH, O and C(O);
$R^2$ is $—(CH_2)_k—Ar^2$;
wherein,
k is 1;
$Ar^2$ is

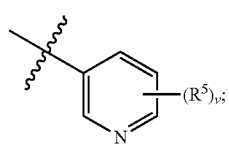

wherein,
$R^5$ is one or more substituents independently selected from the group consisting of $CH_3$, CN, F, $(CH_3)_2N$, $CF_3$ and $CHF_2$, which substituents are the same or different;
v is 1;
$R^3$ is one or more substituents independently selected from the group consisting of $CH_3$, F, Cl and $CH_3O$, which substituents are the same or different;
X is C;
Y is selected from NH and O;
A is selected from the group consisting of

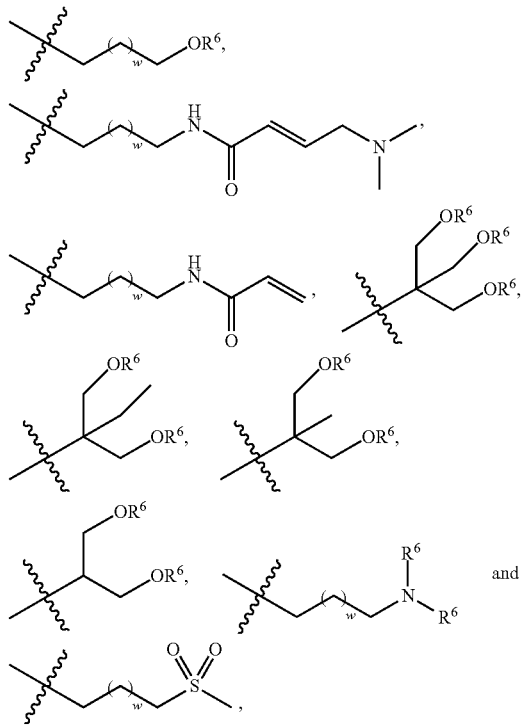

or A is a side chain of an amino acid selected from the group consisting of Gly, Ala, Ser, Lys, Arg, Thr, Asn, Gln, Phe and Glu

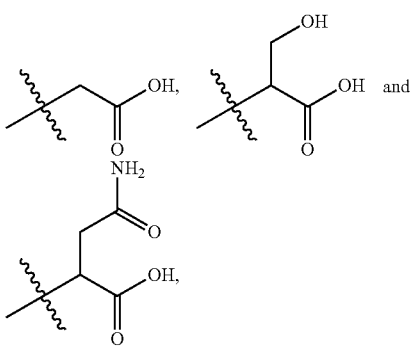

or A is a side chain of an amino acid selected from the group consisting of Gly, Ala, Ser, Lys, Arg, Thr, Asn, Gln, Phe and Glu, which is substituted with $R^6$

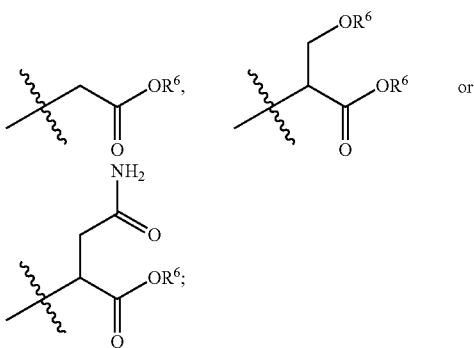

wherein,
$R^6$ is one or more substituents independently selected from the group consisting of H and $CH_3CO$, which substituents are the same or different;
w is 1;
m is 2;
n is an integer from 1 to 2;
p is 0; and
q is an integer from 0 to 1.

8. The compound of Formula I according to claim 1, wherein,
$R^1$ is two substituents independently selected from the group consisting of $CH_3$, CN, and $Ar^1$, which substituents are the same or different;
wherein,
$Ar^1$ is

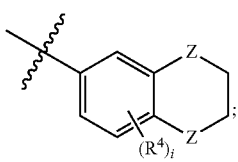

wherein,
$R^4$ is selected from the group consisting of H, $CH_3$, CN, F or Cl;
i is 1;
Z is 0;

$R^2$ is $—(CH_2)_k—Ar^2$;
wherein,
k is 1;
$Ar^2$ is

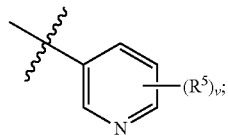

wherein,
$R^5$ is one or more substituents independently selected from the group consisting of $CH_3$, CN, F, $(CH_3)_2N$ and $CF_3$, which substituents are the same or different;
v is 1;
$R^3$ is one or more substituents independently selected from the group consisting of $CH_3$, F, Cl and $CH_3O$, which substituents are the same or different;
X is C;
Y is selected from NH and O;
A is selected from the group consisting of

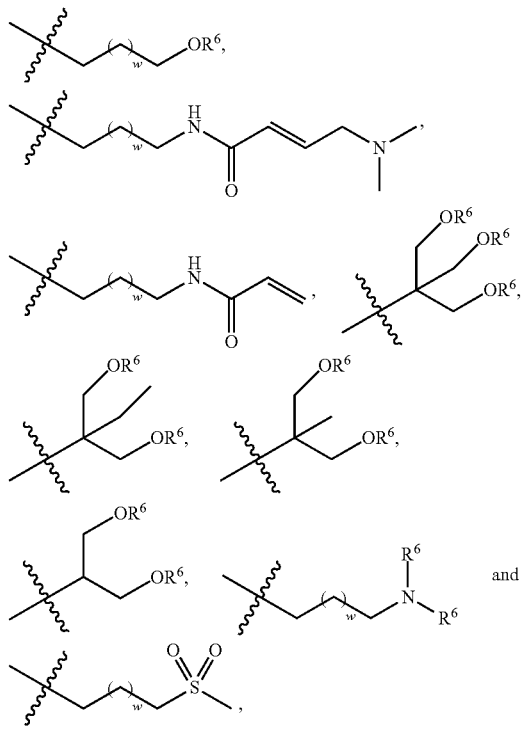

or A is a side chain of an amino acid selected from the group consisting of Gly, Ala, Ser, Lys, Arg, Thr, Asn, Gln, Phe and Glu

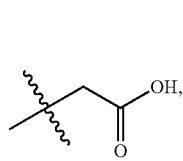 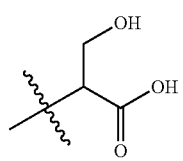 and

-continued

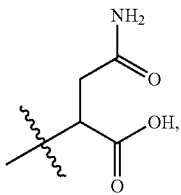

or A is a side chain of an amino acid selected from the group consisting of Gly, Ala, Ser, Lys, Arg, Thr, Asn, Gln, Phe and Glu, which is substituted with $R^6$

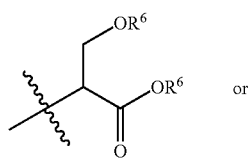 or

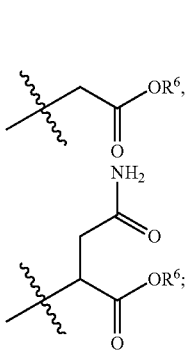

wherein,
$R^6$ is one or more substituents independently selected from the group consisting of H and $CH_3CO$, which substituents are the same or different;
w is 1;
m is 2;
n is an integer from 1 to 2;
p is 0; and
q is an integer from 0 to 1.

9. The Formula I according to claim 1, wherein the compound is selected from the group consisting of
1-((2-(2-(3-cyanophenyl)methoxy-4-(2-methyl-(1,1'-diphenyl)-3-yl-methoxy))benzylamino)- 2-ethyl)-3-(2-(N-morpholine)ethyl)urea;
1-((2-(2-(3-cyanophenyl)methoxy-4-(2-methyl-(1,1'-diphenyl)-3-yl-methoxy))benzylamino)- 2-ethyl)-3-(2-hydroxyethyl)urea;
1-((2-(2-(3-cyanophenyl)methoxy-4-(2-methyl-(1,1'-diphenyl)-3-yl-methoxy))benzylamino)- 2-ethyl)-3-(2-tert-butyl-O-tert-butyl-L-serinate-2-yl)urea;
1-((2-(2-(5-cyanopyridin-3-yl)methoxy-4-(2-cyano-3-(2,3-dihydrobenzo[b])[1,4-dioxin-6- yl])benzyloxy)-5-methyl)benzylamino)-2-ethyl)-3-(2-hydroxyethyl) urea;
1 -((2-(2-(5 -cyanopyridin-3 -yl)methoxy-4-(2-cyano-3 -(2,3 -dihydrobenzo[b])[1,4-dioxin-6- yl])benzyloxy)-5 -methyl)benzylamino)-2-ethyl))-3 -(1 ,3 -dihydroxy-2-(hydroxymethyl)propan-2- yl)urea;
1-((2-(2-(5-cyanopyridin-3-yl)methoxy-4-(2-cyano-3-(2,3-dihydrobenzo[b])[1,4-dioxin-6- yl])benzyloxy)-5-methyl)benzylamino)-2-ethyl))-3-(2-acryl-2-yl)urea;
1-((2-(2-(5-cyanopyridin-3-yl)methoxy-4-(2-cyano-3-(2,3-dihydrobenzo[b])[1,4-dioxin-6- yl])benzyloxy)-5-methyl)benzylamino)-2-(2-aminoethoxy)ethyl)-3-(2-hydroxyethyl)urea;
1-((2-(2-(5-cyanopyridin-3-yl)methoxy-4-(2-cyano-3-(2,3-dihydrobenzo[b])[1,4-dioxin-6- yl])benzyloxy)-5-methyl)benzylamino)-2-ethyl))-3-(2-(N-morpholine)ethyl)urea;
1-((2-(2-(5-cyanopyridin-3-yl)methoxy-4-(2-cyano-3-(2,3-dihydrobenzo[b])[1,4-dioxin-6- yl])benzyloxy)-5-methyl)benzylamino)-2-(2-aminoethoxy)ethyl)-3-(2-(methylsulfonyl)ethyl)urea;
1-((2-(2-(5-cyanopyridin-3-yl)methoxy-4-(2-cyano-3-(2,3-dihydrobenzo[b])[1,4-dioxin-6- yl])benzyloxy)-5-methyl)benzylamino)-2-(2-aminoethoxy)ethyl)-3-(2-(N,N'- dimethylamino)ethyl)urea;
1-((2-(2-(5-cyanopyridin-3-yl)methoxy-4-(2-cyano-3-(2,3-dihydrobenzo[b])[1,4-dioxin-6- yl])benzyloxy)-5-methyl)benzylamino)-2-ethyl))-3-(2-(N,N'-dimethylamino)ethyl)urea;
1-((2-(2-(5-cyanopyridin-3-yl)methoxy-4-(2-cyano-3-(2,3-dihydrobenzo[b])[1,4-dioxin-6- yl])benzyloxy)-5-methyl)benzylamino)-2-ethyl))-3-(2-(methanesulfonyl)ethyl)urea;
1-((2-(2-(5-cyanopyridin-3-yl)methoxy-4-(2-cyano-3-(2,3-dihydrobenzo[b])[1,4-dioxin-6- yl])benzyloxy)-5-methyl)benzylamino)-2-ethyl))-3-(L-serine-2-yl)urea; and
1-((2-(2-(5-cyanopyridin-3-yl)methoxy-4-(2-cyano-3-(2,3-dihydrobenzo[b])[1,4-dioxin-6- yl])benzyloxy)-5-methyl)-benzylamino)-2-ethyl)-3-(2-acrylamidoethyl) urea.

10. A method for preparing the compound of Formula I according to claim 1, comprising, subjecting a compound of Formula II and a compound of Formula III to a reductive amination reaction in the presence of a reductant,

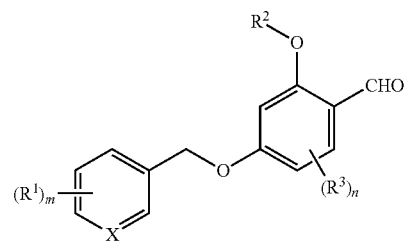

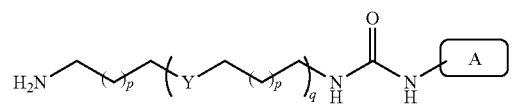

wherein each variable is as defined in claim 1.

11. The method according to claim 10, wherein the reductant is selected from $NaBH_4$, $NaBH_3CN$ and $NaBH_3OAc$.

12. The method according to claim 10, wherein the reductive amination reaction is carried out in the presence of a basic catalyst, and the basic catalyst is selected from TEA and DIPEA.

13. The method according to claim 10, wherein the method is carried out in the presence of a desiccant, and the desiccant is selected from anhydrous $MgSO_4$, anhydrous $Na_2SO_4$ and molecular sieves.

14. The method according to claim 10, wherein the reductive amination reaction is carried out in a solvent, and the solvent is selected from $CH_3OH$, $CH_2Cl_2$ and 1,2-dichloroethane.

15. The method according to claim 10, wherein the compound of Formula III is prepared by a one-pot process of a reactive intermediate, which is formed from a compound of Formula III-1 under an action of carbonyldiimidazole (CDI), and a compound of Formula III-2,

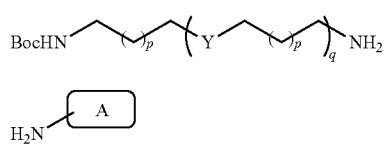

III-1

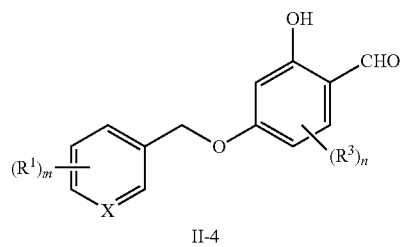

II-4 wherein each variable is as defined in claim 1.

16. The method according to claim 15, wherein the compound of Formula III is prepared in the presence of a basic catalyst selected from TEA and DIPEA.

17. The method according to claim 15, wherein the compound of Formula III is prepared in the presence of an acid catalyst selected from concentrated HCl, TFA and HOAc.

18. The method according to claim 15, wherein the compound of Formula III is prepared in the presence of a solvent selected from $CH_2Cl_2$, $CH_3OH$ and $CH_3CN$.

19. The method according to claim 10, wherein the compound of Formula II is a compound of Formula II-4, which is prepared by the following nucleophilic substitution reaction of a compound of Formula II-2 in the presence of a basic catalyst and a solvent,

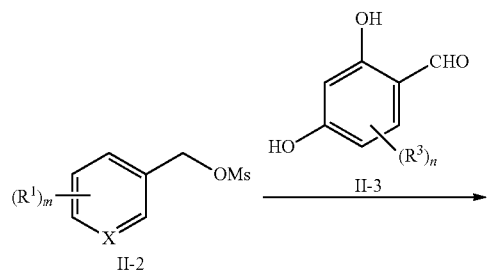

wherein each variable is as defined in claim 1.

20. The method according to claim 19, wherein the basic catalyst is selected from $K_2CO_3$ and $Cs_2CO_3$.

21. The method according to claim 19, wherein the solvent is selected from $CH_3CN$ and DMF.

22. A pharmaceutical composition, comprising the compound of Formula I according to claim 1, and an optional pharmaceutically acceptable carrier, adjuvant or diluent.

23. A method for treating or preventing diseases related to PD-1/PD-L1 signaling pathways, wherein the diseases related to PD-1/PD-L1 signaling pathways are selected from cancer, autoimmune diseases and chronic infectious diseases, comprising using the compound according to claim 1.

24. A method for treating diseases related to PD-1/PD-L1 signaling pathways, wherein the diseases related to PD-1/PD-L1 signaling pathways are selected from cancer, autoimmune diseases and chronic infectious diseases, comprising using the pharmaceutical composition according to claim 22.

25. The pharmaceutical composition according to claim 22, which is in the form of preparations, and has a unit dosage of 0.0001-200 mg.

* * * * *